(12) United States Patent
Nelson et al.

(10) Patent No.: US 7,297,133 B2
(45) Date of Patent: *Nov. 20, 2007

(54) SURGICAL SUCTION IRRIGATOR

(75) Inventors: Charles L. Nelson, Pleasanton, CA (US); Heber Saravia, San Francisco, CA (US); John Nguyen, San Jose, CA (US); William P. Pennybacker, Fremont, CA (US)

(73) Assignee: Stryker Corporation, Kalamazoo, MI (US)

( * ) Notice: Subject to any disclaimer, the term of this patent is extended or adjusted under 35 U.S.C. 154(b) by 665 days.

This patent is subject to a terminal disclaimer.

(21) Appl. No.: 10/648,693

(22) Filed: Aug. 26, 2003

(65) Prior Publication Data

US 2005/0075600 A1 Apr. 7, 2005

Related U.S. Application Data

(63) Continuation of application No. 09/676,517, filed on Oct. 2, 2000, now Pat. No. 6,623,445, which is a continuation of application No. 08/769,428, filed on Dec. 19, 1996, now Pat. No. 6,213,970, which is a continuation of application No. 08/502,708, filed on Jul. 14, 1995, now abandoned, which is a continuation-in-part of application No. 08/176,130, filed on Dec. 30, 1993, now Pat. No. 5,484,402.

(51) Int. Cl.
*A61M 1/00* (2006.01)
(52) U.S. Cl. ...................................................... 604/35
(58) Field of Classification Search ................ 604/35, 604/33, 250, 408, 246; 222/401; 415/80, 415/98; 432/84
See application file for complete search history.

(56) References Cited

U.S. PATENT DOCUMENTS 509,220 A 11/1893 Gustafson (Continued)

FOREIGN PATENT DOCUMENTS

DE 24 16 099 4/1975

(Continued)

OTHER PUBLICATIONS

Ethicon, Pfizer/Valley Lab and Bard/Davol photos (10 photos) Jun. 25, 1993.

(Continued)

*Primary Examiner*—Nicholas D. Lucchesi
*Assistant Examiner*—Christopher D. Koharski
(74) *Attorney, Agent, or Firm*—Flynn, Thiel, Boutell & Tanis, P.C.

(57) ABSTRACT

A surgical irrigation system is suitable for endoscopic and other surgical procedures. A hand held handpiece has a forward protruding hollow tip for supplying irrigation liquid to a surgical site, a hand actuable control for controlling irrigation liquid flow to the tip, and an irrigation liquid inlet. A self contained pumping unit is locatable adjacent a source of irrigation liquid and remote from the handpiece. The pumping unit comprises a housing containing an outlet for irrigation liquid, a pumping member for pumping irrigation liquid through the outlet, a motor for driving the pumping member, and an electric battery assembly for energizing the motor. An elongate tube connects the pumping outlet to the handpiece irrigation liquid inlet for supplying pumped irrigation liquid to the handpiece.

29 Claims, 52 Drawing Sheets

U.S. PATENT DOCUMENTS

| | | |
|---|---|---|
| 602,666 A | 4/1898 | Schroeder |
| 738,503 A | 9/1903 | Waters |
| 790,353 A | 5/1905 | Estlingen |
| 1,317,851 A | 10/1919 | Arnett |
| 1,503,279 A | 7/1924 | Nixon |
| 1,538,007 A | 5/1925 | Schellin |
| 1,846,596 A | 2/1932 | Hertzberg |
| 2,012,886 A | 8/1935 | Lowry |
| 2,112,629 A | 3/1938 | Lloyd |
| 2,139,653 A | 12/1938 | Belfrage |
| 2,197,995 A | 4/1940 | Crowley |
| 2,243,285 A | 5/1941 | Pope |
| 2,243,299 A | 5/1941 | Travers |
| 2,494,088 A | 1/1950 | Dulity |
| 2,531,793 A | 11/1950 | Sulek |
| 2,595,491 A | 5/1952 | Schweikert |
| 2,634,885 A | 4/1953 | North |
| 2,662,485 A | 12/1953 | Ilfrey |
| 2,684,049 A | 7/1954 | Hollis |
| 2,727,678 A | 12/1955 | Henderson |
| 2,733,713 A | 2/1956 | Kabnick |
| 2,781,154 A | 2/1957 | Meredith |
| 2,802,466 A | 8/1957 | Thomas |
| 2,847,007 A | 8/1958 | Fox |
| 2,874,696 A | 2/1959 | Bried |
| 2,908,273 A | 10/1959 | Huston |
| 2,993,654 A | 7/1961 | Norton |
| 3,001,288 A | 9/1961 | Freedman |
| 3,014,623 A | 12/1961 | Horn et al. |
| 3,039,272 A | 6/1962 | Frick |
| 3,044,465 A | 7/1962 | Anderson et al. |
| 3,048,121 A | 8/1962 | Sheesley |
| 3,065,749 A | 11/1962 | Brass |
| 3,070,089 A | 12/1962 | Dick |
| 3,135,259 A | 6/1964 | Evans |
| 3,208,145 A | 9/1965 | Turner |
| 3,227,158 A | 1/1966 | Mattingly |
| 3,237,306 A | 3/1966 | Staunt |
| 3,263,618 A | 8/1966 | Carpenter |
| 3,295,371 A | 1/1967 | Smith |
| 3,316,845 A | 5/1967 | Schumann |
| 3,353,537 A | 11/1967 | Knox et al. |
| 3,359,909 A | 12/1967 | Johnson et al. |
| 3,393,673 A | 7/1968 | Mattingly |
| 3,416,567 A | 12/1968 | VonDardel et al. |
| 3,425,410 A | 2/1969 | Cammack |
| 3,426,743 A | 2/1969 | Chesnut et al. |
| 3,448,766 A | 6/1969 | Schuele |
| 3,452,746 A | 7/1969 | Shanhouse |
| 3,484,121 A | 12/1969 | Quinton |
| 3,508,546 A | 4/1970 | Rogers et al. |
| 3,515,130 A | 6/1970 | Tsujino |
| 3,561,433 A | 2/1971 | Kovach |
| 3,601,164 A | 8/1971 | Bruce |
| 3,605,556 A | 9/1971 | Erdmann |
| 3,635,607 A | 1/1972 | Grise |
| 3,653,377 A | 4/1972 | Rebold |
| 3,702,141 A | 11/1972 | Wetterhorn |
| 3,713,533 A | 1/1973 | Reimels |
| 3,731,411 A | 5/1973 | Barber et al. |
| 3,731,676 A | 5/1973 | Rebold |
| 3,749,090 A | 7/1973 | Stewart |
| 3,762,411 A | 10/1973 | Lloyd et al. |
| 3,765,802 A | 10/1973 | Leitermann et al. |
| 3,768,472 A | 10/1973 | Hodosh et al. |
| 3,771,522 A | 11/1973 | Waysilk et al. |
| 3,784,235 A | 1/1974 | Kessler et al. |
| 3,794,031 A | 2/1974 | Bloom |
| 3,853,245 A | 12/1974 | Branch |
| 3,861,383 A | 1/1975 | Kovach |
| 3,883,074 A | 5/1975 | Lambert |
| 3,889,675 A | 6/1975 | Stewart |
| 3,895,741 A | 7/1975 | Nugent |
| 3,949,753 A | 4/1976 | Dockhorn |
| 3,965,934 A | 6/1976 | Rosenberg |
| 3,982,540 A | 9/1976 | Ross |
| 3,986,266 A | 10/1976 | Vellender |
| 3,993,054 A | 11/1976 | Newman |
| 4,007,739 A | 2/1977 | Bron et al. |
| 4,030,495 A | 6/1977 | Virag |
| 4,030,498 A | 6/1977 | Tompkins |
| 4,061,142 A | 12/1977 | Tuttle |
| 4,099,527 A | 7/1978 | Howell |
| 4,111,391 A | 9/1978 | Pilolla |
| 4,123,091 A | 10/1978 | Cosentino et al. |
| 4,205,676 A | 6/1980 | Humphrey et al. |
| 4,215,476 A | 8/1980 | Armstrong |
| 4,248,589 A | 2/1981 | Lewis |
| 4,250,872 A | 2/1981 | Tamari |
| 4,257,416 A | 3/1981 | Prager |
| 4,267,947 A | 5/1981 | Wasserstrom |
| 4,275,726 A | 6/1981 | Schael |
| 4,276,023 A | 6/1981 | Phillips et al. |
| 4,278,078 A | 7/1981 | Smith |
| 4,282,867 A | 8/1981 | Du Toit |
| 4,289,158 A | 9/1981 | Nehring |
| 4,290,454 A | 9/1981 | Shetler |
| 4,294,251 A | 10/1981 | Greenwald et al. |
| 4,300,748 A | 11/1981 | Kreeley |
| 4,313,699 A | 2/1982 | Steele |
| 4,314,560 A | 2/1982 | Helfgott et al. |
| 4,346,869 A | 8/1982 | MacNeill |
| 4,350,477 A | 9/1982 | Mazal |
| 4,395,205 A | 7/1983 | McCullough |
| 4,424,010 A | 1/1984 | McCullough |
| 4,424,055 A | 1/1984 | Herman |
| 4,428,345 A | 1/1984 | Bertsch et al. |
| 4,428,748 A | 1/1984 | Peyman et al. |
| 4,436,495 A | 3/1984 | McCullough |
| 4,445,819 A | 5/1984 | Walling |
| 4,449,827 A | 5/1984 | Karkiewicz |
| 4,451,069 A | 5/1984 | Melone |
| 4,460,358 A | 7/1984 | Somerville et al. |
| 4,468,221 A | 8/1984 | Mayfield |
| 4,472,120 A | 9/1984 | McCullough |
| 4,482,345 A | 11/1984 | Chow et al. |
| 4,484,769 A | 11/1984 | Lacey |
| 4,489,750 A | 12/1984 | Nehring |
| 4,493,694 A | 1/1985 | Wuchinich |
| 4,502,502 A | 3/1985 | Krug |
| 4,508,532 A | 4/1985 | Drews et al. |
| 4,509,507 A | 4/1985 | Yabe |
| 4,512,066 A | 4/1985 | McCullough |
| 4,515,532 A | 5/1985 | Walling |
| 4,519,385 A | 5/1985 | Atkinson et al. |
| 4,526,573 A | 7/1985 | Lester et al. |
| 4,534,758 A | 8/1985 | Akers et al. |
| 4,535,773 A | 8/1985 | Yoon |
| 4,537,182 A | 8/1985 | Otani |
| 4,537,209 A | 8/1985 | Sasa |
| D281,535 S | 11/1985 | Atkinson et al. |
| 4,552,130 A | 11/1985 | Kinoshita |
| 4,553,957 A | 11/1985 | Williams et al. |
| 4,561,431 A * | 12/1985 | Atkinson .................... 601/161 |
| 4,561,856 A | 12/1985 | Cochran |
| 4,580,816 A | 4/1986 | Campbell et al. |
| 4,583,531 A | 4/1986 | Mattchen |
| 4,592,749 A | 6/1986 | Ebling et al. |
| 4,596,558 A | 6/1986 | Smith et al. |
| 4,601,710 A | 7/1986 | Moll |
| 4,604,089 A | 8/1986 | Santangelo et al. |
| 4,621,770 A | 11/1986 | Sayen |
| 4,634,420 A | 1/1987 | Spinosa et al. |
| 4,635,621 A | 1/1987 | Atkinson |

| | | | | | | |
|---|---|---|---|---|---|---|
| 4,647,738 A | 3/1987 | Diamond | | 5,449,357 A | 9/1995 | Zinmanti |
| 4,655,197 A | 4/1987 | Atkinson | | 5,464,391 A | 11/1995 | DeVale |
| 4,655,744 A | 4/1987 | Thistle et al. | | 5,470,305 A | 11/1995 | Arnett et al. |
| 4,655,752 A | 4/1987 | Honkanen et al. | | 5,484,402 A | 1/1996 | Saravia et al. |
| 4,655,754 A | 4/1987 | Richmond | | 5,487,649 A | 1/1996 | Dorsey, III et al. |
| 4,655,765 A | 4/1987 | Swift | | 5,514,089 A | 5/1996 | Walbrink et al. |
| 4,662,829 A | 5/1987 | Nehring | | 5,522,796 A | 6/1996 | Dorsey, III |
| 4,667,655 A | 5/1987 | Ogiu et al. | | 5,562,640 A | 10/1996 | McCabe et al. |
| 4,692,140 A | 9/1987 | Olson | | 5,573,504 A | 11/1996 | Dorsey, III |
| 4,696,669 A | 9/1987 | Menhusen | | 5,578,000 A | 11/1996 | Greff et al. |
| 4,705,500 A | 11/1987 | Reimels et al. | | 5,586,977 A | 12/1996 | Dorsey, III |
| 4,741,678 A | 5/1988 | Nehring | | 5,607,391 A | 3/1997 | Klinger et al. |
| 4,748,970 A | 6/1988 | Nakajima | | 5,609,573 A | 3/1997 | Sandock |
| 4,759,349 A | 7/1988 | Betz et al. | | 5,647,852 A | 7/1997 | Atkinson |
| 4,764,165 A | 8/1988 | Reimels et al. | | D385,889 S | 11/1997 | Kullas et al. |
| 4,765,165 A | 8/1988 | Reimels et al. | | 5,707,351 A | 1/1998 | Dorsey, III |
| 4,765,588 A | 8/1988 | Atkinson | | 5,718,668 A | 2/1998 | Arnett et al. |
| 4,776,840 A | 10/1988 | Freitas et al. | | 5,746,719 A | 5/1998 | Farra et al. |
| 4,799,481 A | 1/1989 | Transue et al. | | 5,746,721 A | 5/1998 | Pasch et al. |
| 4,817,599 A | 4/1989 | Drews | | 5,792,098 A | 8/1998 | Felix et al. |
| 4,857,068 A | 8/1989 | Kahn | | 5,792,108 A | 8/1998 | Felix et al. |
| 4,872,837 A | 10/1989 | Issalene et al. | | 5,807,313 A | 9/1998 | Delk et al. |
| 4,892,469 A | 1/1990 | McCullough et al. | | 5,812,770 A | 9/1998 | Sakai |
| 4,911,621 A | 3/1990 | McCullough et al. | | 5,827,218 A | 10/1998 | Nguyen et al. |
| 4,925,450 A | 5/1990 | Imonti et al. | | 5,924,448 A | 7/1999 | West |
| 4,927,340 A | 5/1990 | McCullough | | 5,941,851 A | 8/1999 | Coffey et al. |
| 4,935,005 A | 6/1990 | Haines | | 6,022,329 A | 2/2000 | Arnett et al. |
| 4,941,872 A | 7/1990 | Felix et al. | | 6,059,754 A | 5/2000 | Pasch et al. |
| 4,957,483 A | 9/1990 | Gonser et al. | | 6,077,246 A | 6/2000 | Kullas et al. |
| 4,978,282 A | 12/1990 | Fu et al. | | 6,095,772 A | 8/2000 | Ramey et al. |
| 4,982,739 A | 1/1991 | Hemstreet et al. | | 6,099,494 A | 8/2000 | Henniges et al. |
| 5,019,038 A | 5/1991 | Linden | | 6,106,494 A | 8/2000 | Saravia et al. |
| 5,037,431 A | 8/1991 | Summers et al. | | 6,156,004 A | 12/2000 | Tremaine et al. |
| 5,046,486 A | 9/1991 | Grulke et al. | | 6,162,194 A | 12/2000 | Shipp |
| 5,049,071 A | 9/1991 | Davis et al. | | 6,176,847 B1 | 1/2001 | Humphreys, Jr. et al. |
| 5,053,002 A | 10/1991 | Barlow | | 6,179,807 B1 | 1/2001 | Henniges et al. |
| 5,054,947 A | 10/1991 | Frank et al. | | 6,200,292 B1 | 3/2001 | French et al. |
| 5,057,015 A | 10/1991 | Fleer | | 6,213,970 B1 * | 4/2001 | Nelson et al. ................ 604/35 |
| 5,098,387 A | 3/1992 | Wiest et al. | | 6,293,926 B1 | 9/2001 | Sorensen et al. |
| 5,098,405 A | 3/1992 | Peterson et al. | | 6,352,527 B1 | 3/2002 | Henniges et al. |
| 5,100,058 A | 3/1992 | Wei | | 6,358,224 B1 | 3/2002 | Tims et al. |
| 5,120,305 A | 6/1992 | Boehringer et al. | | 6,371,934 B1 | 4/2002 | Jackson et al. |
| 5,142,723 A | 9/1992 | Lustig | | 6,394,996 B1 | 5/2002 | Lawrence et al. |
| 5,147,292 A | 9/1992 | Kullas et al. | | 6,436,072 B1 | 8/2002 | Kullas et al. |
| 5,170,779 A | 12/1992 | Ginsberg | | 6,461,323 B2 | 10/2002 | Fowler et al. |
| 5,176,629 A | 1/1993 | Kullas et al. | | 6,471,668 B2 | 10/2002 | Henniges et al. |
| 5,186,714 A | 2/1993 | Boudreault et al. | | 6,485,452 B1 | 11/2002 | French et al. |
| 5,188,591 A | 2/1993 | Dorsey, III | | 6,527,743 B1 | 3/2003 | Fowler et al. |
| 5,195,958 A | 3/1993 | Phillips | | 6,623,445 B1 * | 9/2003 | Nelson et al. ................ 604/35 |
| 5,195,959 A | 3/1993 | Smith | | 6,626,827 B1 | 9/2003 | Felix et al. |
| 5,197,460 A | 3/1993 | Ito | | 6,635,031 B2 | 10/2003 | Fowler et al. |
| 5,203,769 A | 4/1993 | Clement et al. | | 6,685,667 B1 | 2/2004 | Delk et al. |
| 5,224,929 A | 7/1993 | Remiszewski | | 2001/0025160 A1 | 9/2001 | Felix et al. |
| 5,244,459 A | 9/1993 | Hill | | 2002/0082557 A1 | 6/2002 | Jackson et al. |
| 5,246,422 A | 9/1993 | Favre | | 2002/0151837 A1 | 10/2002 | Shipp |
| 5,261,905 A | 11/1993 | Doresey, III | | 2003/0212363 A1 | 11/2003 | Shipp |
| 5,269,750 A | 12/1993 | Grulke et al. | | 2004/0097872 A1 | 5/2004 | Delk et al. |
| 5,281,214 A | 1/1994 | Wilkins et al. | | | | |
| 5,295,956 A | 3/1994 | Bales et al. | | FOREIGN PATENT DOCUMENTS | | |
| 5,303,735 A | 4/1994 | Cerola et al. | | | | |
| 5,305,735 A | 4/1994 | Welden | | EP | 0 258 901 | 3/1988 |
| 5,322,503 A | 6/1994 | Desai | | FR | 1 325 670 | 3/1963 |
| 5,322,506 A | 6/1994 | Kullas | | GB | 1 264 138 | 2/1972 |
| 5,333,603 A | 8/1994 | Schuman | | GB | 2 063 674 A | 6/1981 |
| 5,334,140 A | 8/1994 | Phillips | | WO | WO81/01794 | 7/1981 |
| 5,336,238 A | 8/1994 | Holmes et al. | | WO | WO81/02335 | 8/1981 |
| 5,348,555 A | 9/1994 | Zinnanti | | WO | WO85/03982 | 9/1985 |
| 5,380,277 A | 1/1995 | Phillips | | WO | WO86/04247 | 8/1986 |
| 5,388,612 A | 2/1995 | Cerola et al. | | WO | WO91/12830 | 9/1991 |
| 5,391,145 A | 2/1995 | Dorsey | | WO | WO92/21388 | 12/1992 |
| D358,200 S | 5/1995 | Cerola | | WO | WO93/17733 | 9/1993 |
| 5,431,676 A | 7/1995 | Dubrul et al. | | WO | WO94/13335 | 6/1994 |
| 5,447,494 A | 9/1995 | Dorsey, III | | WO | WO94/19030 | 9/1994 |

| | | |
|---|---|---|
| WO | WO94/23773 | 10/1994 |

OTHER PUBLICATIONS

KLI DeCherney Hysteroscopy Pump believed published before Apr. 19, 1993.

Marlow—Unique Products for Advanced Operative Laparoscopy 790-5M.

Select One-™ Minimal Access Surgery System, Introducing theVAC-™ Handcontrolled Suction Irrigation Instrument, ConMed Aspen Surgical Systems, Conmed Jul. 1992, 10M.

Select One-™ Minimal Access Surgery System, The Modular Instrument System for Surgical Endoscopy, SelectOne System, by ConMed, Aspen Surgical Systems believed published before Apr. 19, 1993.

Davol—Endo-Flo™ Irrigator, Bard, Davol Inc. ; instruction booklet #041002-0, 9011R, Nov. 1990.

Count On Us (Introducing Over 100 Precision Crafted Quality Endosurgery Instruments), Davis+Geck, 1993.

Essar® Suction Irrigator, Why do I need the *Essar* Suction Irrigator? Stewart Research, Inc. believed published before Apr. 19, 1993.

"Simultaneous pulsatile lavage and/or irrigation with suction . . . ", Pulsatile Lavage Debridement System, brochure No. 82-010-5150-0146/2.5M CISS Zimmer, Inc., Snyder Labs Inc, 1982.

Nezhat-Dorsey™ Hydro-Dissection™ Information Booklet Installation/Operating Instructions for "Quick-Disconnect" Probe Tips (2 sheets) believed published before Apr. 19, 1993.

Suction/Irrigator Is No Longer An Issue, Hydro-Dissection System, 556529 PP ICM Jul. 1992, Karl Stroz Gmbh & Co. Tuttlengen, West Germany.

A Fully Integrated Laparoscopic Irrigation and Instrumentation System, Cabot Medical, Langhorne, PA Apr. 1992, 10M, L/T (4 sheets).

Advances In Pelviscopy, The Irrigation Pump System, Cabot Medical, Langhorne, PA Apr. 1990 (3 sheets).

InteliJET™, Fluid Management System User's Manual, Smith & Nephew Dyonics Inc., copyright 1992, PN1060170.

Davol, Arthro-Flo®, Instructions For Use, 038657-0 901R C.R. Bard, Inc. Cranston RI, Jan. 1990.

Davol, Arthro-Flo High-Flo Irrigator, Bard, OP-AF0015000 Aug. 1992 5M C.R. Bard Inc. Cranston, RI.

3M Fluid Control System, For Precise Control of all Arthroscopic Procedures, 70-2008-5458-9, 1992 3M.

Davol, Instructions for Use, Simpulse-™ Suction/Irrigator, BARD, 034089-0 (2 sheets) Jan. 1985.

"Introducing the multi-functional instrument for virtually every laparoscopic case", USSC, Auto Suture Company, Copyright 1992, 556529 PP, 10M Jul. 1992.

Davol's Answers to Plaintiff's First Set of Interrogatories dated Jan. 7, 1996.

Davol's Supplemental Answers to Plaintiff's First Set of Interrogatories dated Feb. 14, 1997.

Deposition of Roger E. Darois, pp. 1-177, with index pp. 1-19 and correction and signature papers 1-3, dated May 7, 1997.

Rule 26 (a) (2) Expert Report of Dr. Harrith M. Hasson Relating to Davol's Defenses to Stryker's Infringement Claims Under the '402 Patent dated Oct. 29, 1997 including Exhibits A-D.

Rule 26 (a) (2) Expert Report of Roger E. Darois Relating to Davol's Defenses to Styrker's Infringement Claims Under the '402 Patent dated Oct. 30, 1997 including Exhibits A-D.

Rule 26 (a) (2) Rebuttal Expert Report of Dr. Harrith M. Hasson, M.D. Relating to Stryker's Infringement of United States Patent No. 5 391 145 and United States Patent No. 5 586 977 dated Dec. 8, 1997.

Deposition of Harrith M. Hasson, pp. 1-281 with index pp. 1-32 dated Feb. 13, 1998.

Davol's Supplemental Answers to Plaintiff's First Set of Interrogatories dated Feb. 14, 1997.

Ruling on Claim Construction Disputes dated Apr. 24, 1998.

Trial-vol. IV, Nov. 17, 1998: (Hope-Cross; Darois-direct, voir dire, Cross) multi-channel fiber-optic rotary multipage 35-43 (actual pp. 524-785).

Trial-vol. V, Nov. 18, 1998 (Darois-direct) multipage 623-785; actual pp. 3-44.

Memorandum Opinion and Order Denying Motion for Judgment as a Matter of Law dated May 26, 1999.

Arthur D. Little (Tsals) Dec. 8, 1992 letter to Davol.

Bard (Brad Cilley) Oct. 16, 1992 fax to John Skreenock.

Arthur D. Little (Tsals) Nov. 12, 1992 fax to John Skreenock (Davol).

Arthur D. Little (Tsals) Dec. 17, 1992 letter to John Skreenock.

Arthur D. Little (Tsals) Jan. 28, 1993 letter to John Skreenock.

Saline Pump Development Program, Davol Inc., Jan. 18, 1993, Cambridge, MA.

Teltech Nov. 2, 1992 search for John Skreenock re Scroll Pumps.

Arthur D. Little (Sword) Sep. 8, 1992 letter to Albert Solis.

Davol (Silva) Jan. 4, 1993 letter to Arthur D. Little.

Saline Scroll Pump Development Program.

Scroll Technology in Medical Products.

Hydroflex™ Irrigation Pump, DEKA website page dated May 10, 2006 (1 page).

\* cited by examiner

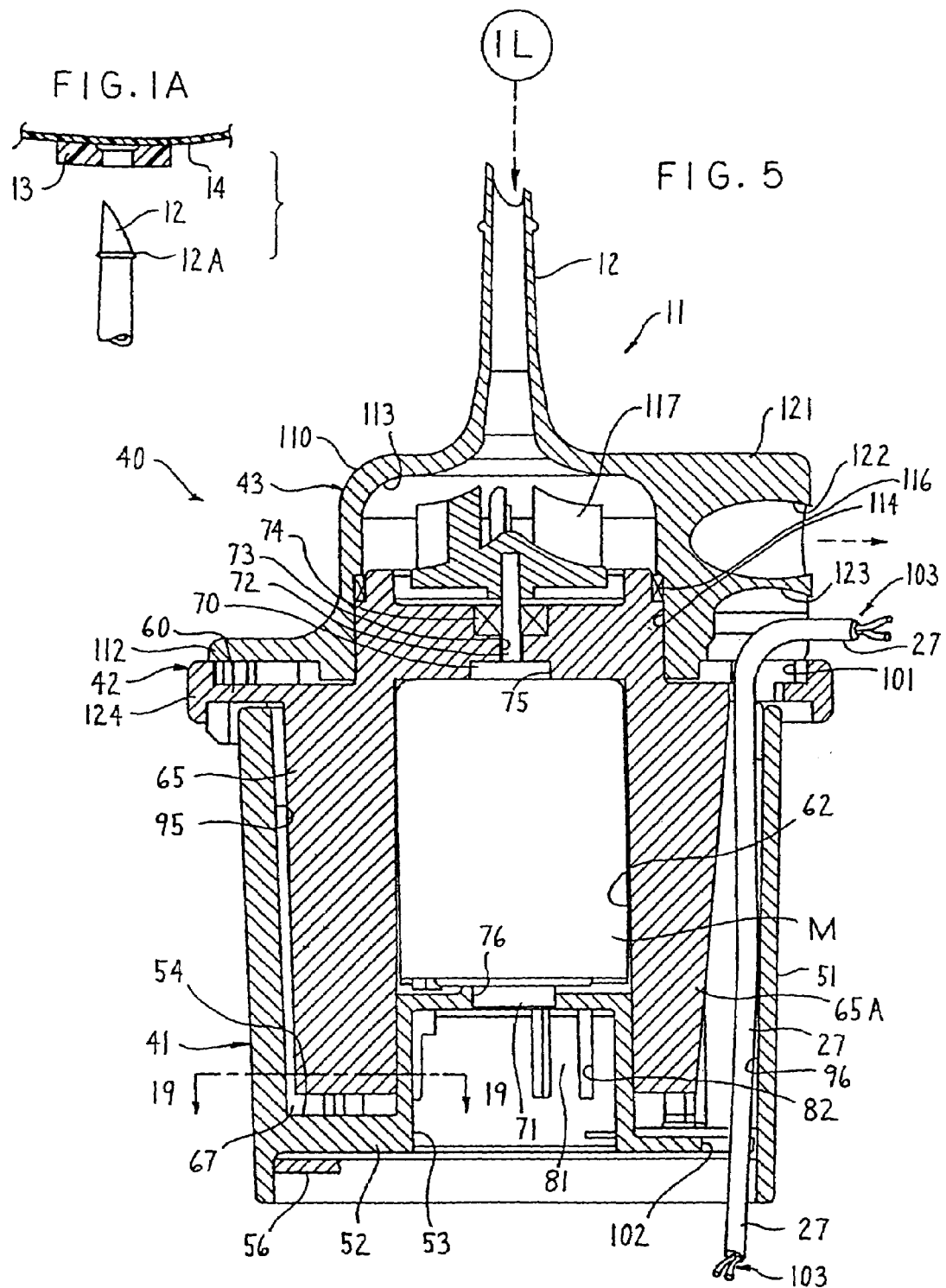

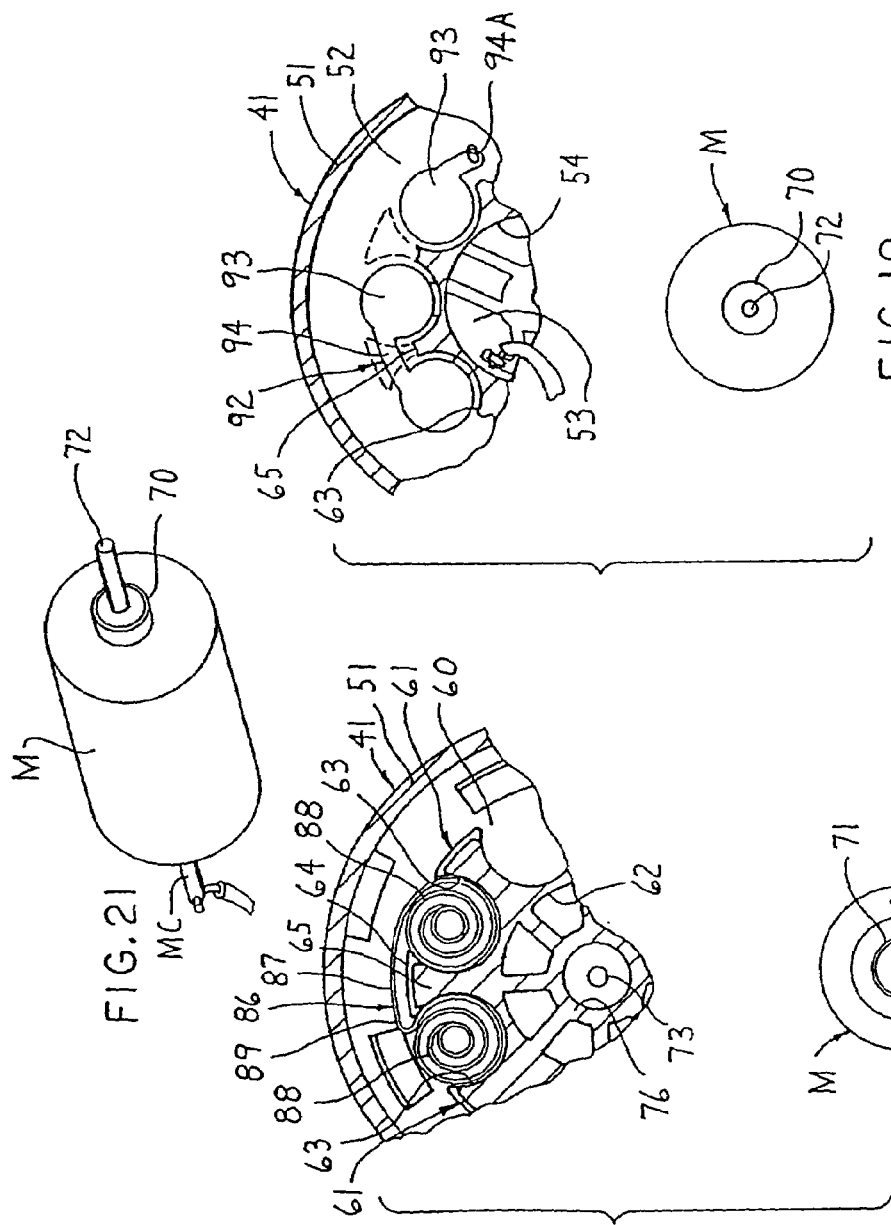

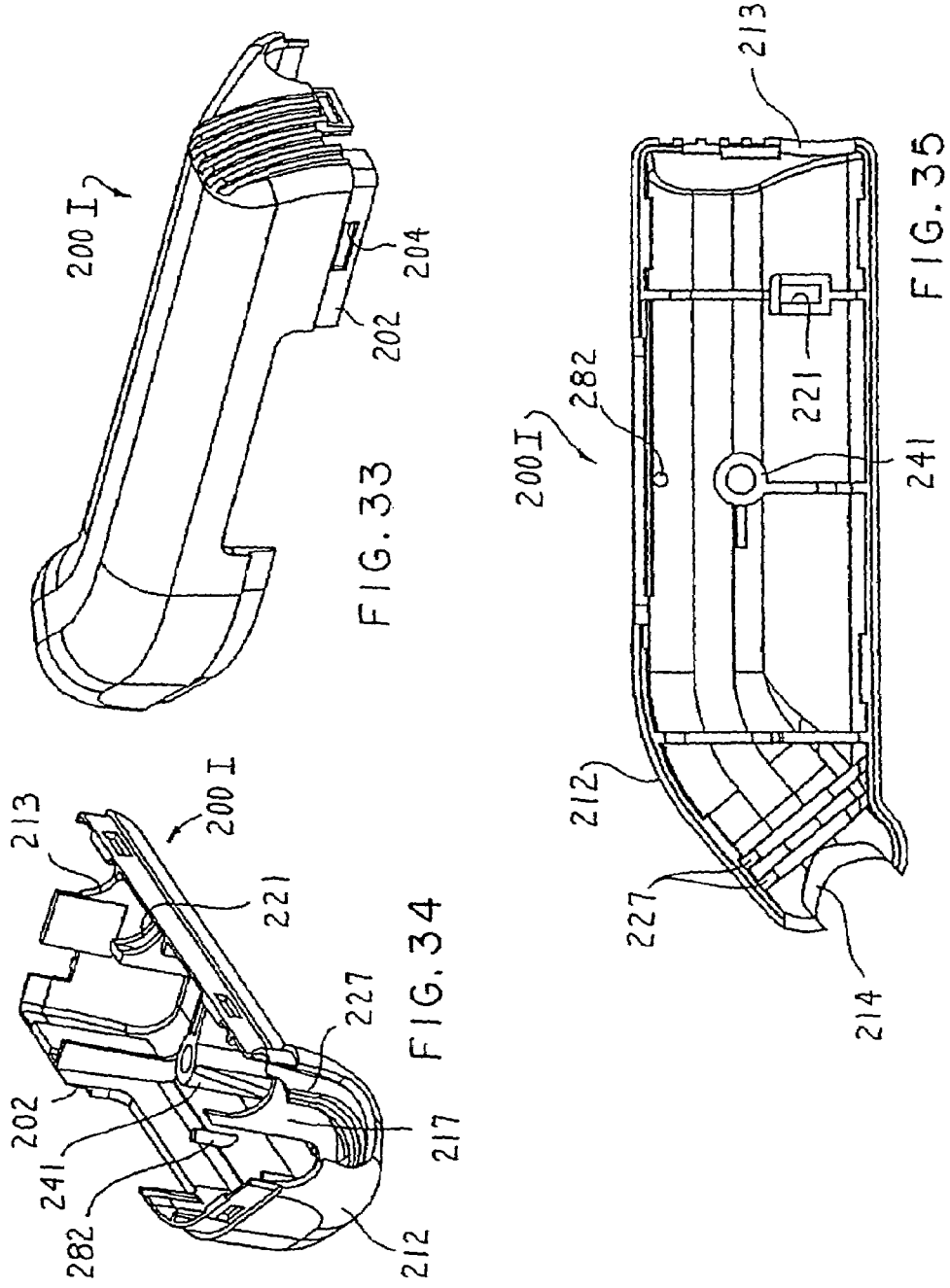

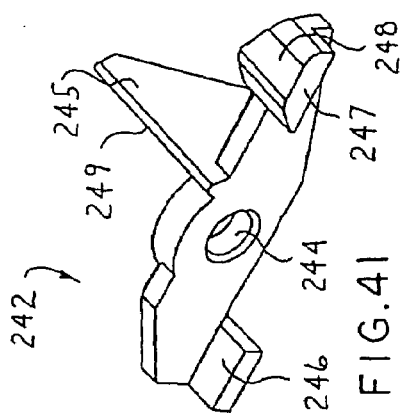
FIG. 41
FIG. 40
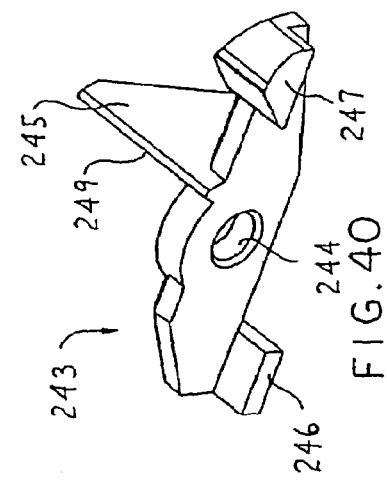
FIG. 39
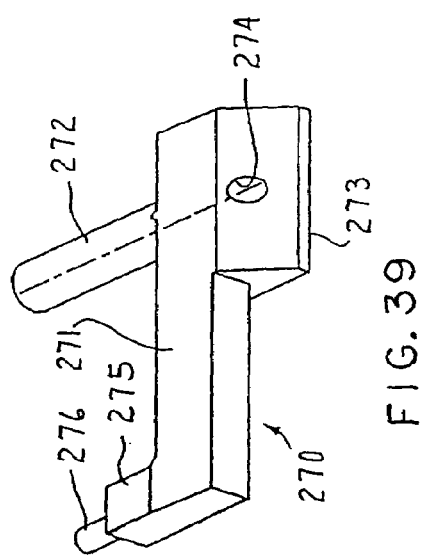
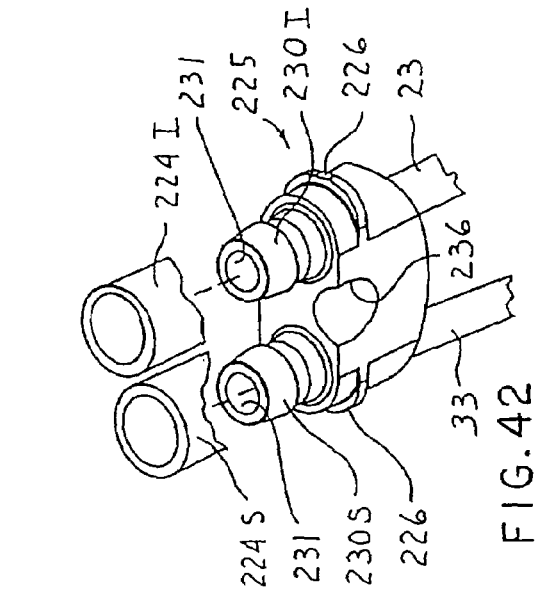
FIG. 42
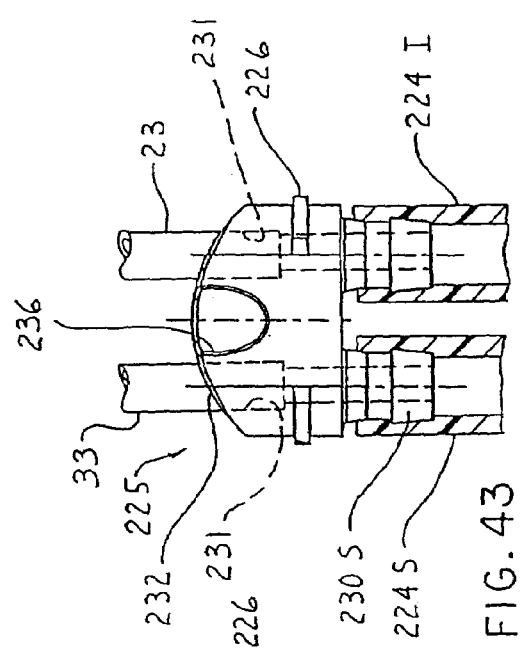
FIG. 43

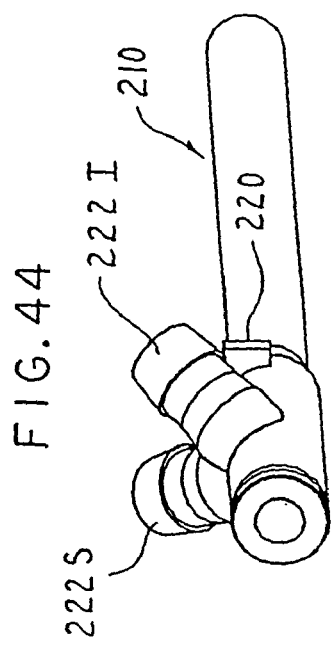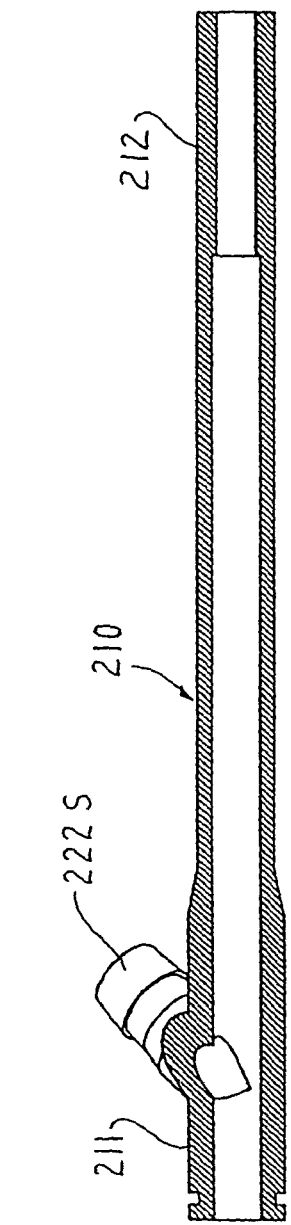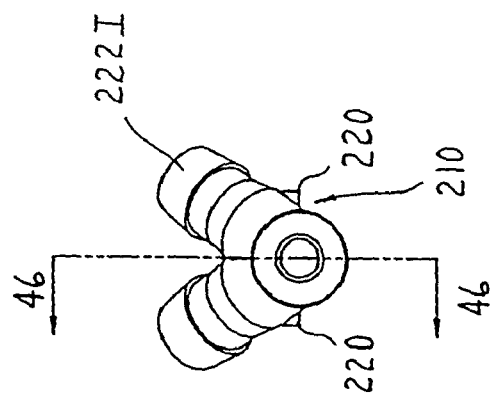

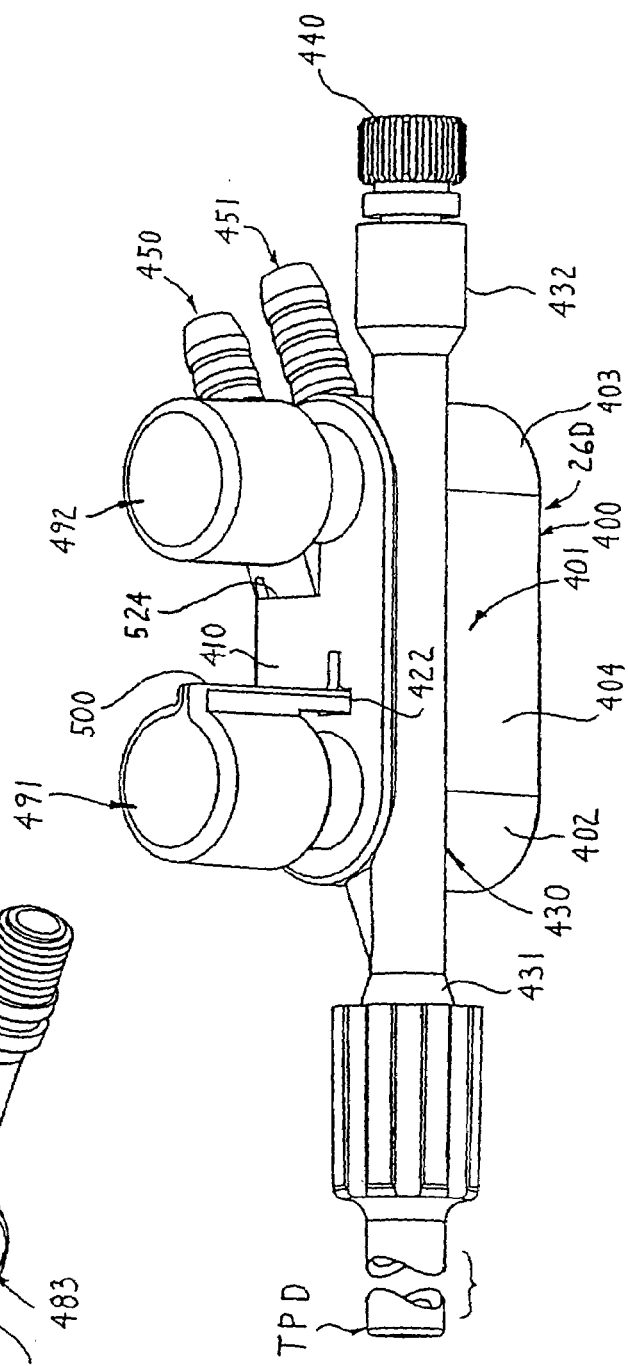
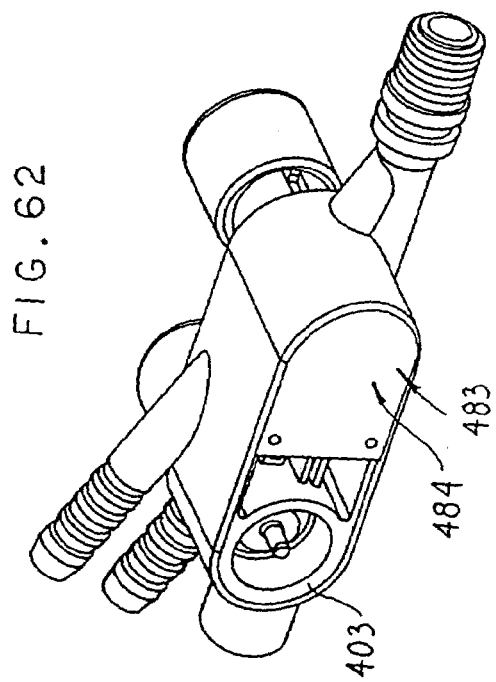

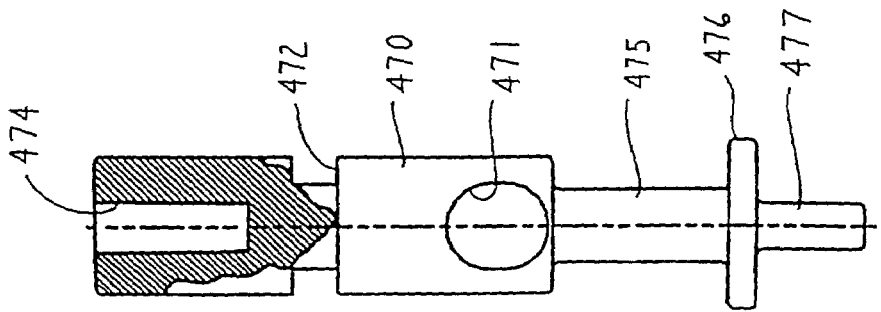
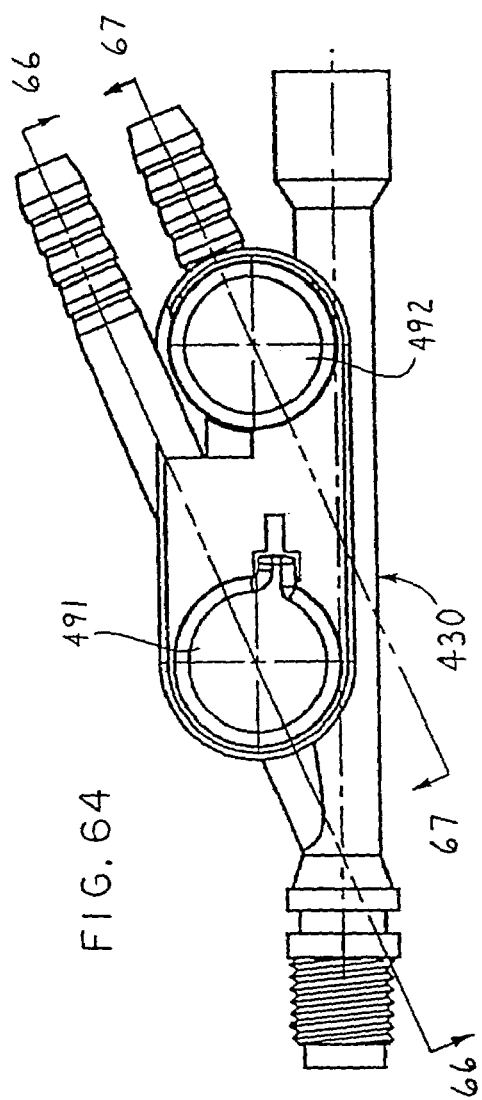
FIG. 64
FIG. 65

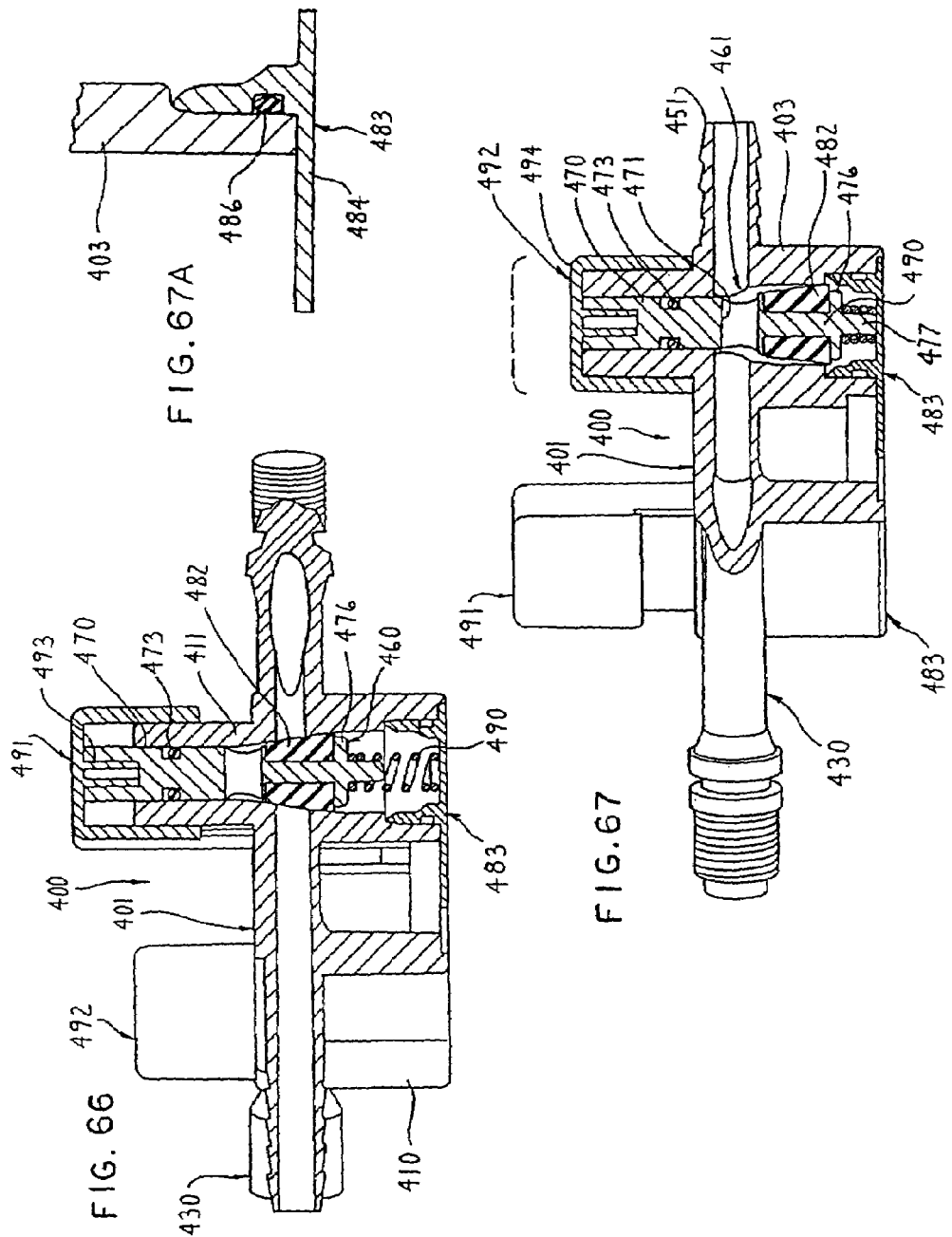

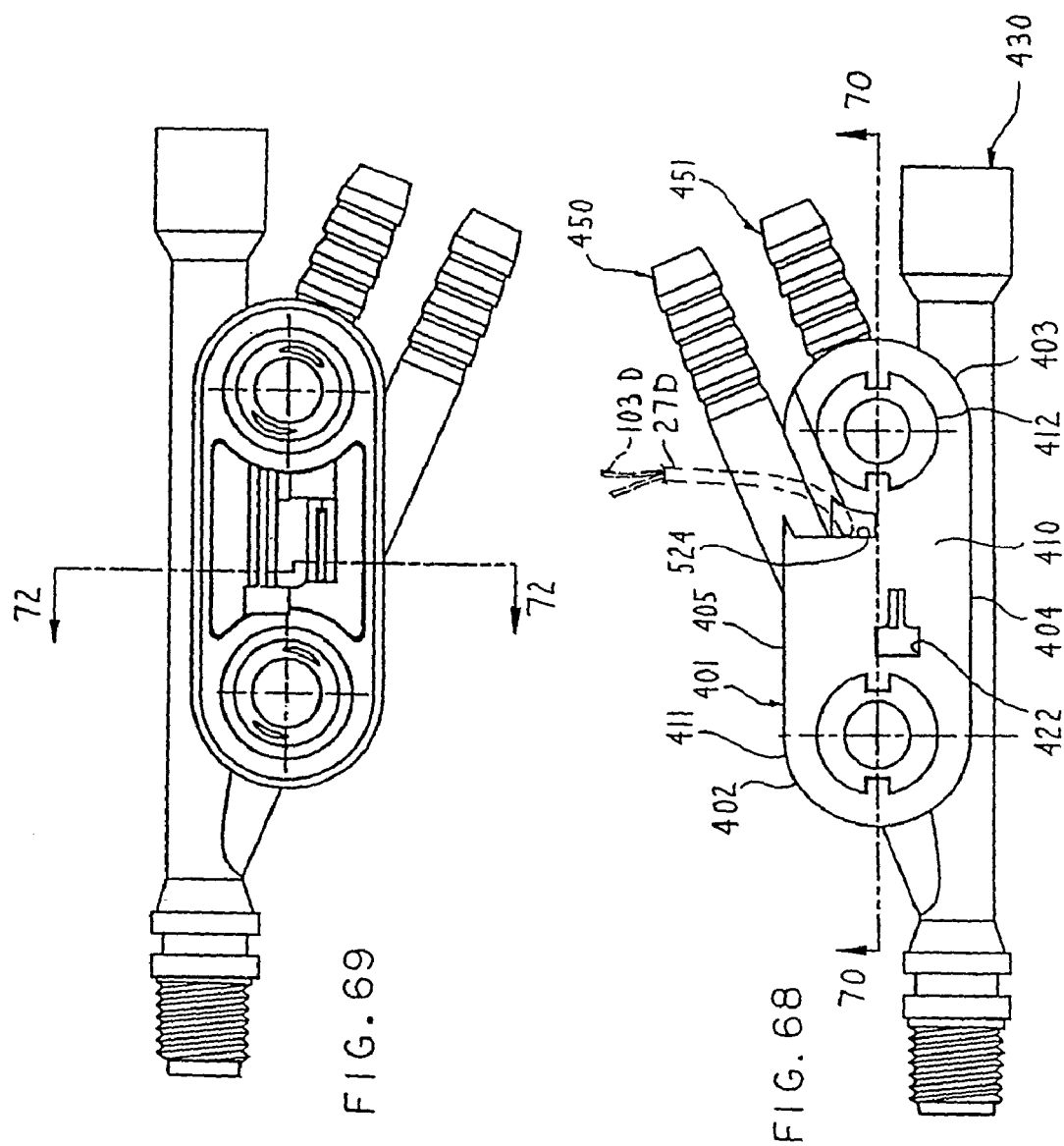

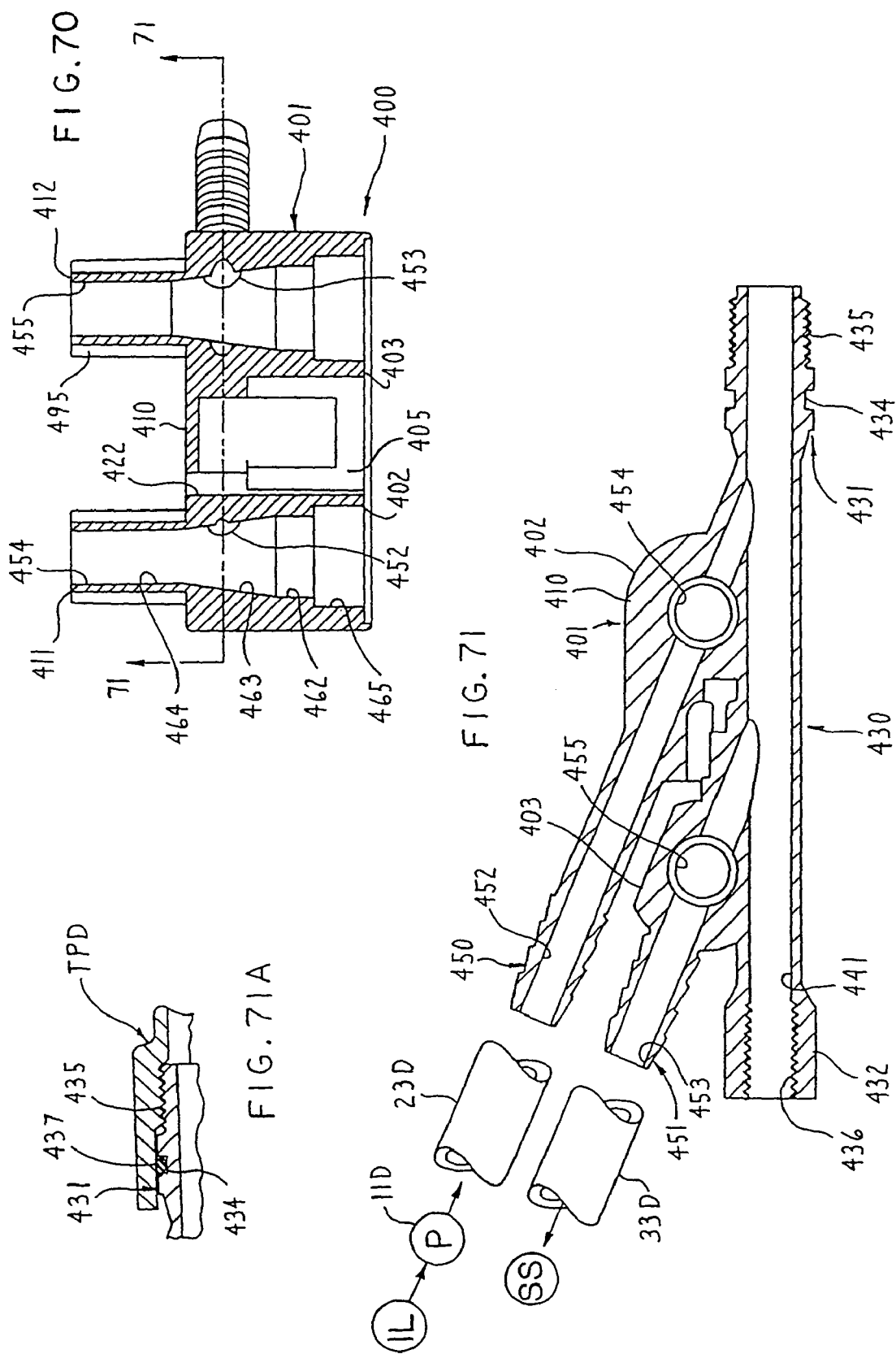

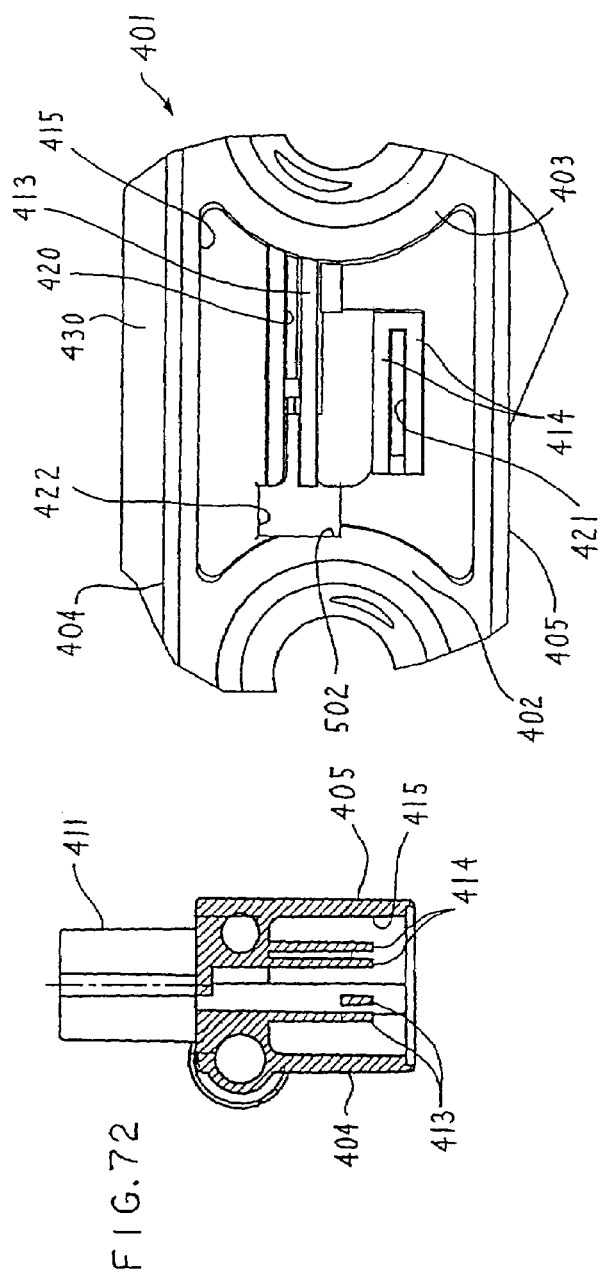
FIG. 72
FIG. 73
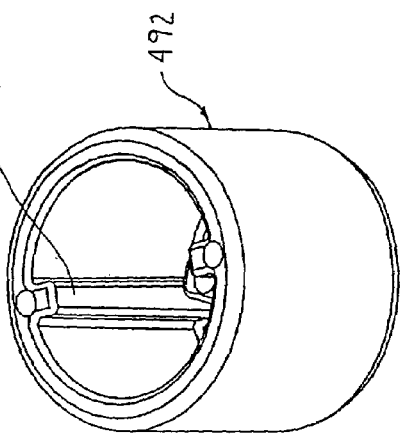
FIG. 74
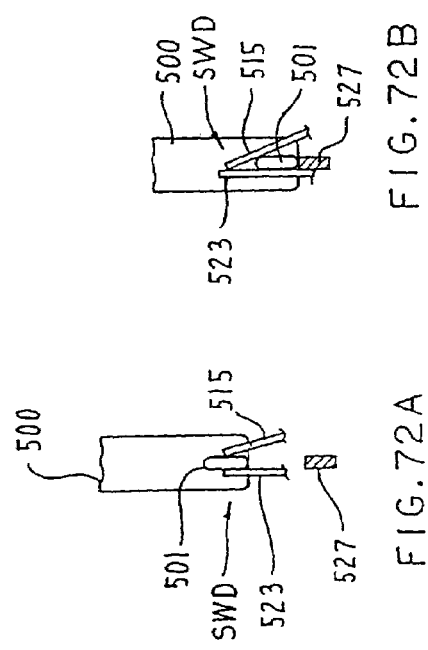
FIG. 72A
FIG. 72B

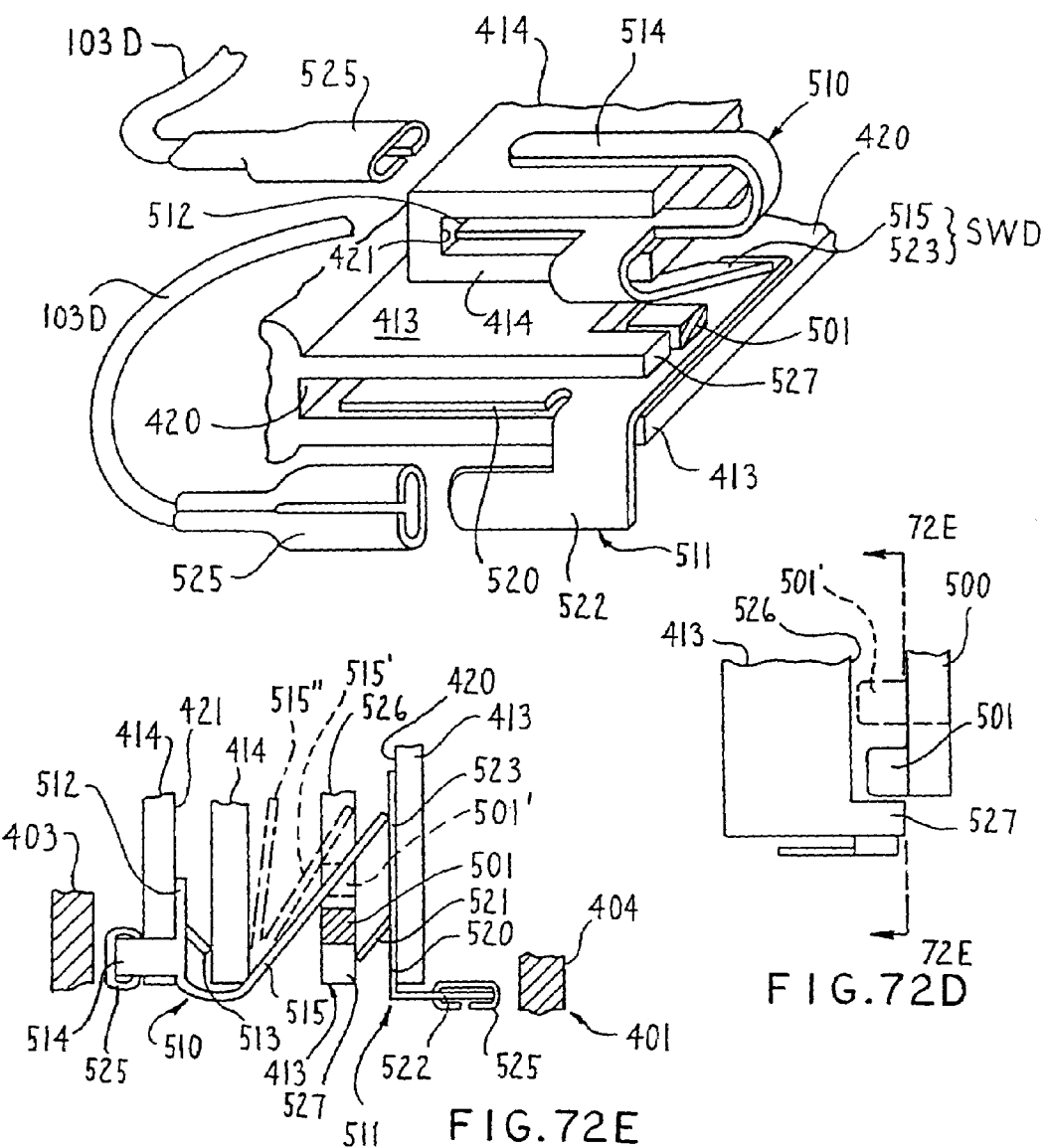

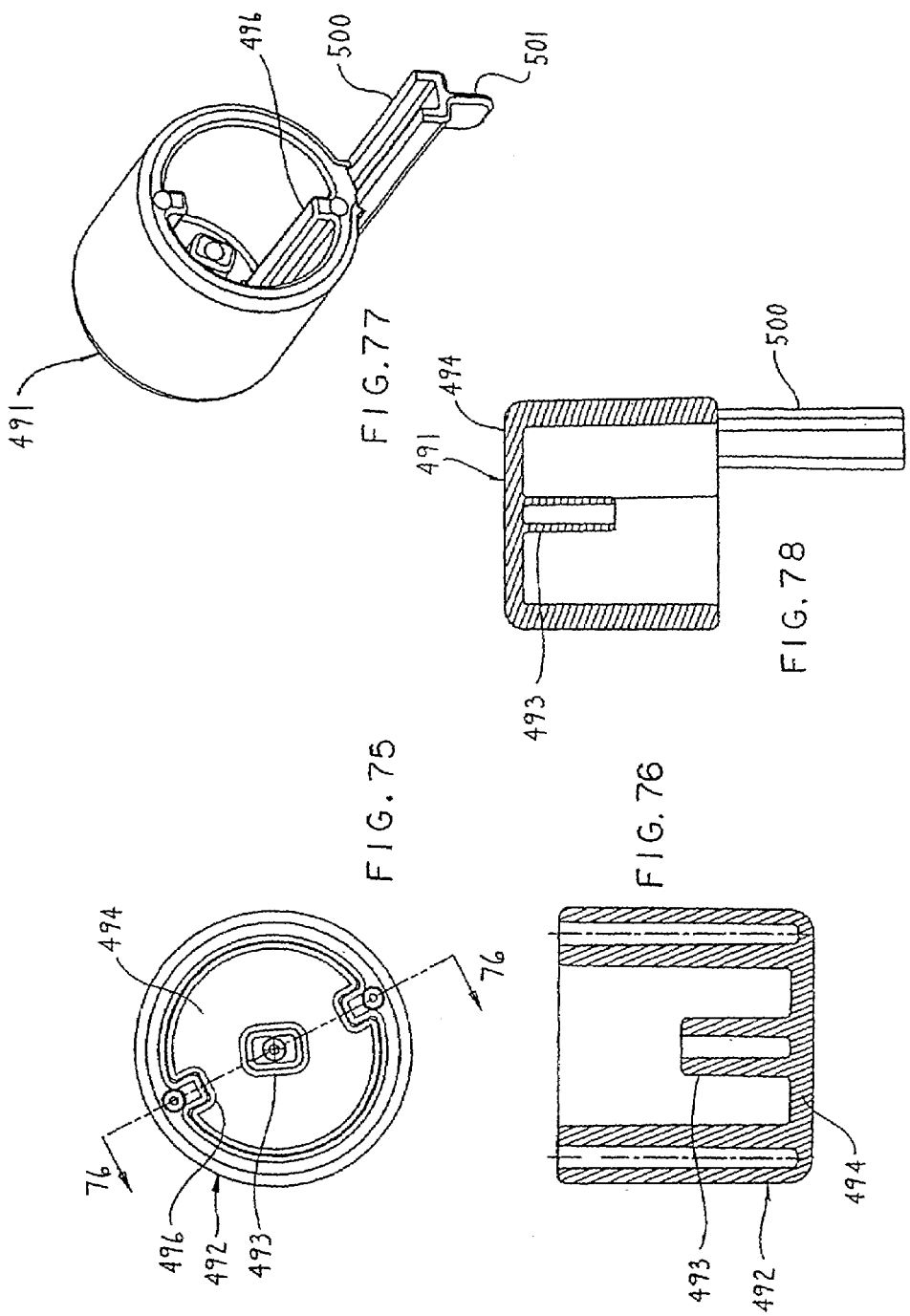

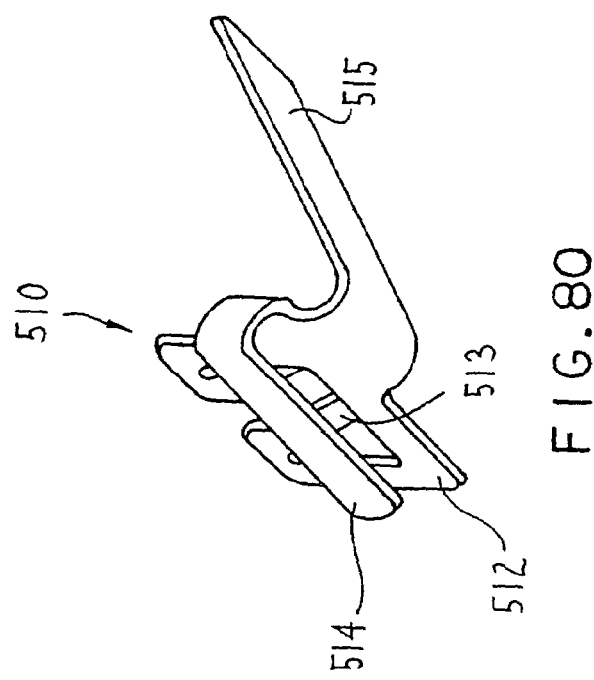
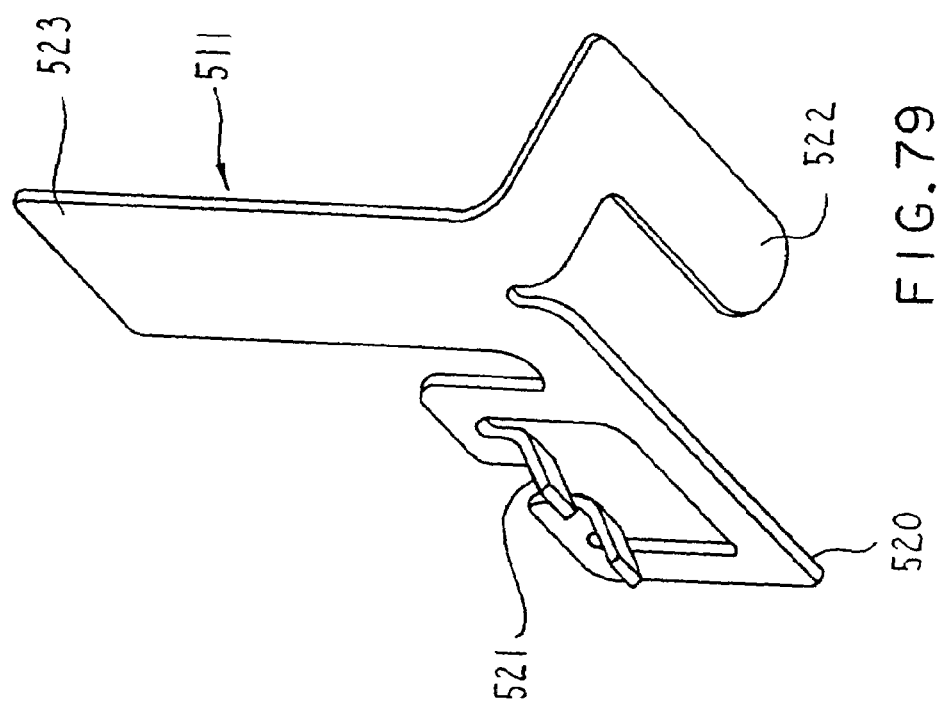

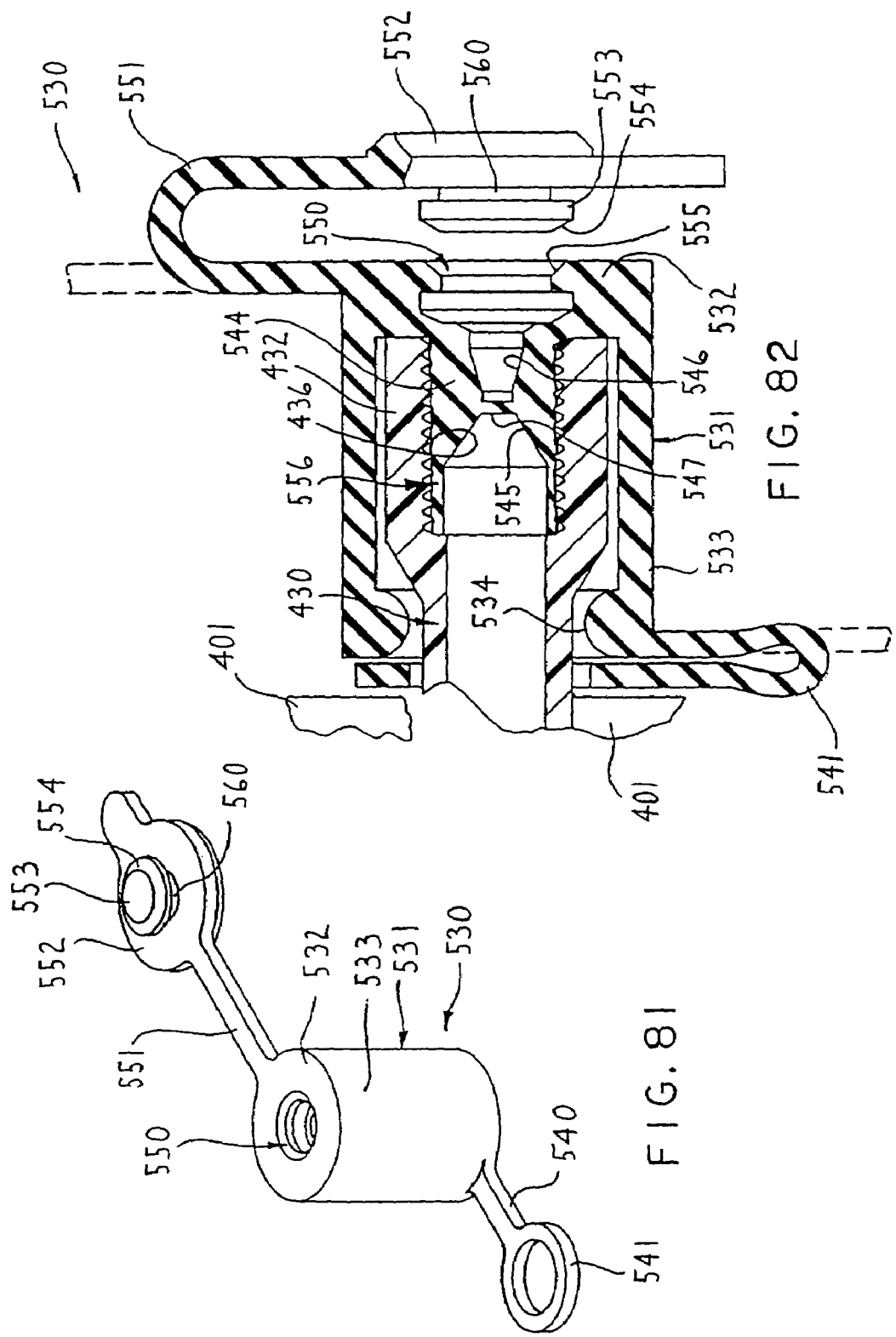

SURGICAL SUCTION IRRIGATOR

This application is a continuation of Ser. No. 09/676,517 filed Oct. 2, 2000 now U.S. Pat. No. 6,623,445, which is a continuation of Ser. No. 08/769,428, filed Dec. 19, 1996 now U.S. Pat. No. 6,213,970, which is a continuation of Ser. No. 08/502,708, filed Jul. 14, 1995 now abandoned, which is a continuation-in-part of Ser. No. 08/176,130, filed Dec. 30, 1993, now U.S. Pat. No. 5,484,402.

FIELD OF THE INVENTION

This invention relates to a surgical suction and irrigation system, and more particularly to one adaptable for use in endoscopic surgery.

BACKGROUND OF THE INVENTION

Stryker Corporation, the assignee of the present invention, filed on Apr. 19, 1993, U.S. patent application Ser. No. 08/049,144 now U.S. Pat. No. 5,470,305, disclosing a suction irrigation system in which a handpiece is supplied with irrigation liquid through an elongate flexible tube, from a remote source. The system includes an electric motor drive pump powered by a battery pack and controlled by an electric switch. The electric switch is on the handpiece and the battery pack is fixed along the irrigation liquid tube between the handpiece and irrigation liquid source, at a point remote from the handpiece. An electric cable extends between the battery pack and handpiece and along the irrigation liquid tube. Such system is marketed under the trademark SURGILAV PLUS™

However, the SURGILAV PLUS™ system, while adaptable to a variety of surgical uses, was not specifically directed toward endoscopic surgery. Moreover, it differs structurally and operationally in a number of respects from the present invention.

A number of other companies market irrigation and suction irrigation systems. However, the present inventors have not found same to be entirely satisfactory for their purposes.

Therefore, in a continuing effort to improve on surgical suction irrigation systems, particularly endoscopic suction irrigation systems, the present invention has been developed.

Further objects and purposes of the present invention will be apparent to persons acquainted with apparatus of this general kind, upon reading the following description and inspecting the accompanying drawings.

SUMMARY OF THE INVENTION

A surgical irrigation system is suitable for endoscopic and other surgical procedures. A hand held handpiece has a forward protruding hollow tip for supplying irrigation liquid to a surgical site, a hand actuable control for controlling irrigation liquid flow to the tip, and an irrigation liquid inlet. A self contained pumping unit is locatable adjacent a source of irrigation liquid and remote from the handpiece. The pumping unit comprises a housing containing an outlet for irrigation liquid, a pumping member for pumping irrigation liquid through the outlet, a motor for driving the pumping member, and an electric battery assembly for energizing the motor. An elongate tube connects the pumping outlet to the handpiece irrigation liquid inlet for supplying pumped irrigation liquid to the handpiece.

BRIEF DESCRIPTION OF THE DRAWINGS

FIG. 1A is an enlarged fragmentary cross-sectional view of the bag fitting and pumping unit liquid inlet connector of FIG. 1.

FIG. 5 is a central cross-sectional view of the pressure liquid unit of FIGS. 1-4 taken on a diametral cutting plane running through the cable space and indicated generally by the line 5-5 in FIG. 3.

FIG. 19 is a fragmentary, somewhat schematic, sectional view generally as taken on the line 19-19 of FIG. 6 and showing a lower battery contact.

FIG. 20 is a fragmentary, somewhat schematic, sectional view generally as taken on the line 20-20 of FIG. 6 and showing an upper battery contact.

FIG. 21 is a pictorial view of the motor of FIG. 19.

FIGS. 33 and 34 are pictorial views of the irrigation side half shell of the FIG. 27 handpiece.

FIG. 35 is a side elevational view, taken from the inside, of the FIG. 33 half shell.

FIG. 39 is an enlarged pictorial view of the irrigation anvil of FIG. 29.

FIGS. 40 and 41 are pictorial views of the suction and irrigation pinch levers, respectively, of FIG. 29.

FIG. 42 is a pictorial view, taken substantially from the front, of the adapter block of FIG. 32.

FIG. 43 is a plan view taken from above and behind of the FIG. 42 adapter block.

FIG. 44 is a pictorial view of the conduit of FIG. 29.

FIG. 45 is a front view of the FIG. 44 conduit.

FIG. 46 is a central cross-sectional view of the FIG. 44 conduit.

FIGS. 53A and 53B are fragments of FIG. 53 with the irrigation hose added and shown in its closed and opened positions respectively.

FIGS. 56A and 56B are fragments of FIG. 56 with the suction tube added and shown in its closed and opened positions respectively.

FIG. 61 is a pictorial view of a modified handpiece embodying the invention, taken from the top and left side thereof.

FIG. 62 is a pictorial view of the FIG. 61 handpiece taken from the bottom and front thereof with one bottom plug removed.

FIG. 64 is a top view of the FIG. 61 handpiece.

FIG. 65 is an enlarged, partially broken, elevational view of a valve member of FIG. 63.

FIG. 66 is a sectional view substantially taken on the line 66-66 of FIG. 64.

FIG. 67 is a sectional view substantially taken on the line 67-67 of FIG. 64.

FIG. 67A is an enlarged fragment of a portion of the bottom right quadrant of FIG. 67.

FIG. 68 is a top view of the handpiece shell of FIG. 61.

FIG. 69 is a bottom view of the FIG. 68 handpiece shell.

FIG. 70 is a sectional view substantially taken on the line 70-70 of FIG. 68.

FIG. 71 is a sectional view of FIG. 70.

FIG. 71A is a fragment of the right end portion of FIG. 71 with the FIG. 61 tip and an intervening annular seal added and shown in central cross section.

FIG. 72 is a cross sectional view substantially taken on the line 72-72 of FIG. 69.

FIG. 72A is an enlarged fragment of FIG. 72 with the addition of fragments of the FIGS. 79 and 80 switch elements added and positioned in their "off" position.

FIG. 72B is of view similar to FIG. 72A with the switch parts in their "on" position.

FIG. 72C is an enlarged fragmentary pictorial view taken substantially from the same orientation as FIG. 62 with the bottom of the handpiece housing opened to show the FIGS. 79 and 80 switch elements in their installed position in the handpiece housing and in their switch "on" position.

FIG. 72D is an enlarged fragmentary elevational view taken generally from the orientation of FIG. 66 to show the switch opening and closing ridge in solid line in its switch "on" and in dotted lines in its switch "off" positions.

FIG. 72E is an enlarged fragmentary sectional view looking generally leftward from the right side of FIG. 72C or substantially on the line 72-12E of FIG. 72D and in solid lines showing the switch "on" and in dotted line the switch "off" conditions of the switch elements.

FIG. 73 is an enlarged fragment of FIG. 69 and showing more clearly the switch carrier plates which depend within the FIG. 61 handpiece housing.

FIG. 74 is an enlarged pictorial view, taken from the bottom and one side of the suction push button of FIG. 61.

FIG. 75 is a bottom view of the FIG. 74 push button.

FIG. 76 is a sectional view substantially taken on the line 76-76 of FIG. 75.

FIG. 77 is a pictorial view taken from the bottom and one side thereof of the irrigation liquid push button of FIG. 61.

FIG. 78 is a central cross sectional view of the FIG. 77 push button.

FIG. 79 is an enlarged pictorial view of one of the switch elements of FIGS. 63 and 72C and 72E.

FIG. 80 is an enlarged pictorial view of the other switch element.

FIG. 81 is a pictorial view of a cap unit usable an alternative to the closure plug for closing the rear of the conduit of FIG. 63.

FIG. 82 is an enlarged central cross sectional view of the FIG. 81 cap unit installed on the rear end portion of the conduit of the handpiece 26D of FIG. 63 in place of the above mentioned closure plug.

DETAILED DESCRIPTION

Figure 3:
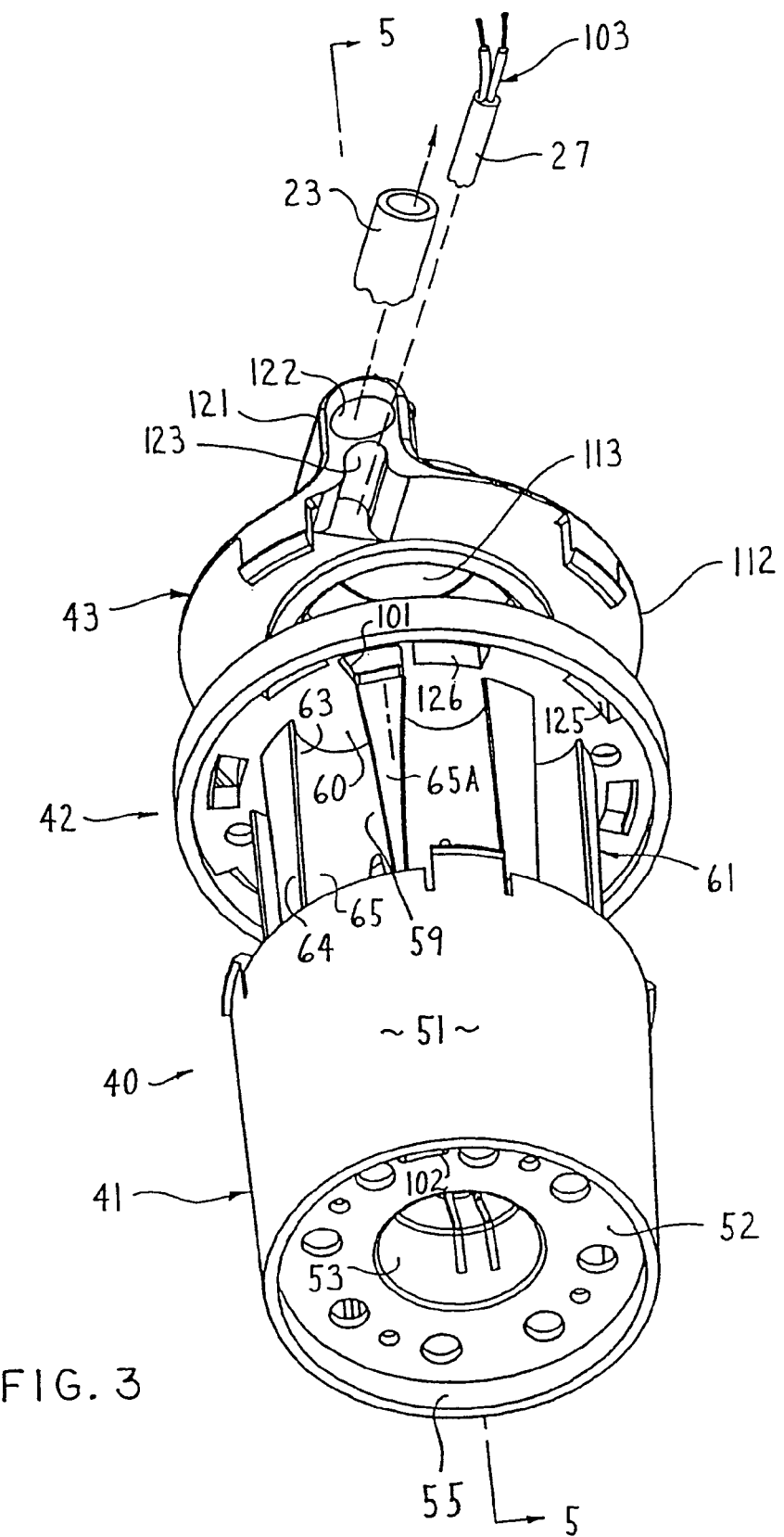

The suction irrigation system 10 (FIG. 1) embodying the invention comprises a pressure liquid unit 11 having a upstanding liquid inlet connector 12 for direct connection to a liquid outlet connector 13 on a conventional irrigation liquid supply IL. In the example shown in FIG. 1, the irrigation liquid supply IL is a conventional irrigation liquid supply bag 14 and the connector 13 is a conventional luer connector. As here shown, the irrigation liquid bag 14 may be conventionally supported by the usual horizontal arm 15 adjustably fixed on the usual standing pole 16, the arm and pole being, for example, of the kind usually employed to support an IV (intravenous) bottle, irrigation liquid bag, or the like. The pressure liquid unit 11 may be supported from the bag 14 simply by interconnection of the respective connectors 12 and 13. Alternately, additional support means may be employed, such as a strap (not shown) fixed in any convenient way to the outside of the pressure liquid unit 11 and to the arm 15. Alternatively, the pressure liquid unit 11 may be supported by a conventional bracket 18 conventionally clamped at 19 to the pole 16, and encircling the pressure liquid unit 11 snugly, as indicated generally at 20. The pressure liquid unit 11 pressurizes irrigation liquid tube 23 (FIG. 3) which is flexible and runs at length (for example 6-12 feet) to a handpiece 26 to be gripped and controlled by a user, typically a surgeon or surgical assistant. An electric cable 27 is comparable in length to the tube 23 and runs with it from the pressure liquid unit 11 to the handpiece 26. The cable 27 preferably is, for neatness, fixed along the tube 23, for example by longitudinally spaced conventional clips 32 or longitudinal bonding. A flexible suction tube 33 runs from the handpiece 26 to a conventional suction source SS, such as a conventional hospital operating room suction port. The tubes 23 and 33 and cable 27 preferably run to the rear end portion 34 of the handpiece 26. The handpiece 26 in the embodiment shown has a rigid tubular tip TP (hereafter described) releasably extending forward from the front end portion 36 thereof for direction toward a surgical site, either directly or through a conventional endoscopic cannula (a fragment of which is schematically indicated at CA in FIG. 1), for performing irrigation and suction removal of debris at a surgical site SU.

Pressure Liquid Unit 11

Figure 2:
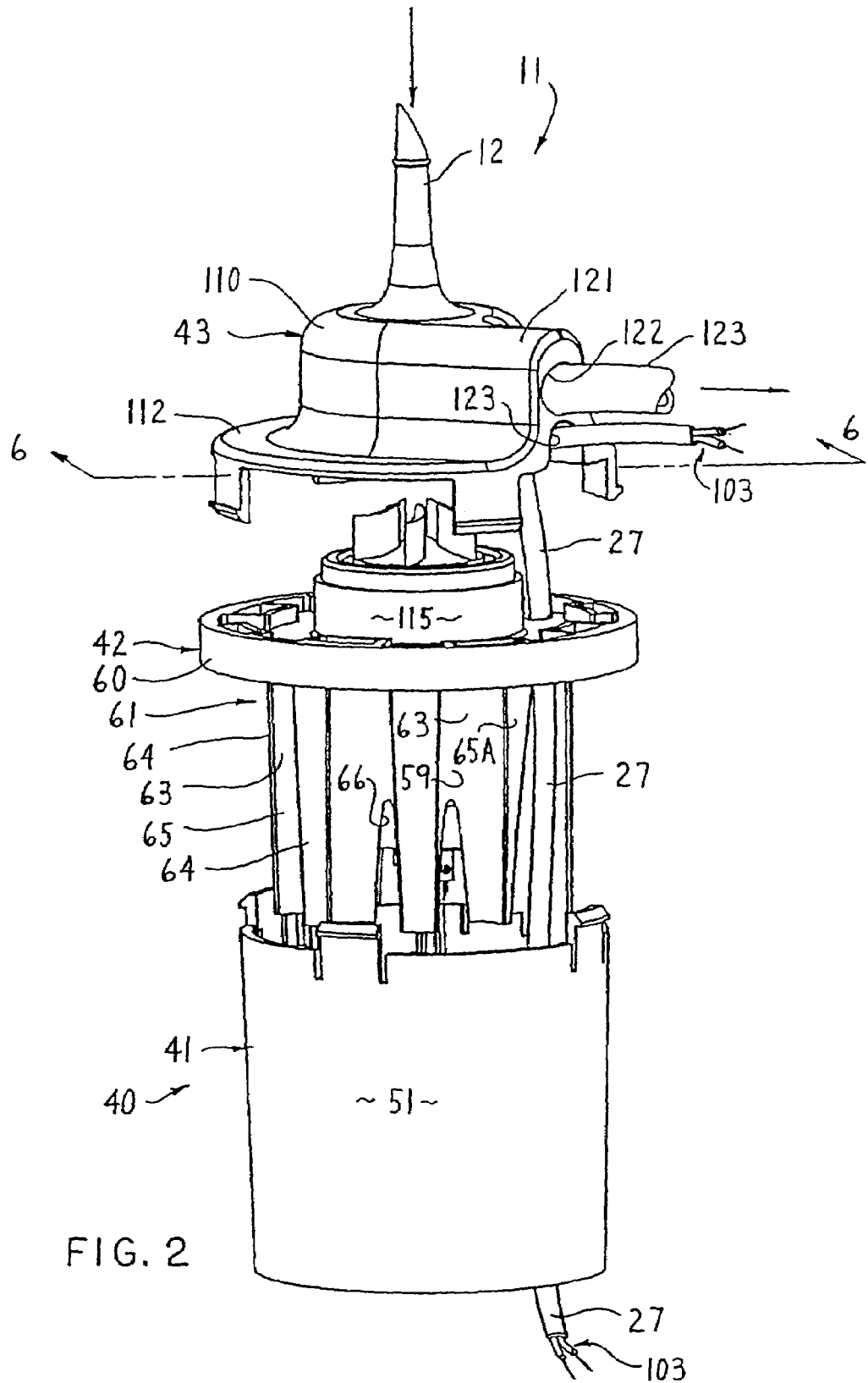
FIGS. 2-4 are exploded pictorial views of the pressure liquid unit of FIG. 1 taken from three different vantage points of differing height and circumferential location.

The pressure liquid unit 11 comprises (FIG. 2) a housing generally indicated at 40, in turn comprising an upward opening cup 41, a motor and battery locator 42 and a pump cover 43.

The cup 41 comprises an open top 50 (FIGS. 7-9), a slightly downward tapered side/wall 51 and a generally closed bottom wall 52. The bottom wall as an upstepped central motor support drum 53. The drum is of circular cross-section. An annular, upward facing, battery receiving groove 54 is defined radially and coaxially between the cup side wall and drum.

The battery and motor locator 42 (FIGS. 6 and 13) comprises a deck 60 adapted to seat upon the top edge of the cup side wall 51 and substantially close the open top of the cup 41. A finned column 61 fixedly coaxially depends from the deck 60. The column comprises a hollow tubular wall 59 defining a downward opening recess 62 located coaxially therein and closed at its top by the deck 60. The finned exterior of the column 61 is defined by a plurality (here eight for example) of circular cross-section grooves 63 extending the length of the column. The grooves 63 are circumferentially evenly spaced and circumferentially separated by axial, curved cross-section, ridge-like fins 65 radially outwardly extending from the tubular wall 59. The radially outermost surface 64 of the column is somewhat tapered downward in correspondence to the taper of the sidewall 51 of the cup. The circular cross-section grooves 63 have axes similarly convergent downward toward the central axis of the locator 42 (and thus toward the central axis of the recess 62 and deck 60). The grooves 63 thus have bottom portions which cut into the recess 62 at the arched notches 66. The column 61 is sized to depend snugly into the cup 41, with the deck 60 mounted atop the side wall 51 of the cup. In this installed position, the bottom of the hollow column 61 extends down into the annular groove 54 between the drum and side wall of the cup and the drum 53 is snugly but slidably received upward into the bottom portion of the central recess 62 of the locator. With the locator 42 installed in the cup 41, the fins 65 have their bottom ends 67 (FIGS. 5 and 6) spaced above the bottom wall 52 of the cup 41.

The locator 42 and cup 41, when assembled, are intended to locate therewithin in a circumferential array, plural (here eight) conventional AA batteries B (FIGS. 17 and 18), one in each of the circumferentially distributed grooves 63 of the locator, and a battery powered motor M in the recess 62.

Figure 7:
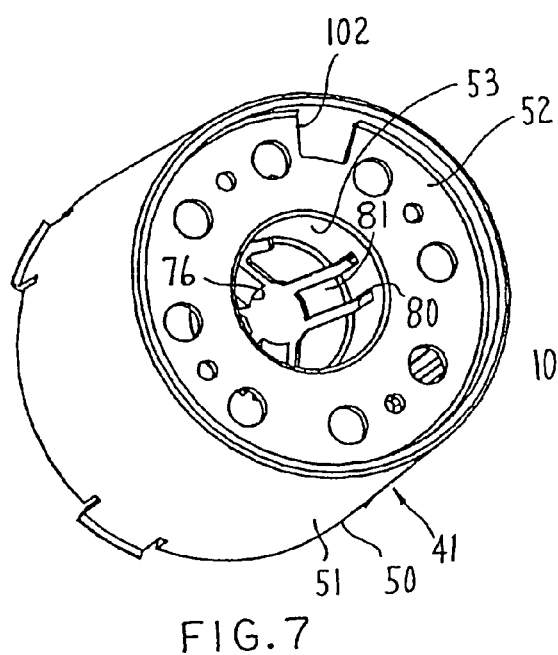
FIGS. 7-9 are pictorial views of the cup of FIGS. 2-6, taken from different viewpoints, to show the bottom of the cup in FIG. 7 and to show different viewpoints of the interior of the cup in FIGS. 8 and 9.
Figure 8:
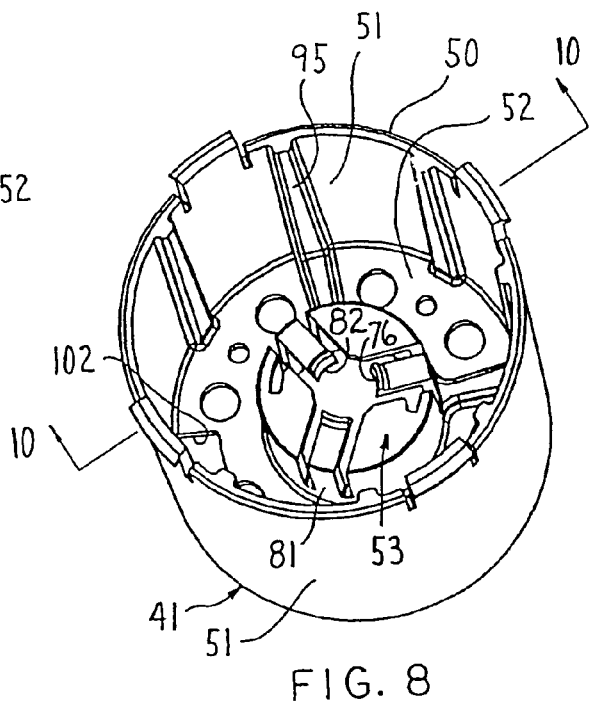
Figure 9:
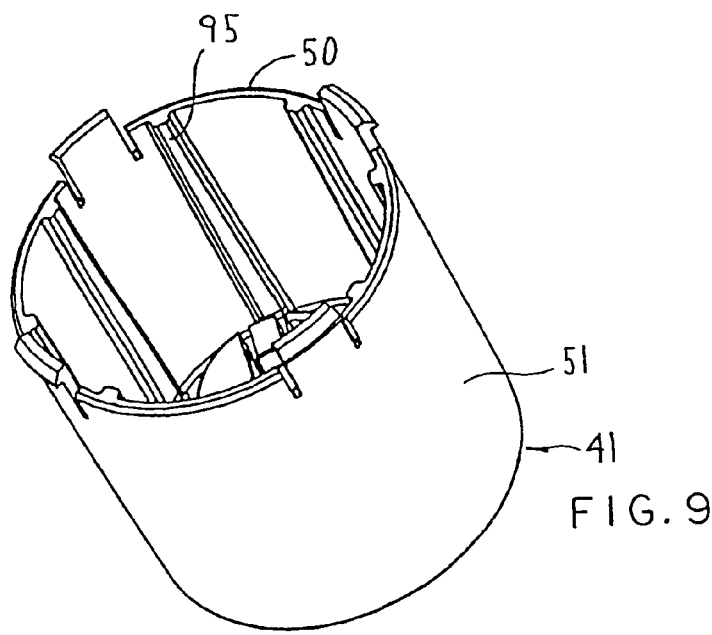

The motor M is, in the embodiment shown, shaped generally as a right circular cylinder with coaxially protruding top and bottom bosses 70 and 71. A shaft 72 extends coaxially up through the top boss 70 and is rotatable with respect thereto. See particularly FIGS. 5 and 21. The motor M is snugly but slidably received up into the recess 62 of the locator 42 with its shaft 72 extending up through a coaxial hole 73 in the deck 60. A conventional annular seal 74 (FIG. 5) recessed in the top of the deck 60, admits the shaft 72 rotatably upwardly therethrough but prevents liquid leakage therepast downward along the shaft toward the top of boss 70. The motor M is coaxially located in the recess 62 by snug reception of its top boss 70 in a down facing central recess 75 in the deck 60, and its bottom boss 71 in a central opening 76 in the top of the drum 53 (FIGS. 7 and 8).

Figure 10:
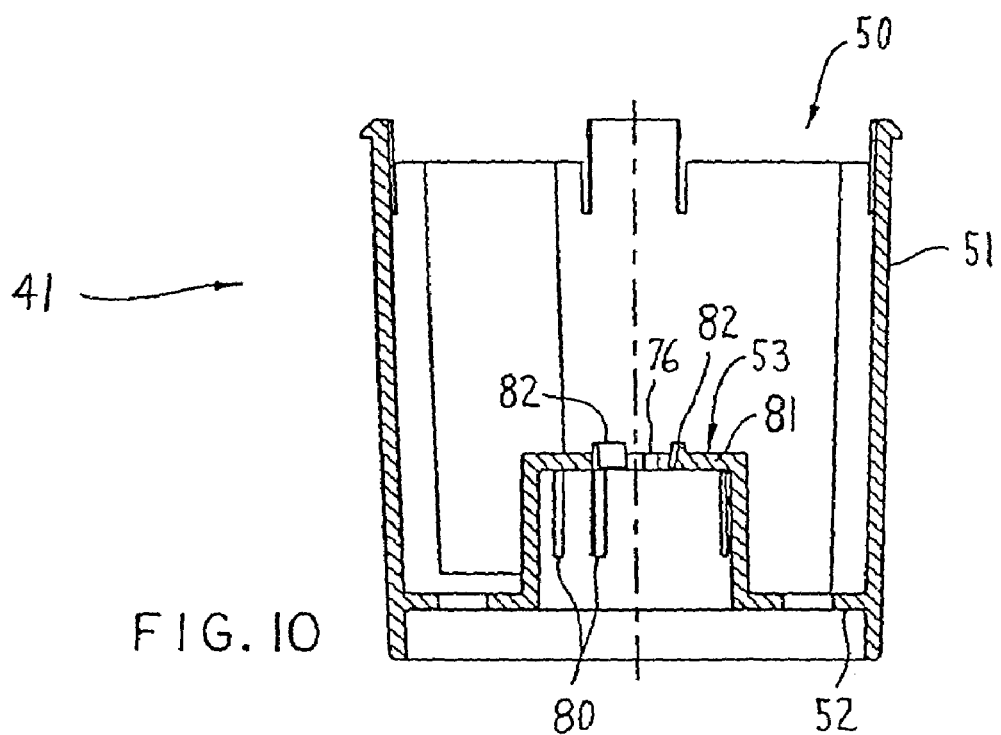
FIG. 10 is a central cross-sectional view of the cup, substantially as taken on the line 10-10 of FIG. 8.

The top and sides of the drum 53 are cut by three evenly circumferentially spaced pairs of parallel slots 80 communicating with the central opening 76. The parallel slots 80 of each pair define therebetween a generally L-shaped segment 81 of the drum top and side walls. The upper and radially inner ends of the three segments 81 are enlarged in cross-section to define corresponding circumferentially spaced rim parts 82 which together define the central opening 76 through the top of the drum. As seen in FIG. 10, the rim parts 82 are slightly wedge-shaped, to converge downwardly slightly and thereby tend to center therebetween, in wedging fashion, the bottom boss 71 of the motor M. The L-shaped segments 81, being separated from the rest of the drum 53 by the flanking slots 80, can resiliently deflect, in the manner of a leaf spring, to snugly grip the bottom boss 71 of the motor M and thereby firmly and fixedly center the motor M coaxially with respect to the cup 41 and locator 42.

Figure 14:
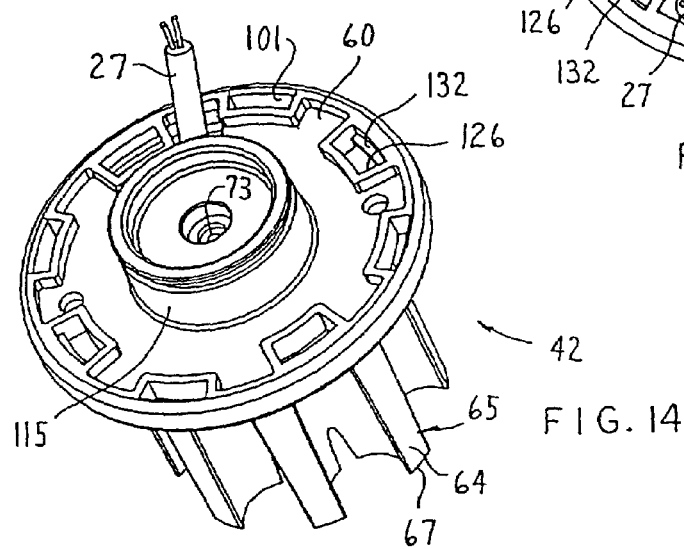
Figure 18:
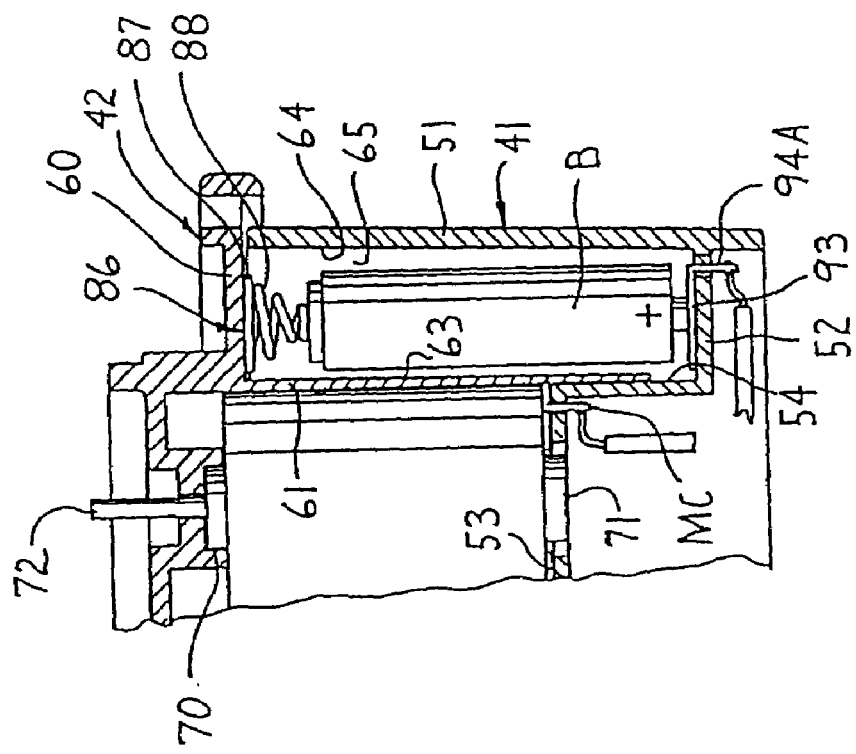
FIG. 18 is a somewhat schematic fragment of FIG. 6 showing location of the motor and battery in the locator of FIG. 13.

Electrically conductive spring wire, upper contacts 86 (FIGS. 16, 17, 18 and 20) each comprise a generally straight bight flanked by integral coil compression spring portions 88 of frustoconical profile. The profile of each coil spring portions 88 tapers downwardly as seen in FIGS. 17 and 18. The bight 87 and widened base of each spring portion 88 is backed by the underside of the deck 60. The coil spring portions 88 each are snugly frictionally gripped by the surrounding fins 65 to firmly hold each upper contact 86 axially against the underside of the deck 60. The upper contacts 86 are easily installed on the column 61 by placing same in registry with the bottom end 67 (FIG. 14) of the corresponding fin 65 and then sliding same there along upwardly into contact with the underside of the deck 60.

Conductive, flat plate, lower contacts 92 (FIGS. 16-19) each comprise a pair of circumferentially spaced circular disks 93 connected by an integral circumferentially extending strap 94. In one of the lower contacts 92, the strap 94 is cut in the middle to form respective terminal tabs 94A (FIGS. 17 and 19) for connection of the batteries B, in circuit with the motor M and a switch SW hereafter described. The disks 93 are respectively fixedly located coaxially with the grooves 63 of the column 61 but are spaced below the column 61 to lie fixedly atop the bottom wall 52 of the cup 41, within the annular groove 54 thereof. The disks 93 are fixed atop the cup bottom wall 52 by any convenient means.

Figure 12:
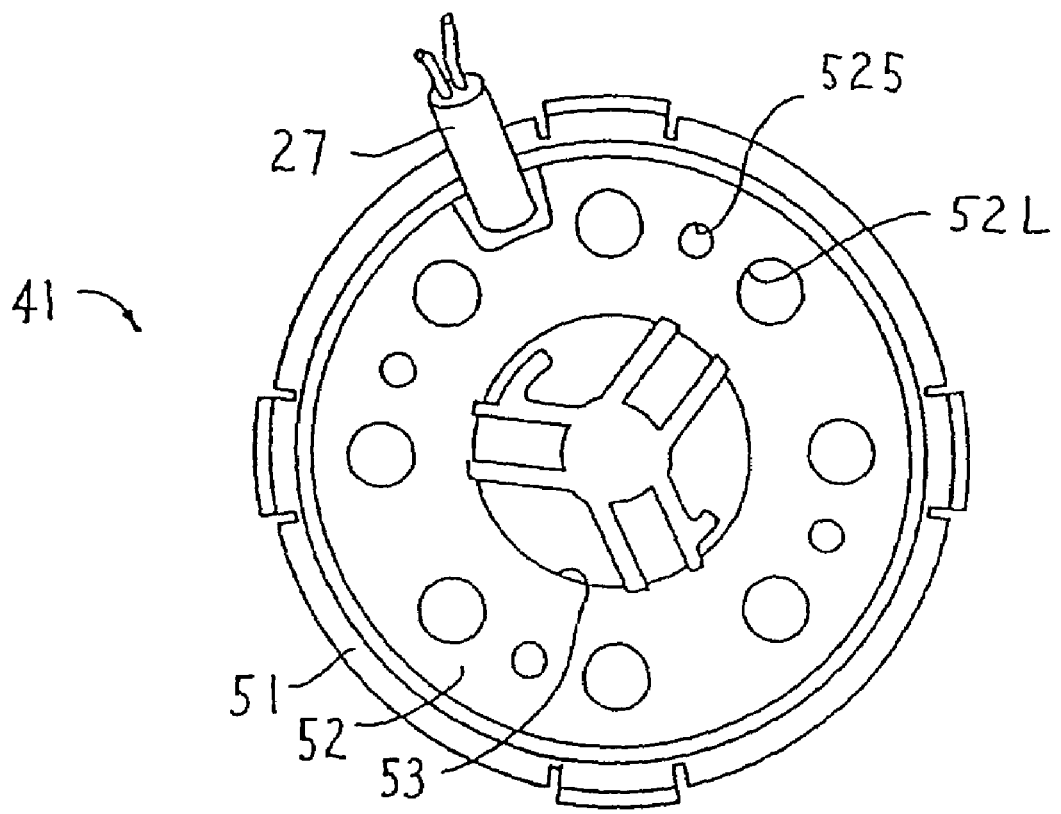
FIG. 12 is a bottom view of the FIG. 10 cup.

In one unit constructed according to the present invention, the lower contacts 92 were installed in a particularly advantageous manner while producing the cup 41 by injection molding. As seen in FIG. 12, the bottom wall 52 of the cup 51 is perforated by circumferentially spaced large and small holes 52L and 52S respectively. Same are left by wide and narrow mold pins (not shown) upstanding from a (not shown) mold floor underlying the bottom wall 52 (FIG. 10) of the cup 41 when forming same by molding. Eight of the conductive circular disks 93 (FIG. 19) were continuously connected in a circle by the straps 94 and supported just above the mold floor by the wide mold pins which produce the larger diameter holes 52L above-mentioned. Plastic material injected into the mold filled the area between the disks 93 and mold bottom to form the cup bottom wall 52 against the underside of the disks 93. Insertion of a tool up through the small holes 52S break the straps 94 located thereabove to leave four pairs of disks 93 unconnected by straps, with a strap 94 between the disks 93 of each pair, as in FIGS. 16 and 19.

In the embodiment shown, the motor M requires a nominal 12-volt DC power supply. Accordingly, it is appropriate to provide eight batteries B of the nominal 1½ volt inexpensive, commercially available AA type. In view of their long shelf life and relatively high power storage capability and capability to supply adequate voltage until nearly fully discharged, alkaline batteries are preferred.

Figure 11:
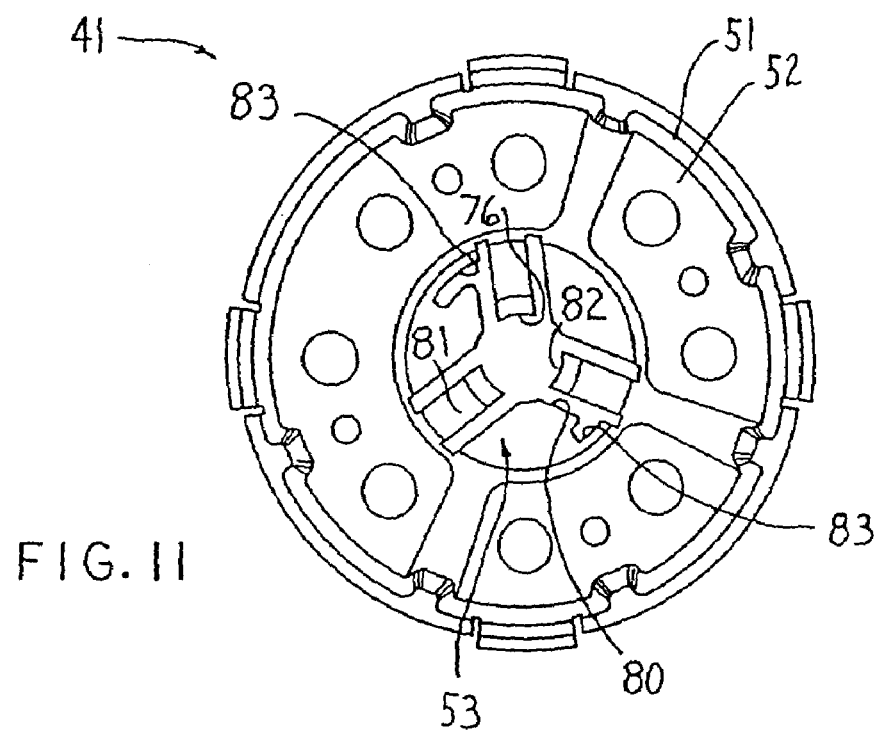
FIG. 11 is a top view of the FIG. 10 cup.

In the embodiment shown, the motor M has a pair of electrical contacts MC protruding from the bottom thereof and electrically energizable for rotating the motor shaft. In the embodiment shown in FIG. 11, circumferential extensions 83 of the slots 80 are diametrically opposed in the top of the drum 53 and the electric contacts MC of motor M extend downwardly therethrough for electrical connection in circuit with the batteries B and the switch SW hereafter described.

Circumferentially spaced ribs 95 (FIG. 8) extend upward along and protrude radially in on the sidewall 51 of the cup 41 and closely radially oppose corresponding ones of the fins 65 of the locator 42. However, the radially outer part of the one of the fins 65 is eliminated, as indicated at 65A in FIG. 13, and its corresponding upstanding cup rib 95 is eliminated, leaving a cable space 96 radially therebetween. Electric cable 27 (FIG. 5) extends through this cable space 96, substantially vertically along the cup sidewall 51 and exits up through a cable port 101 in the deck 60 near the edge thereof and down through a cable port 102 in the bottom wall 52 of the cup 41. The electric cable 27 here incorporates two insulated electric wires generally indicated at 103.

The cover 43 (FIGS. 2-6 and 23-26) includes a downwardly opening dome 110, a radially outward extending bottom flange 112 and the inlet connector 12.

Figure 6:
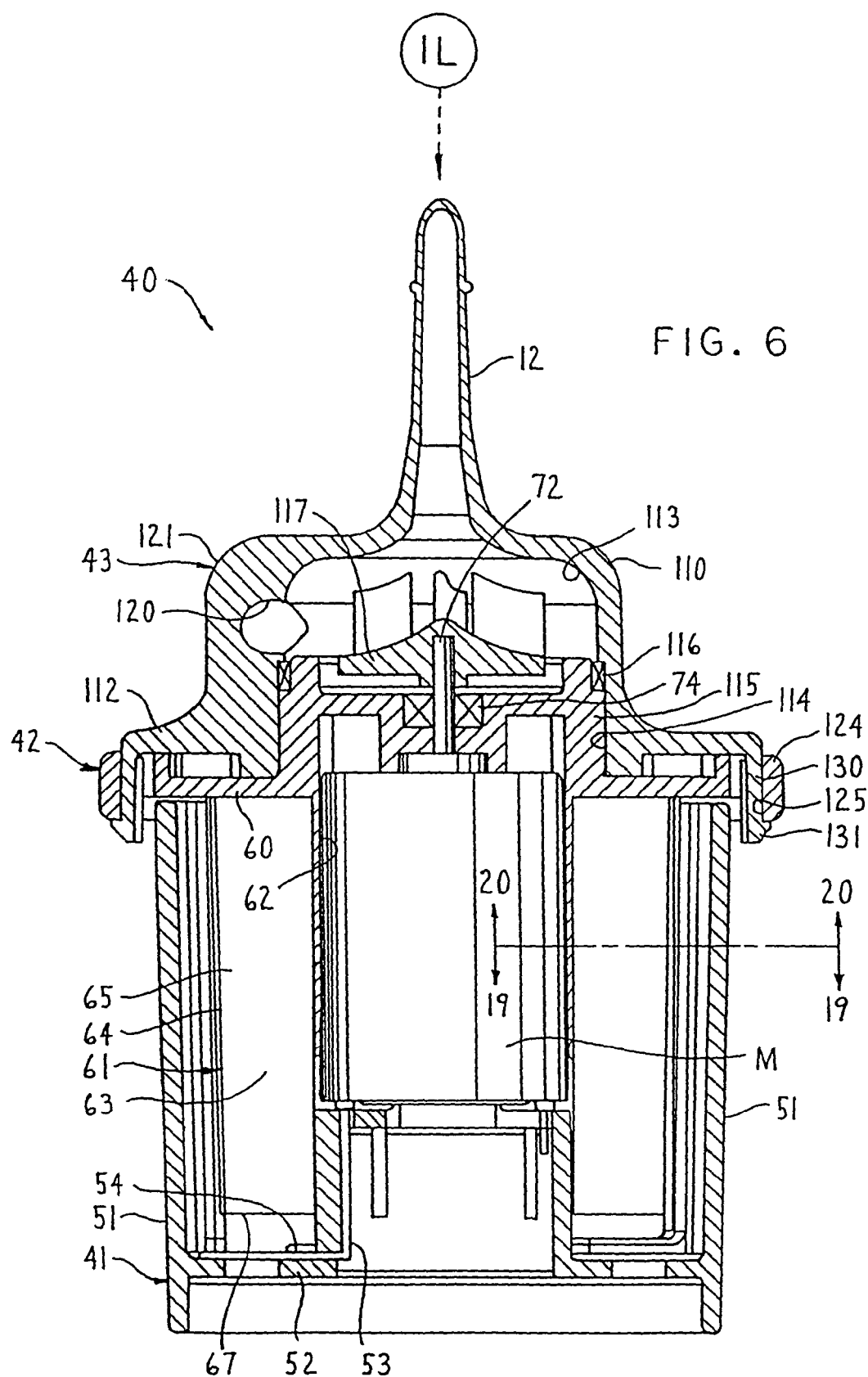
FIG. 6 is a central cross-sectional view similar to FIG. 5 but with the diametral cutting plane rotated to cut through a diametrically opposed pair of depending cover tabs, as generally indicated by the line 6-6 in FIG. 2.

The inlet connector 12 takes the form of a hollow spigot upstanding from the top of the dome 110 and, as seen in FIG. 6, provides an irrigation liquid inlet conduit down through the top of the dome 110 and into a pump chamber 113 occupying the upper part of the dome 110. A recess 114 (FIG. 5) is stepped radially outward slightly from the pump chamber 113 and extends downward therefrom through the bottom of the cover 43. The central portion of the deck 60 (FIGS. 2 and 6) protrudes upward to form a relatively large diameter, generally cylindrical plug 115 which is received snugly upward into the downwardly opening recess 114 of the dome 110. A resilient, annular seal 116 (FIG. 6) is trapped vertically between axially opposed steps adjacent the top of the recess 114 and plug 115 to seal the bottom of the pump chamber 113. A preferably conventional centrifugal pump rotor 117 (FIGS. 5 and 6) is fixed coaxially atop the motor shaft 72 in the pump chamber 113. The motor shaft 72 and pump rotor 117 are preferably coaxial with the liquid inlet 12. An outlet passage 120 extends tangentially from the pump chamber 113 within a tangential extension 121 (FIG. 2) of the dome 110 and has an enlarged diameter outlet recess 122 adapted to fixedly sealingly receive therein the end of the irrigation liquid tube 23 as seen for example in FIG. 2, to pump irrigation liquid into the tube 23.

Figure 1:
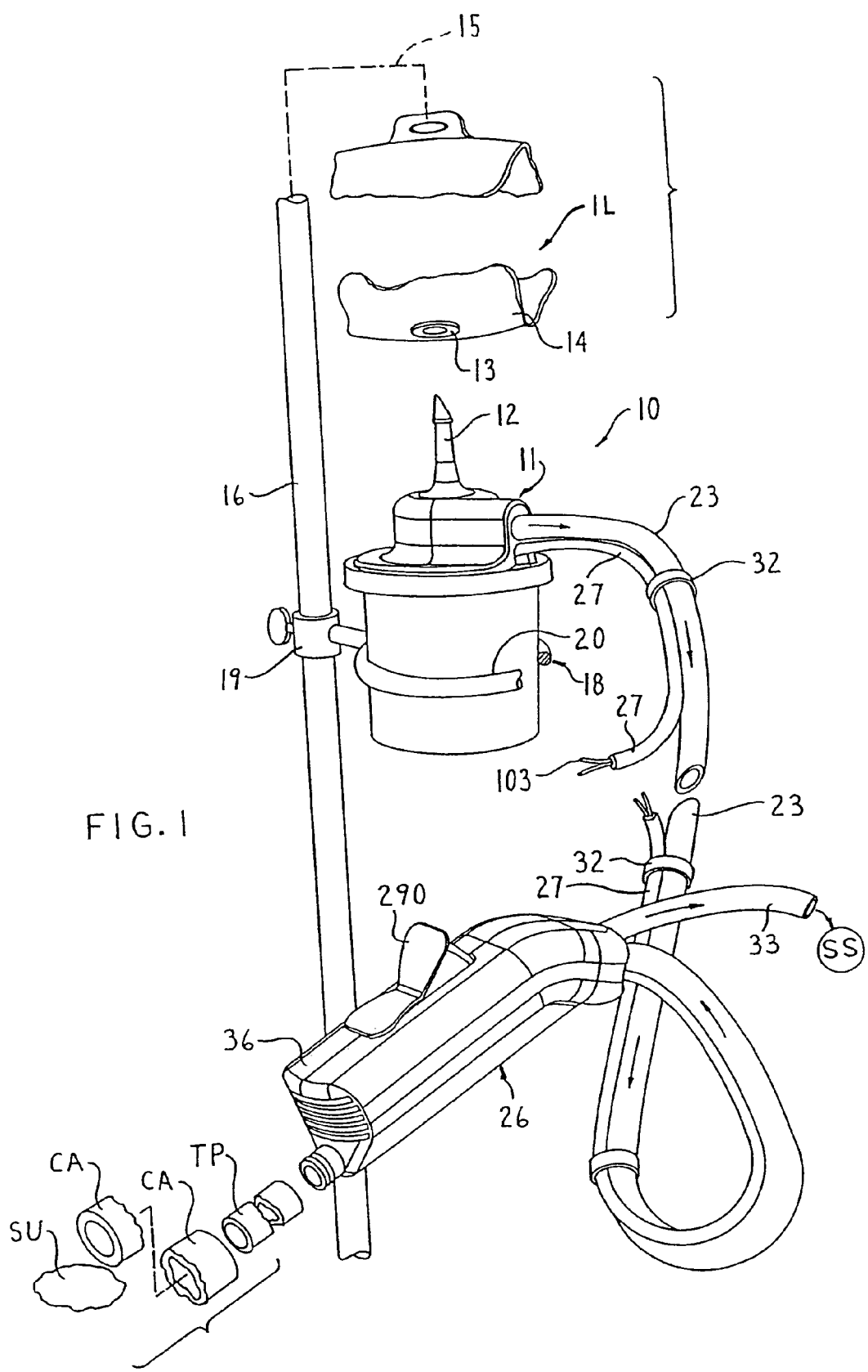
FIG. 1 is a fragmentary, partially broken, somewhat schematic view of a system embodying the invention.

Immediately beneath the outlet recess 122 in the tangential dome extension 121 is a downwardly and radially outwardly opening groove 123 which is blind at its radially inner end. With the cover fixed in its proper location atop the locator 42, the blind groove 123 opens downward into the upper cable port 101 in the deck 60 of the locator 42, to route the cable 27 (FIG. 5) upward and radially outward and away from the pressure liquid unit 11 and along the path of the irrigation liquid tube 23, as generally indicated in FIG. 1.

The cup 41 and locator 42 and cover 43 are fixed together, preferably by snap fit connections, as follows. The deck 60 (FIG. 4) has an upwardly and downwardly thickened rim 124. Radially inboard from the rim 124, the deck 60 is axially punctured by circumferentially extending, circumferentially spaced slots 125 and 126. The slots 125 alternate circumferentially with the slots 126.

Circumferentially spaced, generally L-profile tabs 130 each depend slightly bendably from the perimeter edge of the cover 43 and insert downward into a respective slot 125 in the deck 60. Each tab 130 has a radially outward extending lip 131 (FIGS. 4 and 6) which snaps radially outward under the deck rim 124 to hold the cover 43 fixed downward firmly against the deck 60 of the locator 42.

Figure 4:
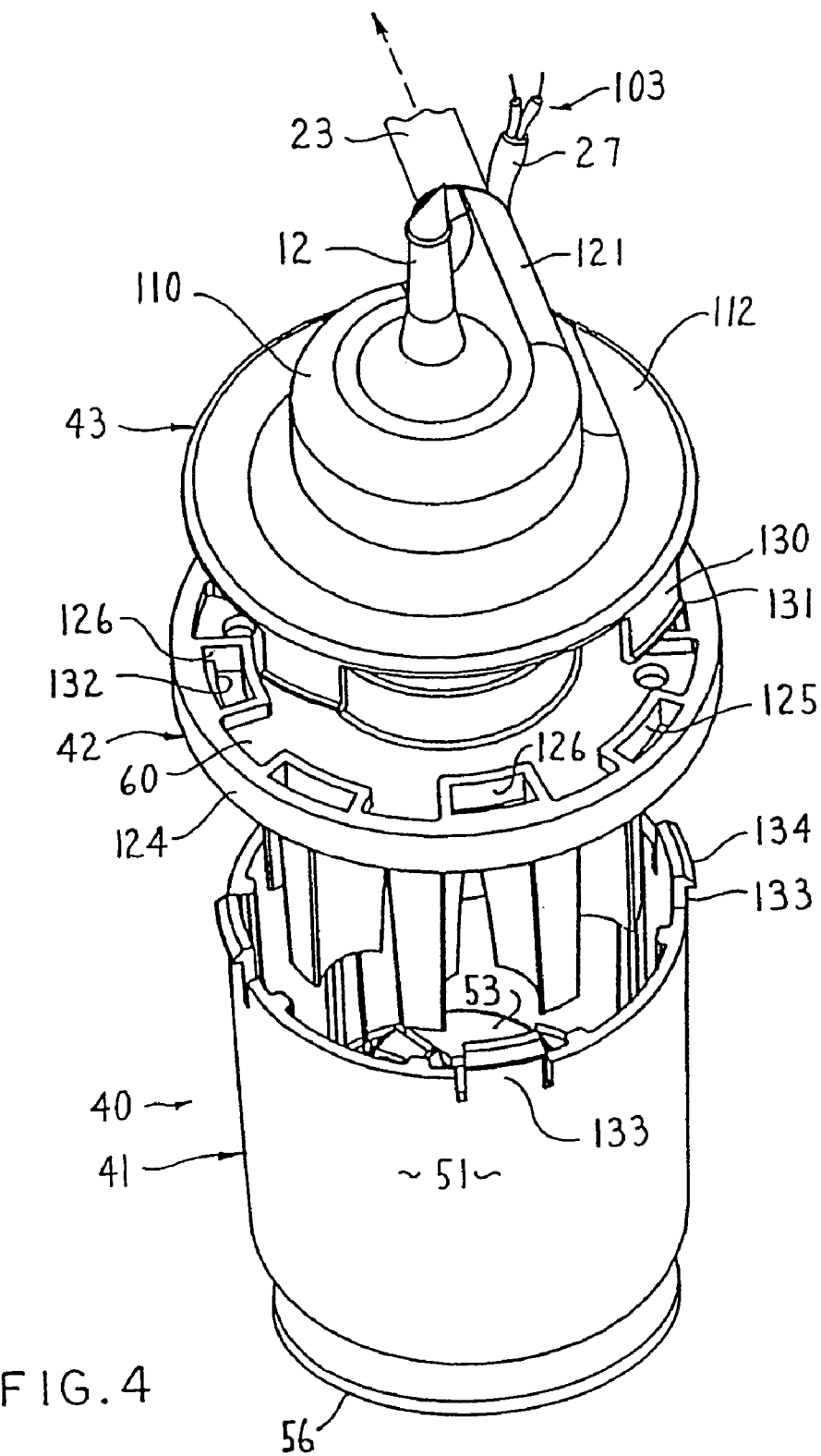
Figure 13:
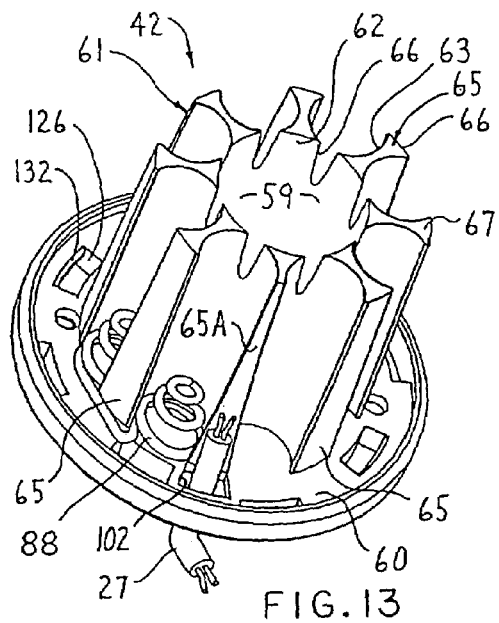
FIGS. 13 and 14 are pictorial views of the locator of FIGS. 2-4, looking respectively toward the bottom and top thereof.
Figure 15:
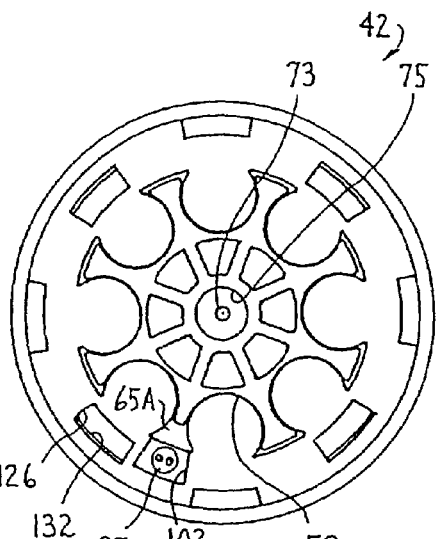
FIG. 15 is a bottom view of the FIG. 13 locator.

The slots 126 each have a circumferentially extending step 132 upset radially inward from the rim 124 near the bottom of such slot 126, as indicated for example in FIGS. 4 and 13. Circumferentially spaced tabs 133 extend up from the sidewall 51 of the cup 41 and are generally L-shaped, each having a shallow radially outward extending lip 134. The tabs 133 are circumferentially in register with the remaining slots 126 in the locator deck 60. Upon bringing the cup 41 upward coaxially toward the deck 60, the tops of the tabs 133 enter the slots 126. As the top of the cup 51 moves into contact with the underside of the deck 60, the tab lips 134 each advance upward past, and are deflected resiliently radially inward by, the corresponding step 132 to snap over such step 132.

In this way, the tabs 130 and 133, properly lodged in their slots 125 and 126 maintain the cup 41, locator 42 and cover 43 rigidly fixed in assembled relation, as seen in FIG. 1, together.

While the cup 51, locator 42 and cover 43 may be of any desired rigid material and manufactured in any desired way it is convenient to mold same each in one piece, of a conventional plastics material.

A circular, disk-like label of generally rigid material, such as cardboard, styrofoam, or the like, fits snugly up into the downward opening recess 55 (FIG. 3) defined by downward extension of the sidewall 51 a short distance below the bottom wall 52. Such label may be fixed in place as a last step in the assembly operation, by adhesive bonding or by press fit upward into the recess 55 due to the slight downward taper of the cup side wall 51. A suitable disk is indicated at 56 in FIGS. 4 and 5. The disk 56 can be used to cover holes in the bottom wall 52 and wiring between the cable 27 and motor contacts MC and battery lower contacts 93. Such disk 56 could also be used as a label for describing the product, usage and warnings regarding misuse.

Figure 16:
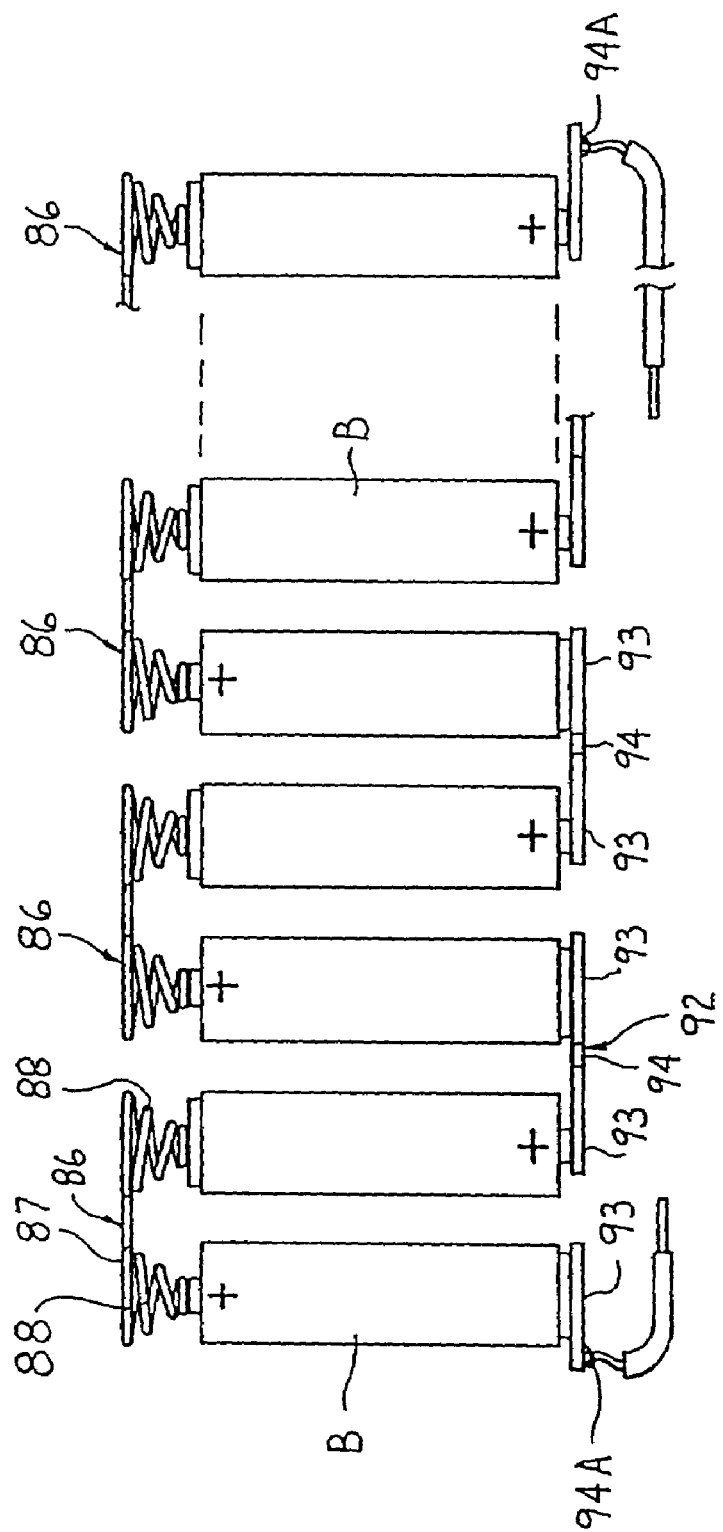
FIG. 16 is a schematic elevational view of the electrical connections for batteries to be carried by the FIG. 13 locator.
Figure 17:
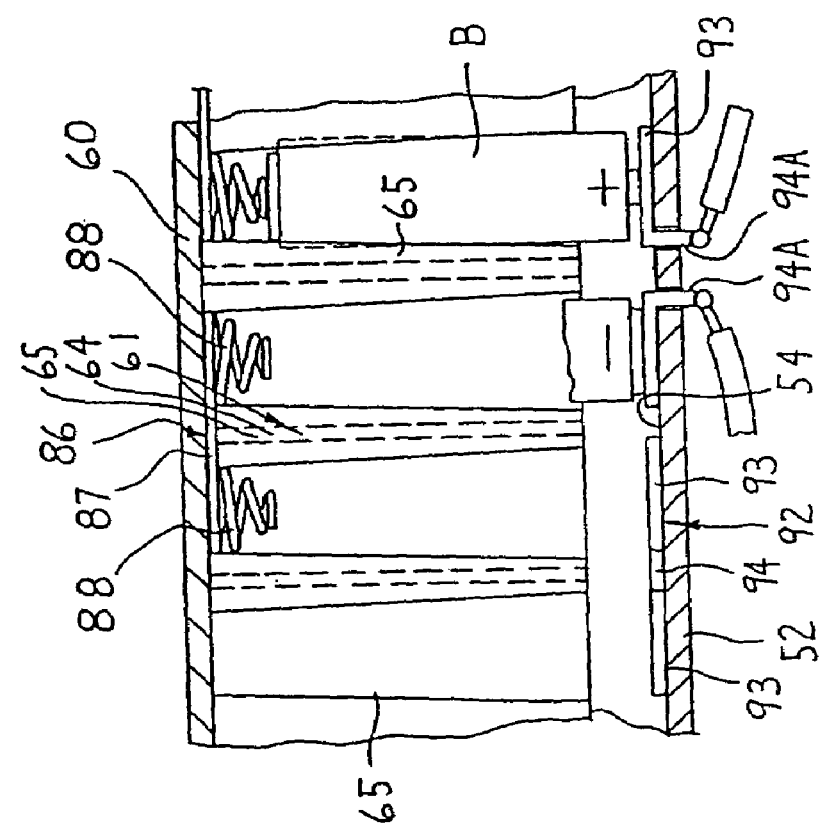
FIG. 17 is a fragmentary generally schematic view illustrating a location of battery contacting elements in the FIG. 13 locator.
Figure 22:
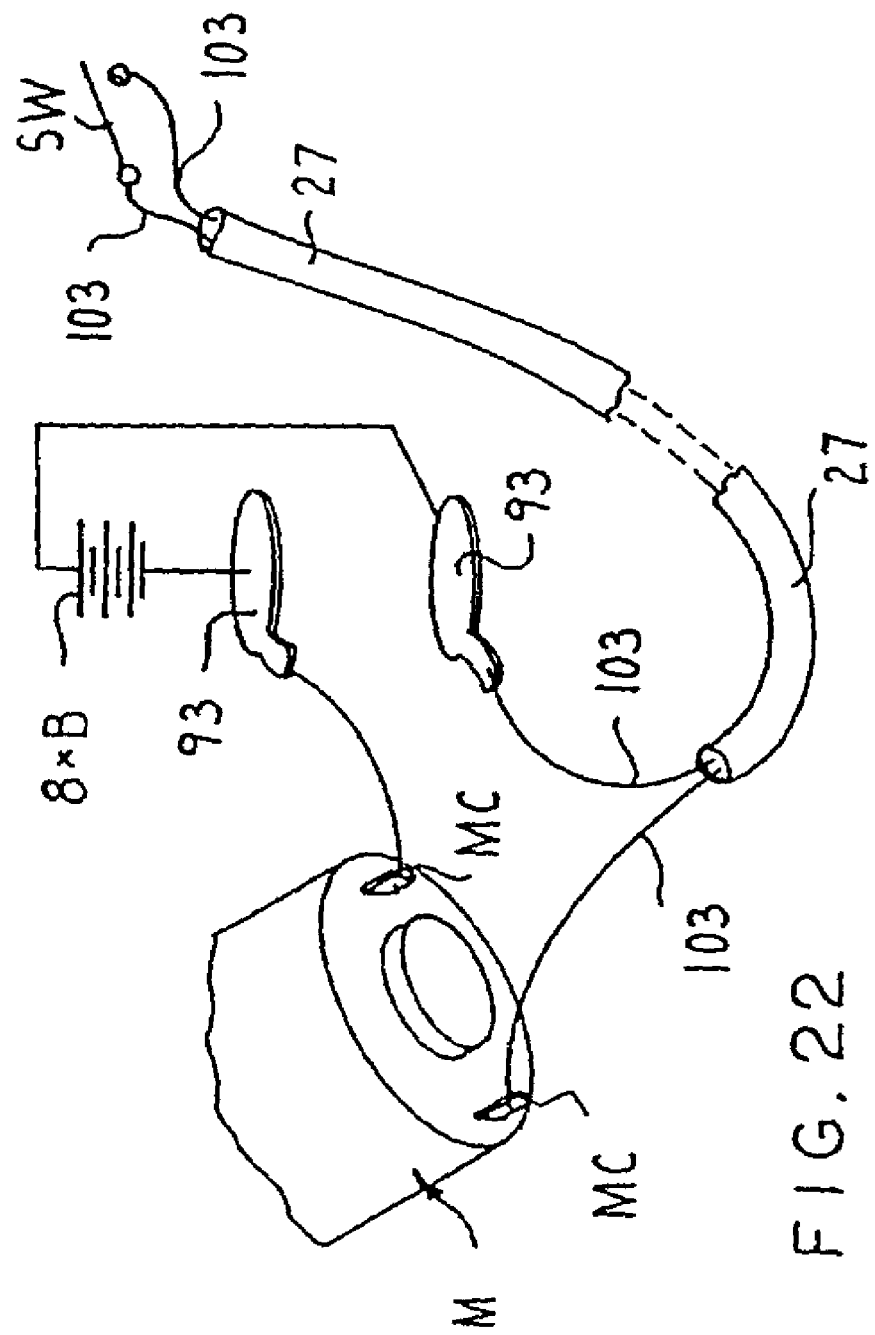
FIG. 22 is a schematic representation of the electrical circuit of the FIG. 1 system.
Figure 23:
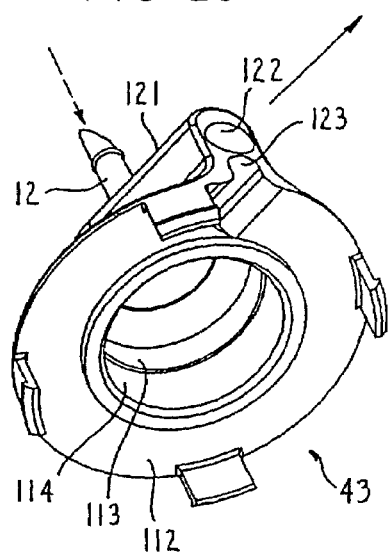
FIGS. 23-25 are pictorial views of the pumping chamber cover of the FIG. 2-4 apparatus, taken from the underside in FIGS. 23 and 24 and from the top in FIG. 25.
Figure 24:
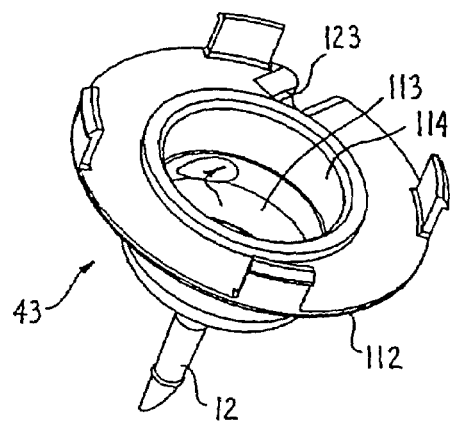
Figure 25:
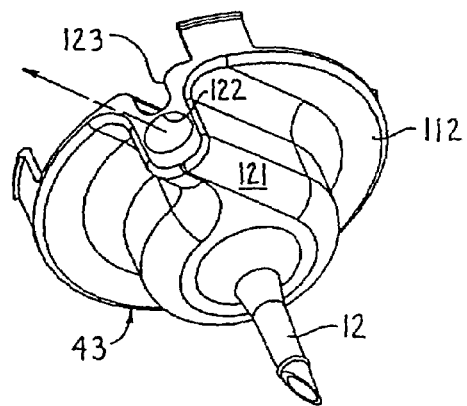
Figure 26:
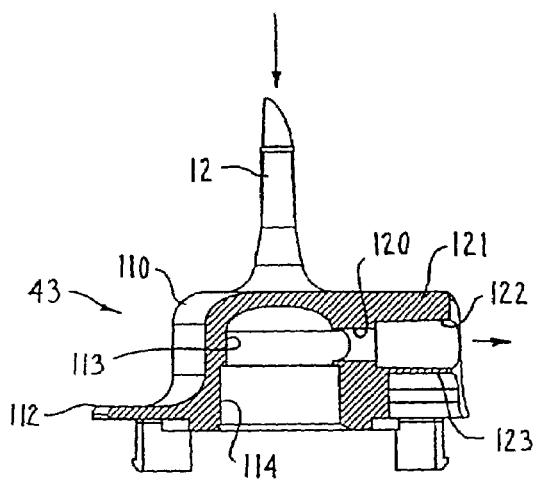
FIG. 26 is a side elevational view of the FIG. 23 cover partially broken on a cutting plane including the central axis of the liquid outlet and cable groove.

The spring wire upper contacts 86 and lower contact disks 93 are located to connect the eight batteries B in series, as seen in FIG. 16 and as schematically indicated at 8×B in the FIG. 22 circuit diagram. The series battery connection 8×B is in turn connected in series loop (through the endmost disks 93) with the motor M (through its contacts MC) and (through the conductors 103 of the cable 27) with the manually actuable switch SW (hereafter described, in the handpiece 26) as shown in FIG. 22.

Handpiece 26

Figure 27:
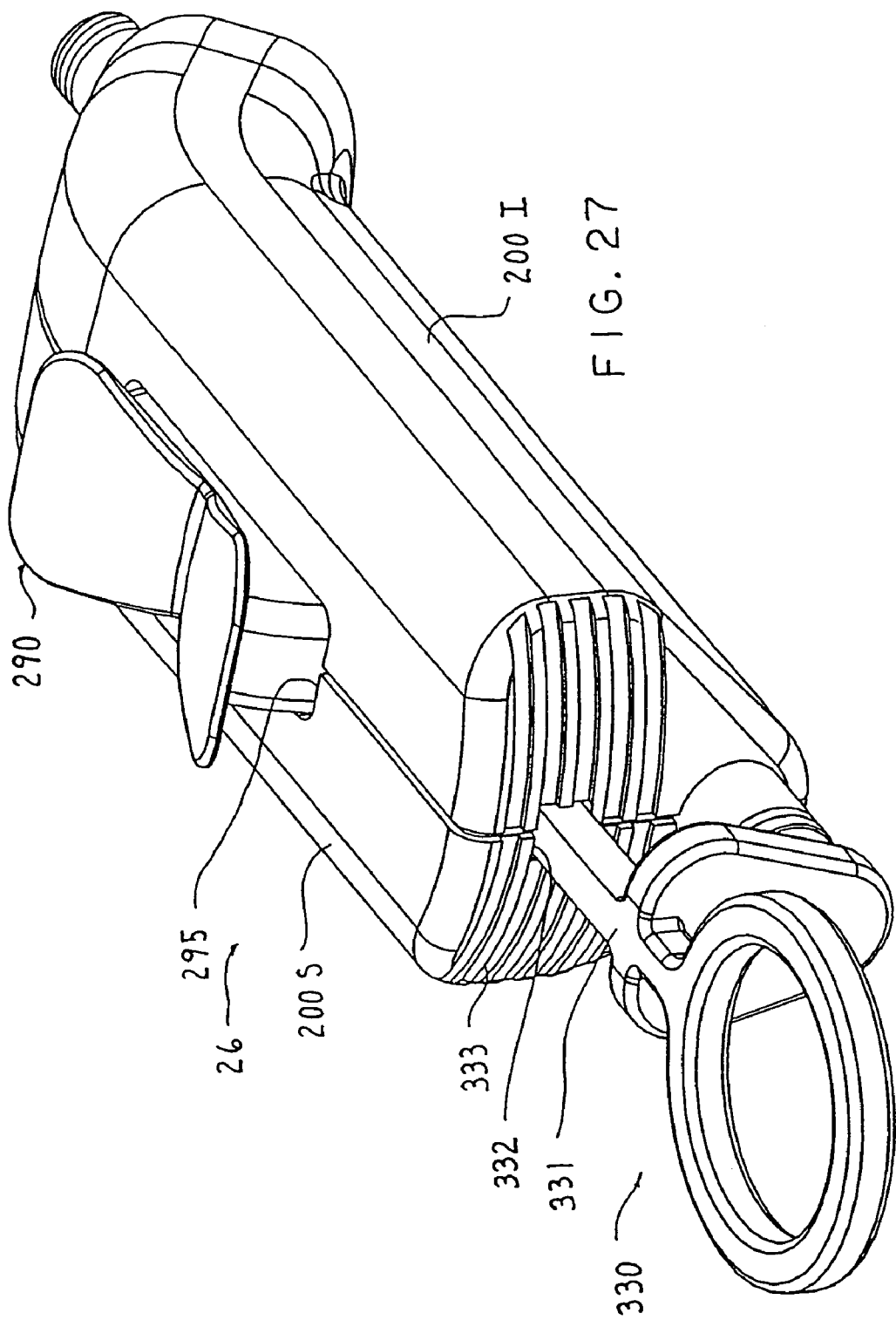
FIG. 27 is a pictorial view of the handpiece of FIG. 1 with the user actuated rocker in neutral (rest) position and the guard pin inserted for packing or shipping.
Figure 28:
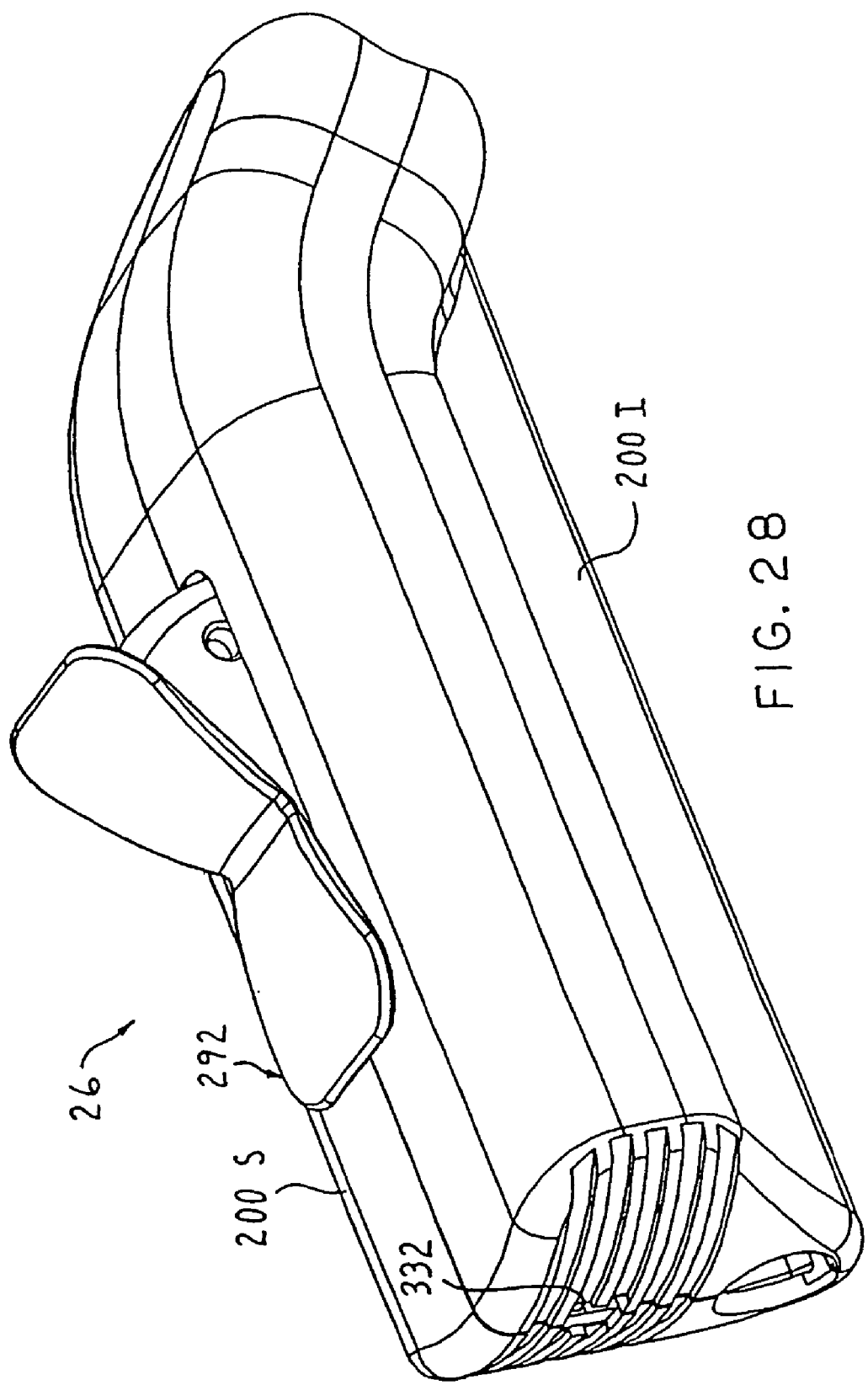
FIG. 28 is a pictorial view generally similar to FIG. 27 but taken at a different angle and omitting the guard pin and the conduit and with the rocker tilted forward.
Figure 29:
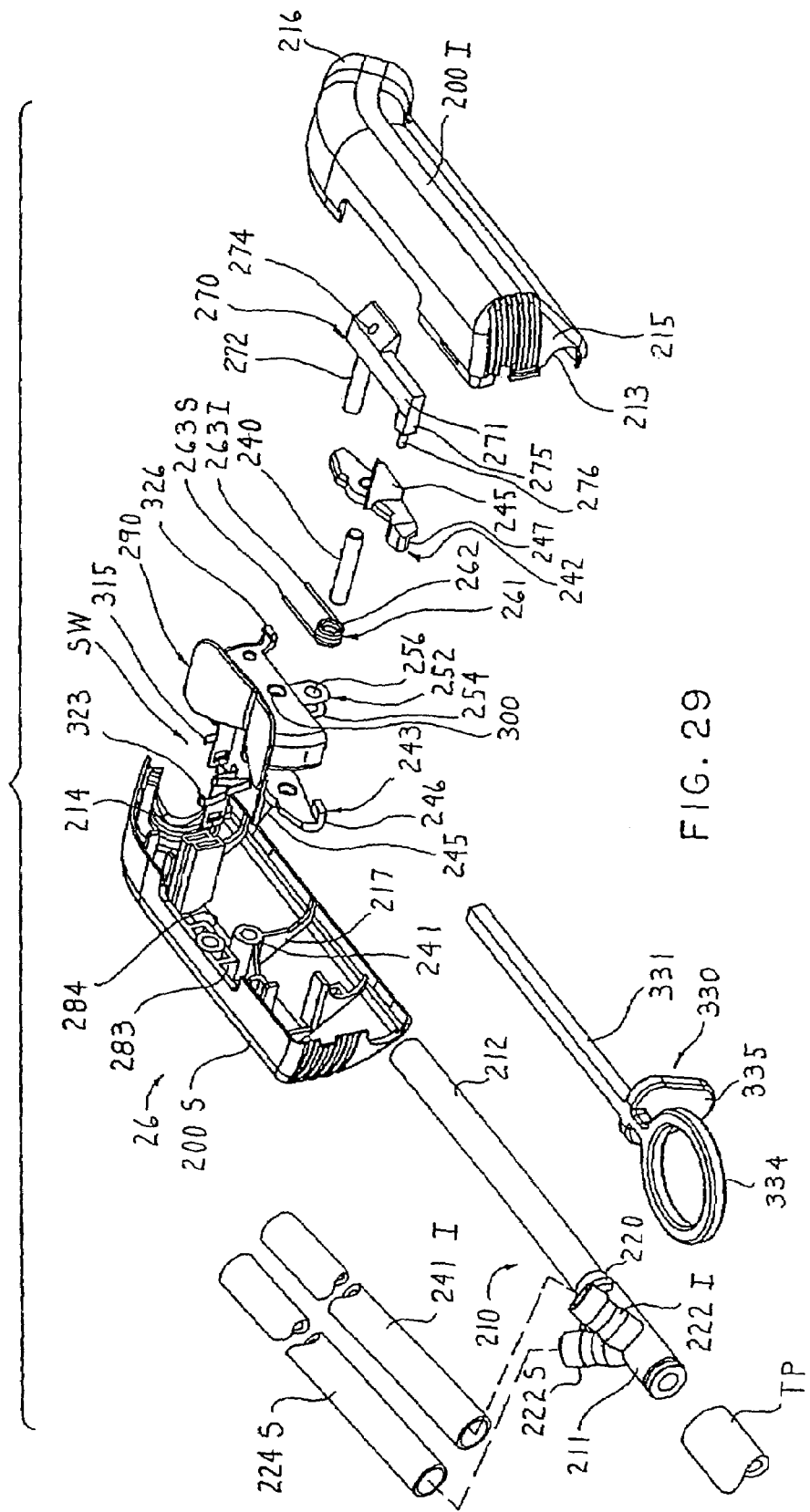
FIG. 29 is an exploded view of the FIG. 21 handpiece drawn in reduced scale and omitting the adapter block at the rear thereof.
Figure 30:
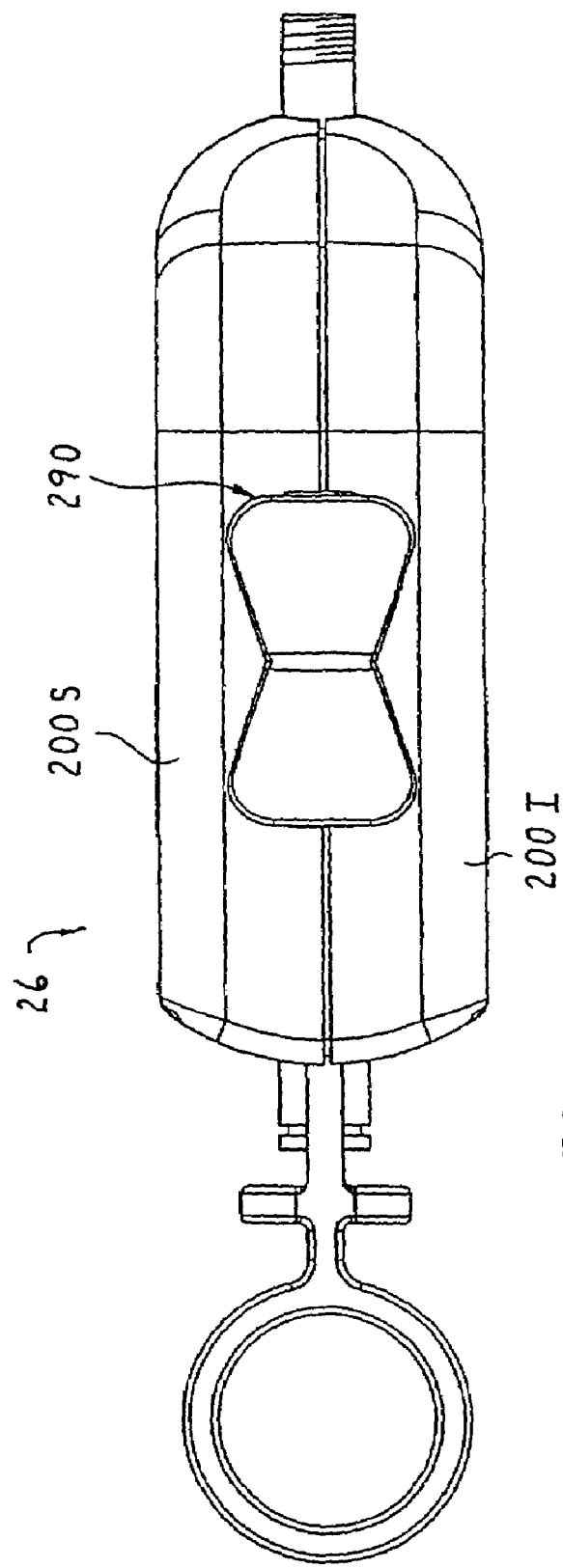
FIGS. 30 and 31 are respective top and bottom views of the FIG. 27 handpiece.
Figure 31:
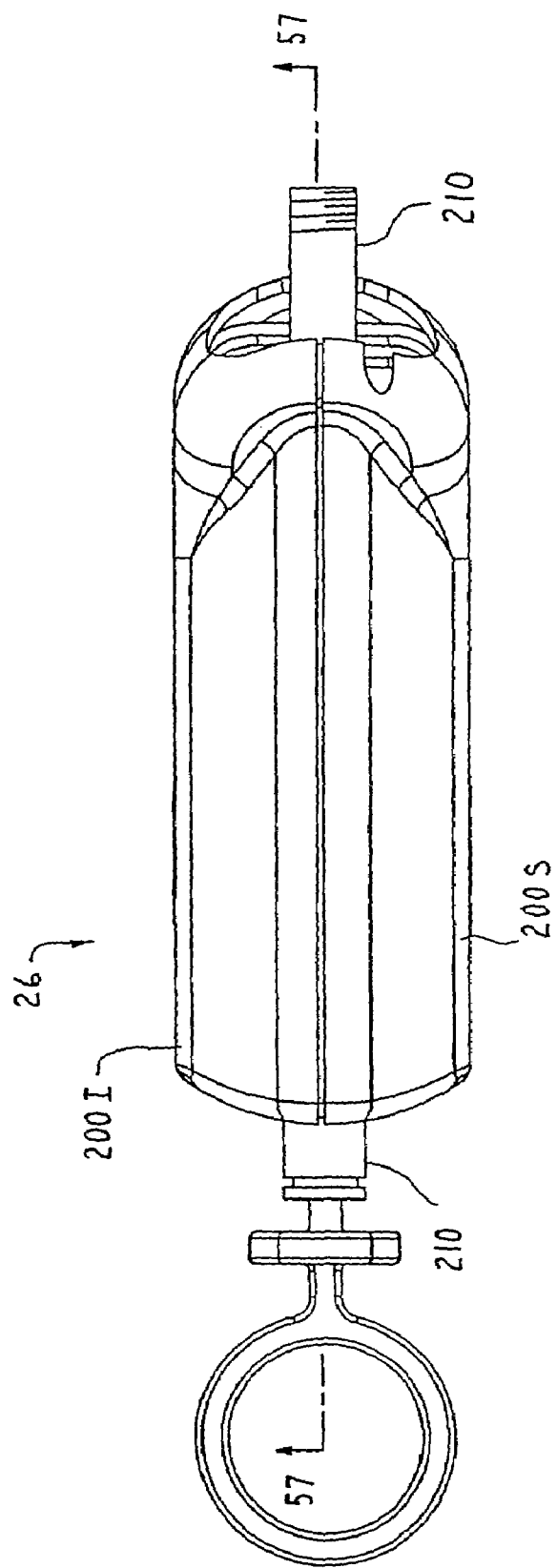

The handpiece 26 comprises an outer shell conveniently defined by opposed concave half shells 200S and 200I located respectively on the suction and irrigation sides of the handpiece, as generally indicated in FIGS. 27-29. In the finished handpiece, the edges 201 of the half shell 200S overlap edges 202 of the half shell 200I (FIGS. 33-38) and are fixed thereto by any convenient means such as conventional snapfit connections 203 and 204 respectively, or by adhesive bonding, or the like.

Figure 57:
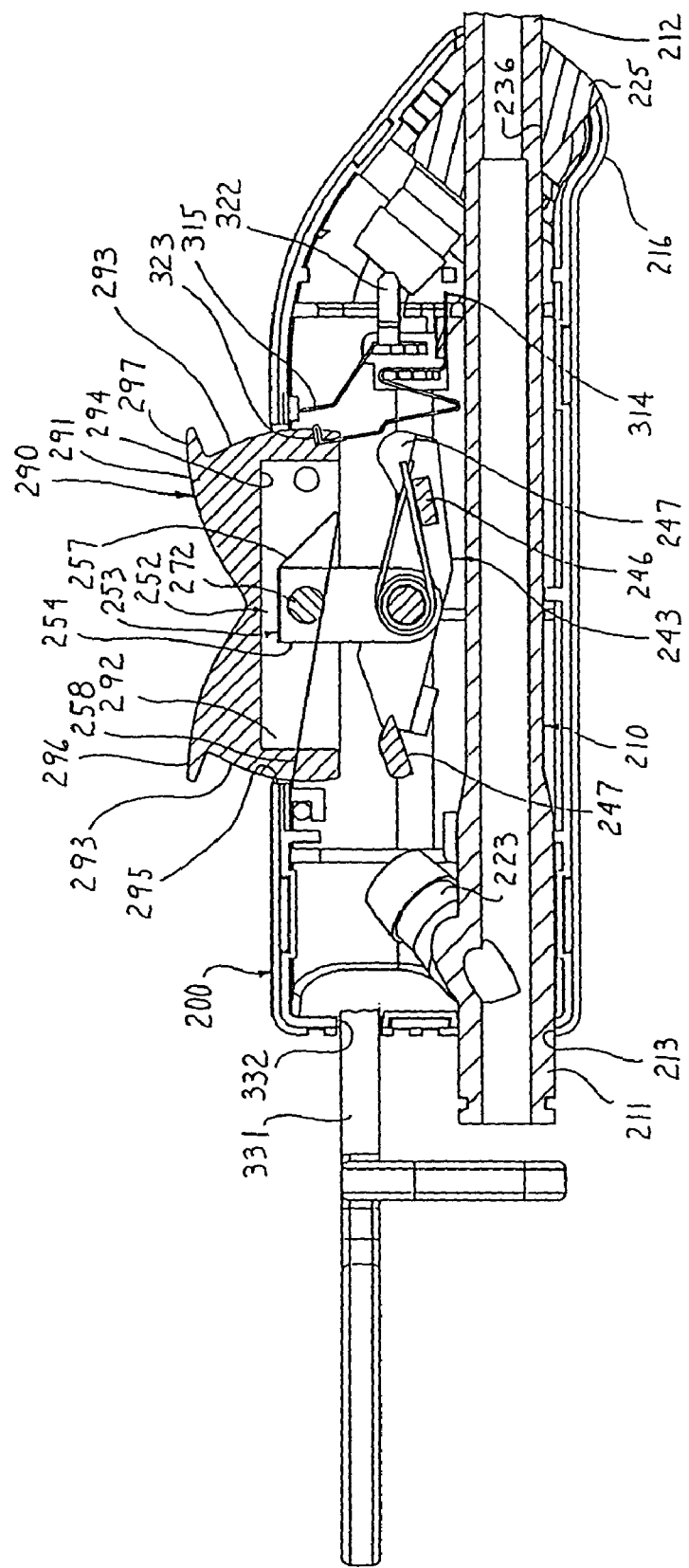
FIG. 57 is a central cross-sectional view substantially as taken on the line 57-57 of FIG. 31 with the rear portion of the guard pin broken away.
Figure 58:
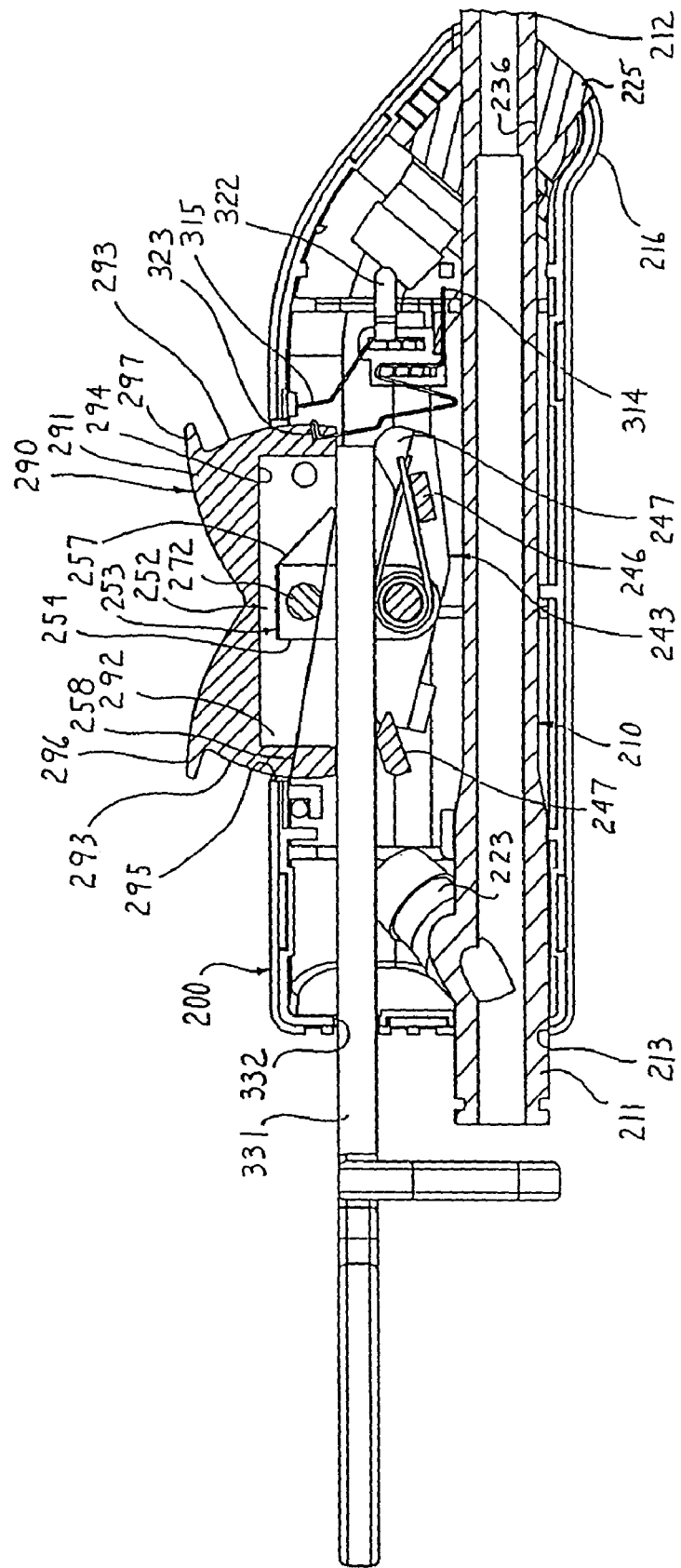
FIG. 58 is a view similar to FIG. 57 but showing the entire guard pin in place.

An elongate rigid conduit 210 extends longitudinally through the lower portion of the shell 200 and has front and rear end portions 211 and 212 which respectively protrude forwardly and rearwardly through front and rear openings 213 and 214 respectively in the substantially radial front wall and in the somewhat downward angled rear end portion 268 of the shell 200 (FIGS. 29 and 57). Longitudinally spaced ribs 217 in the half shells 200S and 200I radially fix conduit 210 therein. Transversely extending tabs 20 (FIGS. 44 and 45) fixed on the conduit 210 are received in ports 221 (FIGS. 35 and 38) opening toward each other in the half shells 200S and 200I to locate the conduit longitudinally fixedly in the shell 200, as seen for example in FIG. 29.

Figure 53:
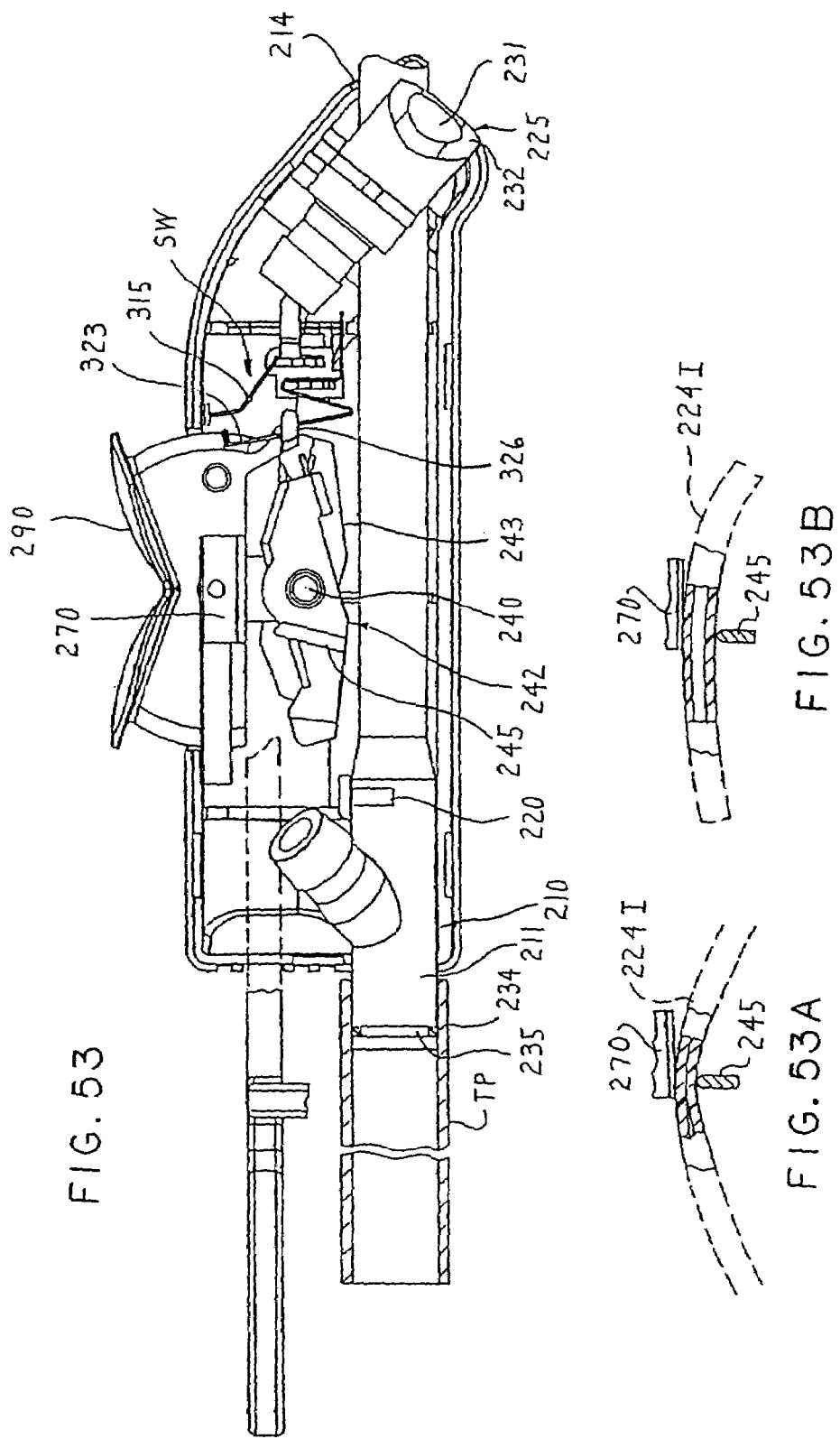
FIG. 53 is an elevational view of the handpiece above-referenced, taken from the irrigation side, with the guard pin in place but with the rear portion of the guard pin shown only in dotted line to better show internal handpiece parts located behind it and with the irrigation side half shell removed.
Figure 54:
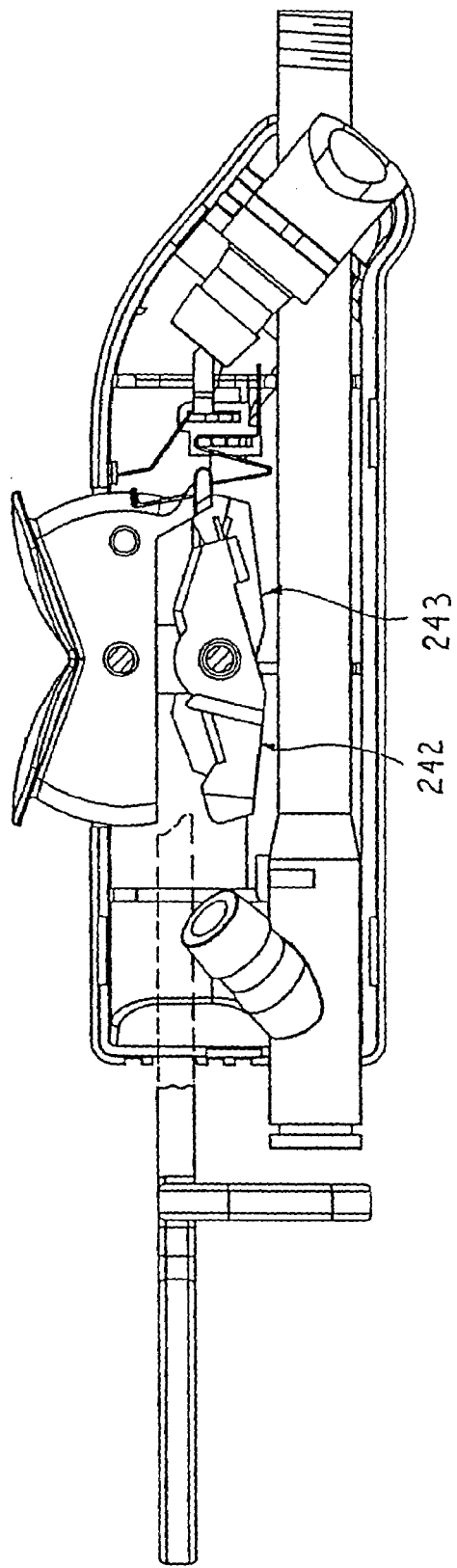
FIG. 54 is a view similar to FIG. 53 but with the irrigation anvil removed.
Figure 55:
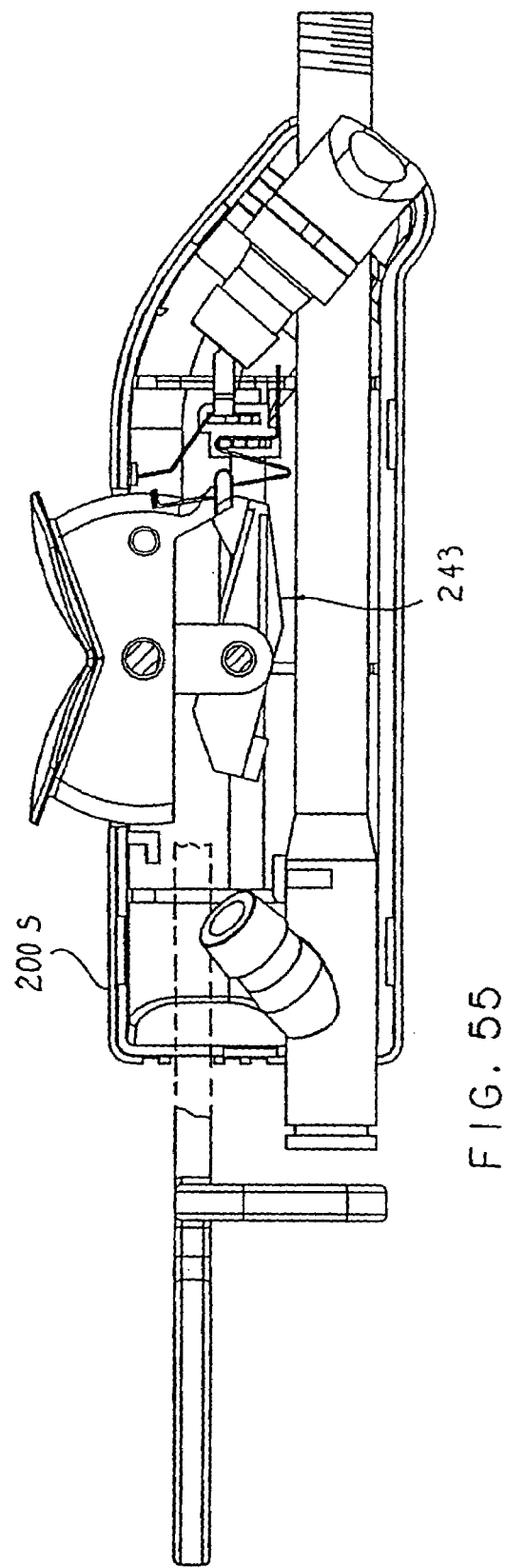
FIG. 55 is a view similar to FIG. 54 but with the irrigation pinch lever removed to show parts behind it.

Conventionally annularly ribbed, hollow, tubular suction and irrigation fittings 222I and 222S (FIG. 29) rigidly connect to the front portion 211 of the rigid conduit 210 inside the shell 200, adjacent the front wall 215 thereof as seen in FIG. 53. The fittings 222S and 222I diverge upwardly and angle rearwardly for fixed securement thereon of respective resiliently pressurably closeable, normally open hoses 224S and 224I (FIG. 29).

The downward and rearward angled rear opening 214 of the shell 200 is normally occupied by an adapter block 225 (FIGS. 42, 43, 53 and 57) fixed into the rear opening 214 (FIG. 53) of the shell 210 during assembly of the two half shells 200S and 200I. More particularly, the adapter block 225 (FIGS. 42 and 43) has laterally protruding, partially circumferentially extending, locator ribs 226 fixed thereon. Reception, during assembly of the half shells together, of the ribs 226 snugly between a forward/rearward spaced pair of further ribs 227 (FIGS. 35 and 38) circumferentially extending in the rear end portion 212 of the half shells 200S and 200I, fixes the adapter block 225 within the shell 200. The adapter block further comprises a laterally spaced pair of generally upwardly and forwardly aimed, externally ribbed fittings 230S and 230I (FIGS. 42 and 43) for receiving thereon, in fixed liquid tight coupled relation, the rear ends of the pinchable hoses 224S and 224I respectively. The fittings 230S and 230I are similar in form to the fittings 222S and 222I above discussed. Passages indicated in broken lines at 231 extend from the open front of the fittings 230S and 230I rearward through the adapter block and open through the rear end face 232 thereof and are adapted to fixedly and nonleakingly receive, in any conventional manner not shown, the front ends of the suction tube 33 and irrigation liquid tube 23, as indicated in FIGS. 42 and 43.

Figure 32:
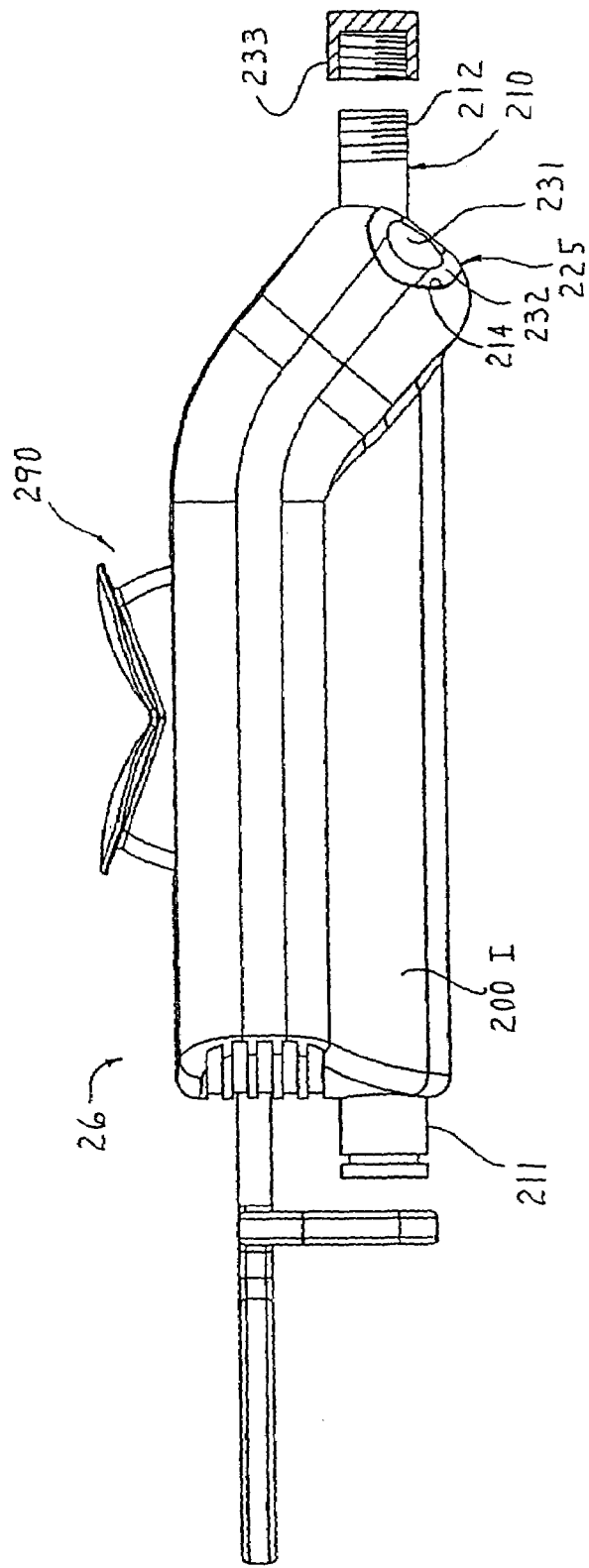
FIG. 32 is a side elevational view of the FIG. 27 handpiece.

The rear end portion 212 of the rigid conduit 210 may be closed by a cap 233 (FIG. 32) releasably secured thereon, by any convenient means such as threads. Alternatively, the cap 233 may be removed to enable insertion forwardly through the conduit 210 of an elongate instrument, or other aid to surgery, whose front end is to be positioned adjacent the surgical site.

The hollow cylindrical tip TP (FIG. 53) is mountable removably on the front end portion 711 of the rigid conduit 210. An O-ring 234 or the like in an annular groove 235 in the conduit sealingly engages the hollow tip TP fixedly to the front end of the conduit 210.

The rear end portion 212 of the rigid conduit 210 passes snugly, but slidably, rearward through a central hole 236 in the adapter block 225 (see FIGS. 42, 43 and 57).

Figure 38:
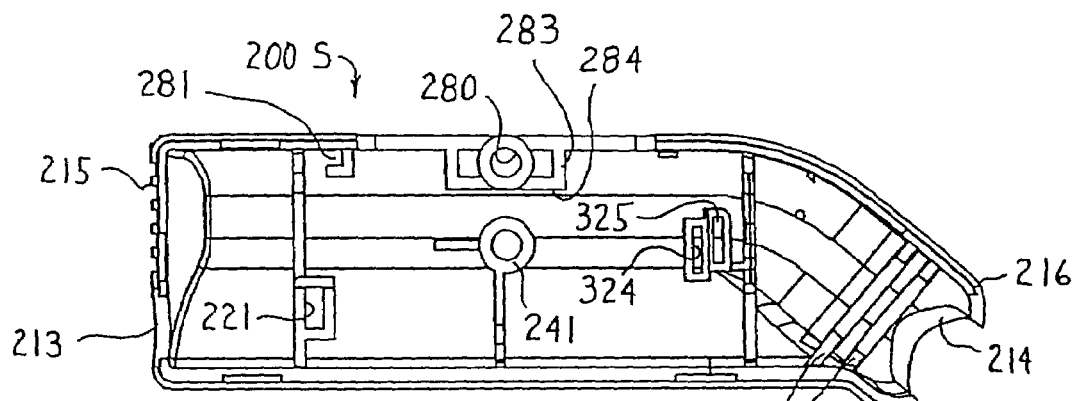
FIG. 38 is an elevational view of the FIG. 37 half shell.
Figure 37:
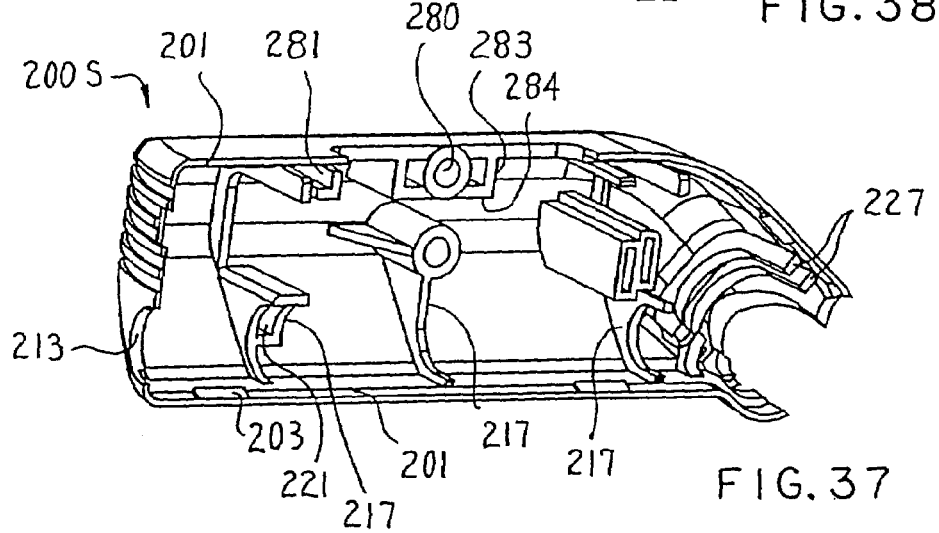
FIGS. 36 and 37 are pictorial views of the other half shell of the FIG. 27 handpiece.
Figure 36:
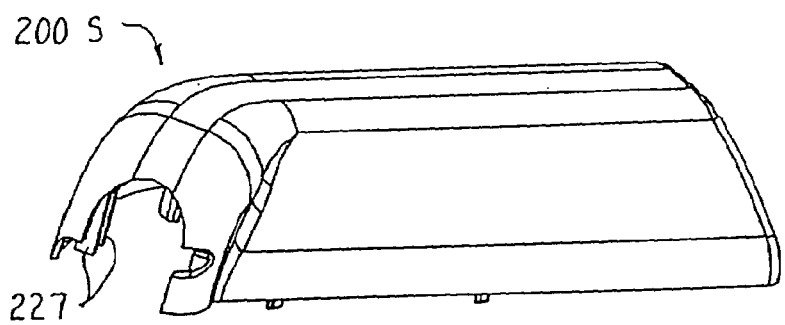

A transverse shaft 240 (FIG. 29) extends across the interior of the shell 200 and has its ends fixed in transversely opposed, tubular bosses 241 (FIGS. 29, 35 and 38). The shaft 240 is located about mid-height in the shell 200.

An irrigation pinch lever 242 and a suction pinch lever 243 (FIG. 29) are located on the shaft 240, adjacent the irrigation half shell 200I and suction half shell 200S respectively. The pinch levers each have mid portions pivoted on the shaft 240 and each extends forward and rearward from the shaft. As seen in FIGS. 40 and 41 the levers 242 and 243 each have a through bore 244 for pivoting on the shaft 240 a round edged pinch blade 245 extending from one side thereof adjacent the bore 244, and a pair of tabs 246 and 247 extending from the other side thereof at respective opposite ends thereof. In the embodiment shown, the tabs 246 are flat and the tabs 247 are domed. In the preferred embodiment shown, the pinch levers 242 and 243 differ only in that the domed tab 247 of the irrigation pinch lever 242 is somewhat flattened, as seen at 248 (FIG. 41). As seen in FIG. 29, the pinch levers 242 and 243 are each assembled on the shaft 240 so that the elongate pinch edge 249 of the blade 245 faces upward but wherein the two pinch blades 245 extend laterally away from each other and toward their respective half shells 200S and 200I. Thus, the pinch levers 242 and 243 are oriented on the shaft 240 such that their respective tabs 247 and 246 are forwardmost (leftwardmost in FIG. 29).

Figure 47:
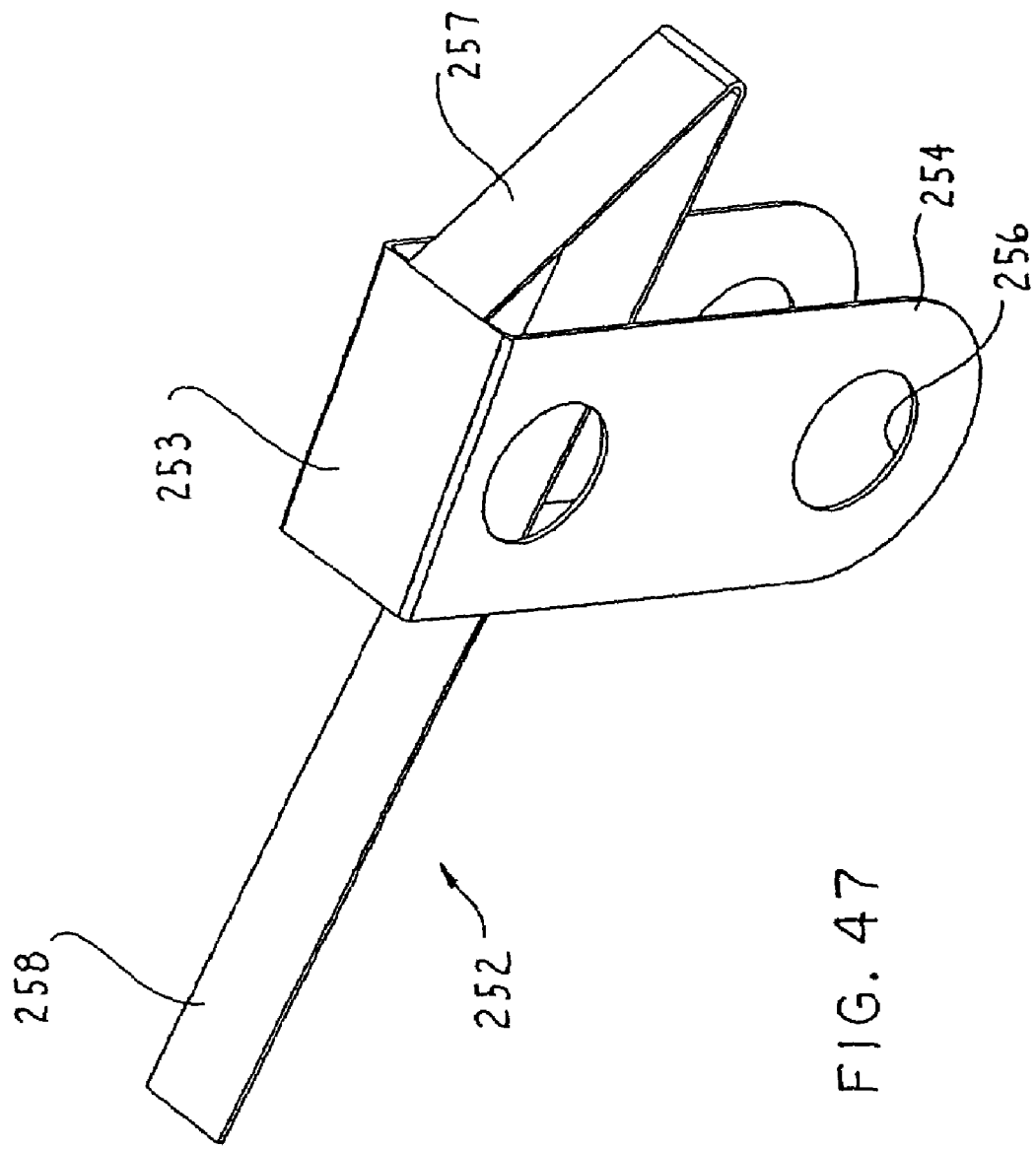
FIGS. 47, 48 and 49 are substantially enlarged pictorial views of the U-spring, switch spring and Z-spring, respectively, of FIG. 29.

A resilient metal U-spring 252 (FIGS. 29 and 47) of springy sheet metal comprises a U-shaped portion 253 comprising a pair of legs 254 depending from a bight 255. Holes 256 through the lower portion of the legs 254 receive the shaft 240 to pivotly locate the U-spring 252 on the shaft 240 snugly between the pinch levers 242 and 243 and with the bight 255 spaced up above the shaft 240. A leaf spring-like arm 257 extends rearward and downward from the bight 255. The free end portion 258 of the arm 257 is bent sharply to extend forward and somewhat upward between the legs 254 in spaced relation between the bight 255 and holes 256.

Figure 52:
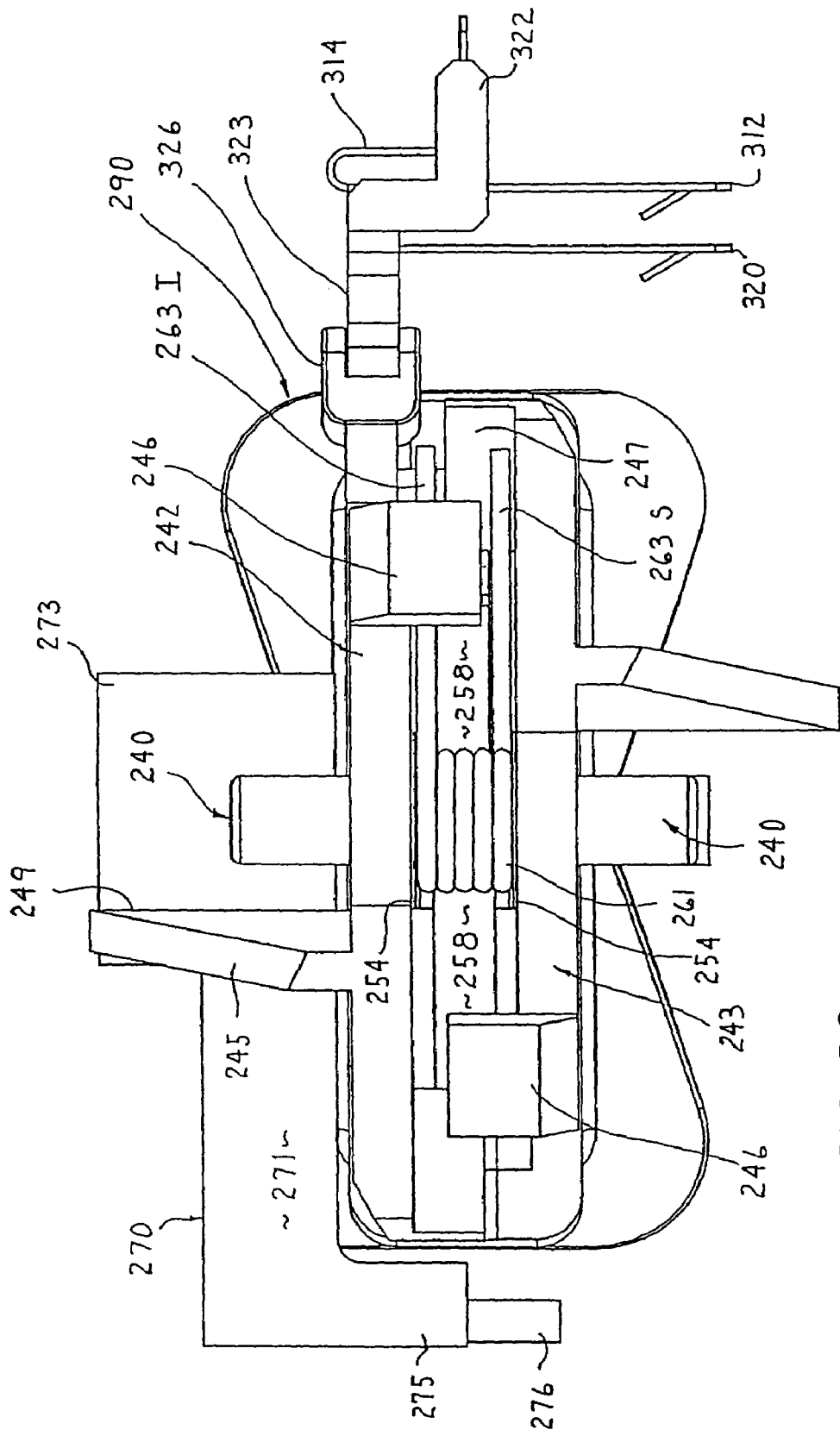
FIG. 52 is an enlarged bottom view of the FIG. 50 subassembly.

A coil torsion spring 261 (FIG. 29) comprises a central portion 262 wrapped around the shaft 240 between the U-spring legs 254 and from which central portion extends a pair of generally rearwardly extending elongate legs 263I and 263S which are vertically trapped between and resiliently urge vertically apart the rear tabs 246 and 247 of the pinch levers 242 and 243 (FIGS. 52 and 53).

A rigid, preferably unitary, anvil 270 (FIGS. 29 and 39) comprises a fore/aft extending bar 271 locatable between the half shells 200S and 200I (FIG. 29) and spaced above the shaft 240. At the rear end portion of the bar 271, a horizontal shaft 272 (FIG. 39) extends toward the half shell 200S. The bar is widened toward the half shell 200I to form a downwardly stepped, downwardly facing anvil surface 273. A hole 274 in the rear end portion of the bar 271 is coaxial with the shaft 272 and faces in the opposite direction, namely toward the half shell 200I. The bar 271 is generally L-shaped, as seen from above, having a leg 275 aimed toward the half shell 200S and terminating in a pin 276. In the assembled handpiece 26, the anvil 270 is fixed with respect to half shell 200S by entry of the free end of its shaft 272 and the pin 276 into corresponding holes 280 and 281 in, and adjacent the top of, the half shell 200S (FIGS. 29, 37 and 38) and by entry of a pin 282 (FIGS. 34 and 35), fixed within the opposite half shell 200I just below the top thereof, into the opposed hole 274 in the rear portion of the anvil 270. In this manner, the anvil 270 is firmly fixed within the assembled shell 200. The anvil 270 is spaced above the irrigation pinch lever 242, with its down facing anvil surface 273 directly opposing the upfacing pinch edge 249 of the pinch blade 245 of the irrigation pinch lever 242 (FIGS. 52 and 53) for coaction therewith in pinching and unpinching the irrigation hose 224I which is routed therebetween.

A further anvil, which may termed the suction anvil, 283 (FIGS. 29, 37 and 56) is fixed in and preferably formed integrally with the half shell 200S and has a down facing anvil surface 284 underlying the upper shaft hole 280 and at about the same height as the anvil surface 273 cooperating with the irrigation pinch lever 242 above-described. The down facing anvil surface 284 overlies and cooperates with the upfacing pinch blade edge 249 of the suction pinch lever 243 for pinching and unpinching the suction hose 224S routed therebetween.

Figure 50:
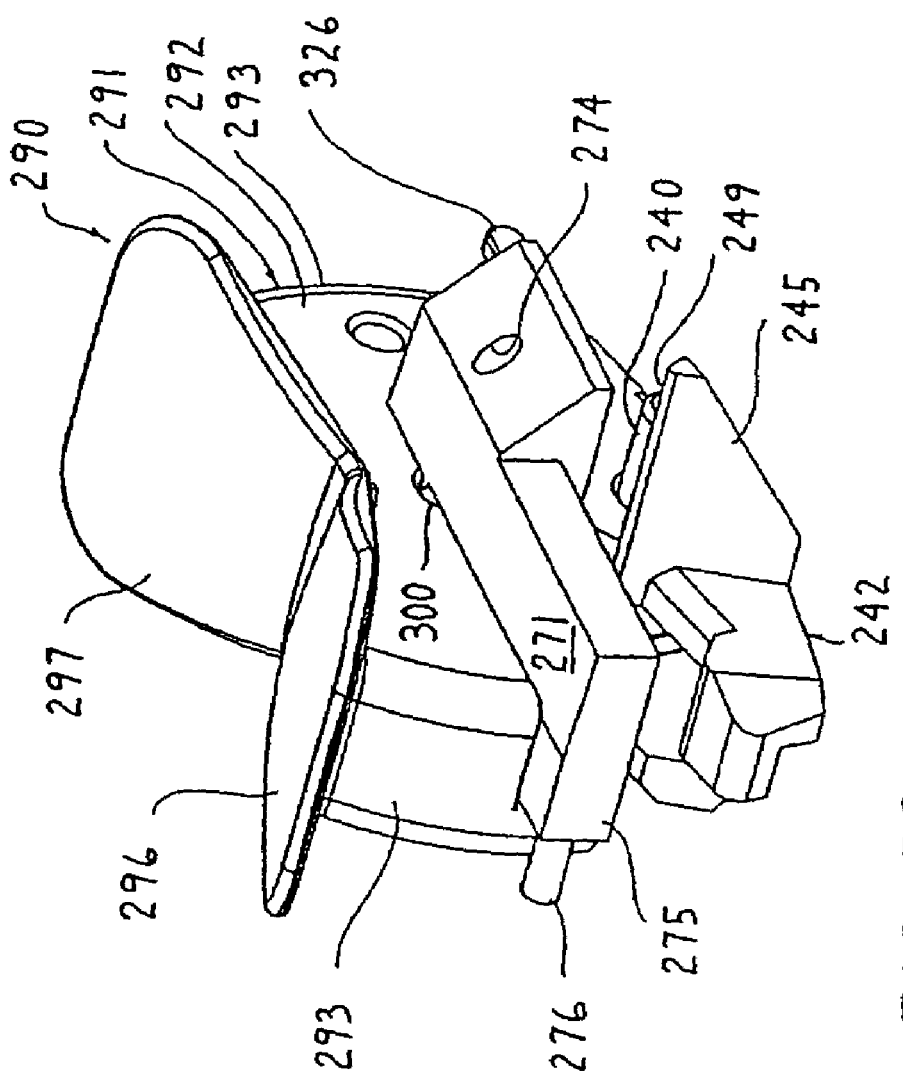
FIG. 50 is an enlarged pictorial view of a subassembly of the FIG. 29 handpiece.

A hand actuable rocker 290 (FIG. 29) comprises a generally box-like body 291 (FIG. 50) having parallel upstanding side walls 292 and convexly rounded, upwardly converging front and rear end walls 293. The body 291 includes a relatively large, generally rectangular, downwardly opening recess 294 (FIG. 57). The body 291 extends down through an opening 295 in the top of the shell 200. The body is topped by fixed, preferably integral, divergently angled, front and rear push pads 296 and 297.

Figure 56:
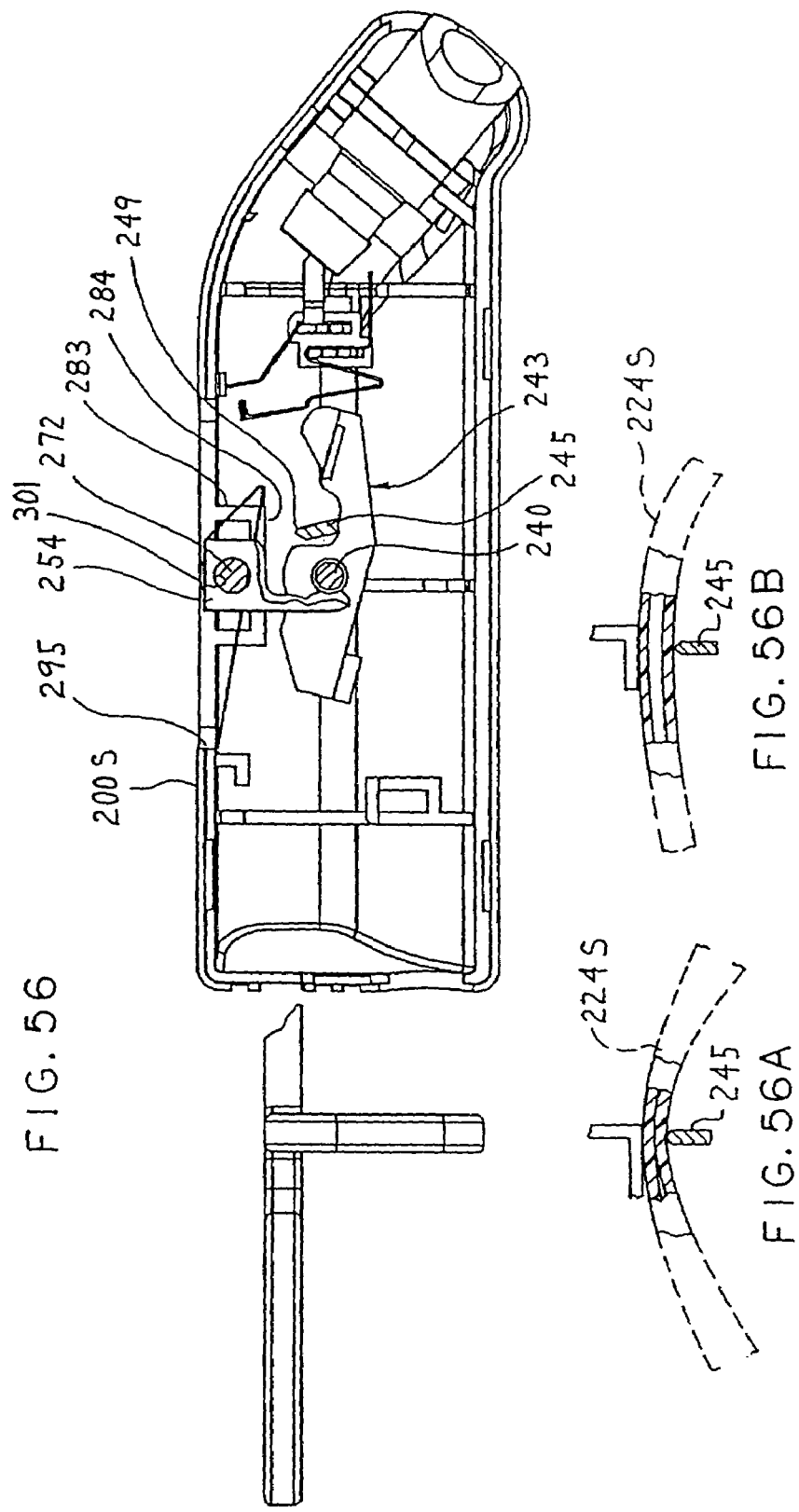
FIG. 56 is a view similar to FIG. 55 but with the rocker removed and portions of the U-spring and suction pinch lever removed to better show the suction tube pinch blade opposing the corresponding anvil surface.

The recess 294 of the rocker 290 receives upwardly thereinto the upper portion of the U-shaped part 253 of the U-spring 252, the top of the U-shaped part 253 being spaced below the top of the recess 294 in the rocker. The upper (anvil) shaft 272 (FIGS. 29 and 57) extends laterally through holes 300 in the sides 292 (FIG. 50) of the rocker 290. The anvil shaft 272 also extends through aligned holes 301 in the upper parts of the U-spring legs 254 (FIG. 56). As a result, the U-spring 272 is substantially fixed in place with respect to the shell 200 by passage of the upper and lower shafts 272 and 240 therethrough and the rocker 290 (FIG. 57) is pivoted on the anvil shaft 272 for rocking forwardly and rearwardly (clockwise or counterclockwise in the drawing) about the anvil shaft 272.

As seen in FIG. 57, the forwardly and upwardly angled front end portion 258 of the U-spring 252 lies within the downward opening recess 294 of the rocker 290 and at its forward extremity (left extremity in FIG. 57) is fixed to the front wall 293 of the rocker 292 by any convenient means, such as by being molded integrally with the rocker 290. The U-spring 252 is arranged to resiliently urge the rocker 290 to its central, horizontal position shown in FIG. 57 and to resiliently resist, but permit, forward and rearward (in FIG. 57 counterclockwise and clockwise) rocking of the rocker 290 by the user.

The rocker 290 is pivotable forward (counter-clockwise in FIG. 57) to push the bottom edge of its front wall 293 down against irrigation lever front tab 247, correspondingly counterclockwise rotate the irrigation pinch lever 242, cause its pinch blade 245 to drop away from the corresponding irrigation hose 224I, and thus open the irrigation hose 224I, as in the transition from FIG. 53A to FIG. 53B. Alternately, the rocker 290 is pivotable rearward (clockwise in FIG. 57) to push the bottom edge of the rear wall 293 of the rocker 290 downward (clockwise) against the rear tab 247 of the suction pinch lever 243, correspondingly pivot same clockwise, drop its pinch blade 245 away from the corresponding suction hose 224S, and thus open the suction hose 224S, as in the transition from FIG. 56A to FIG. 56B.

Figure 48:
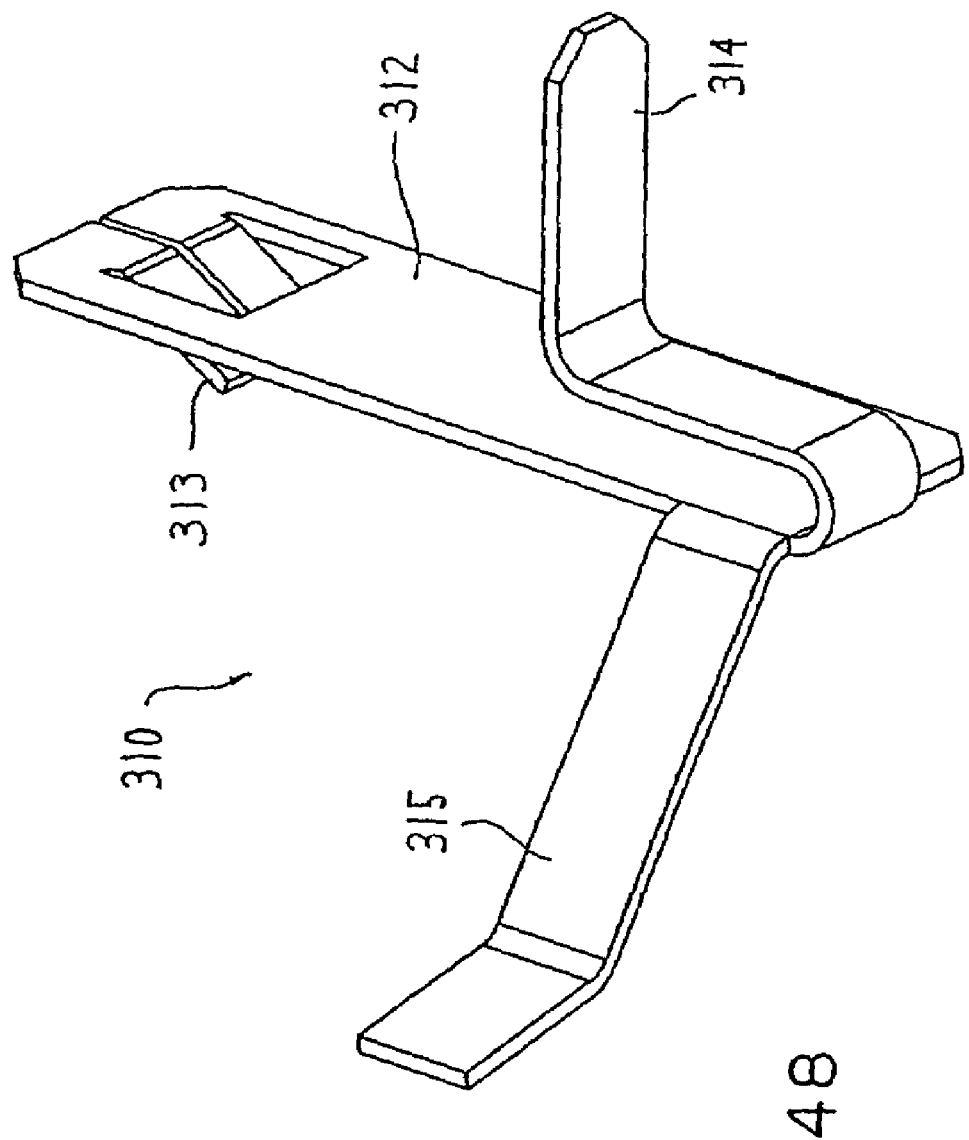
Figure 49:
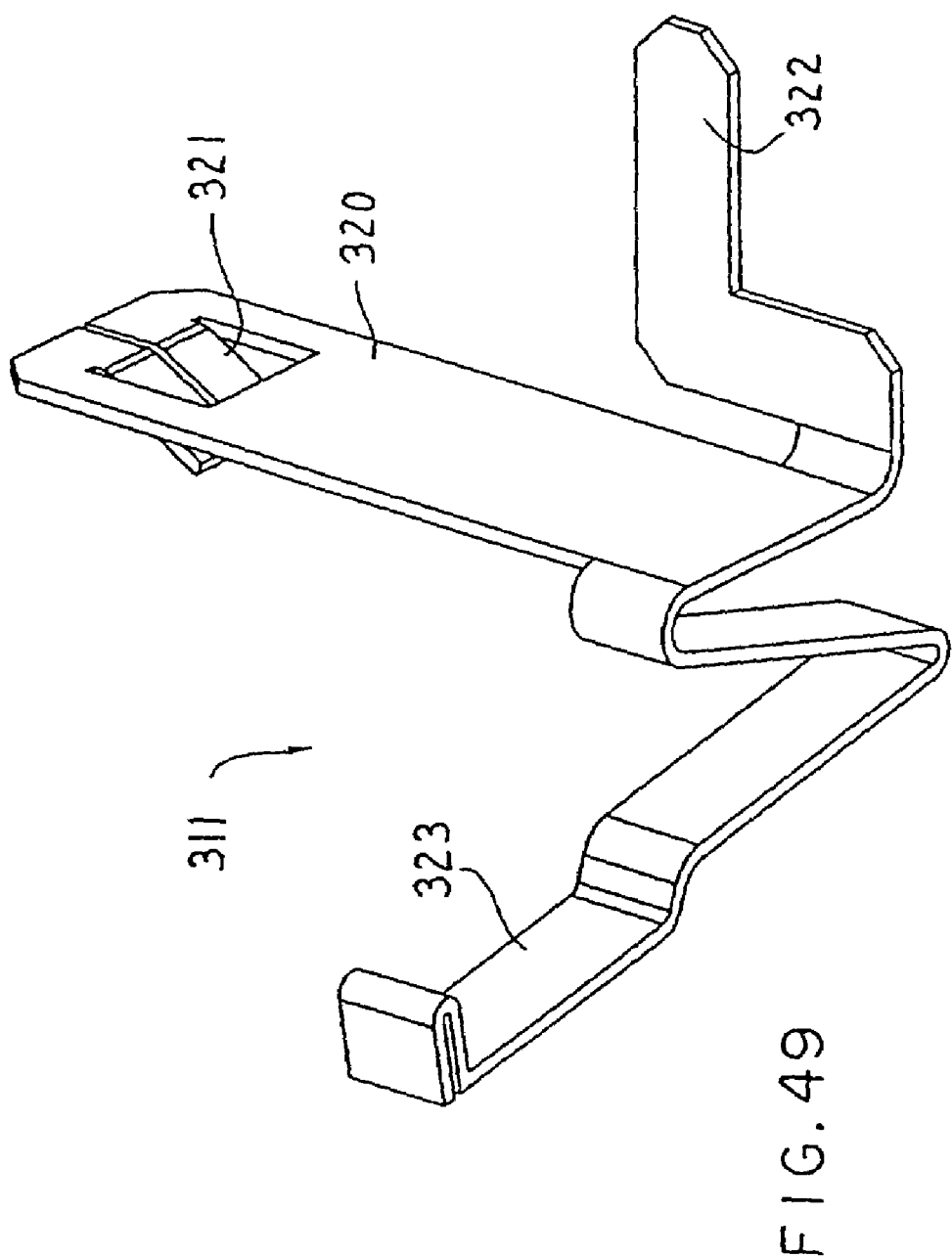
Figure 51:
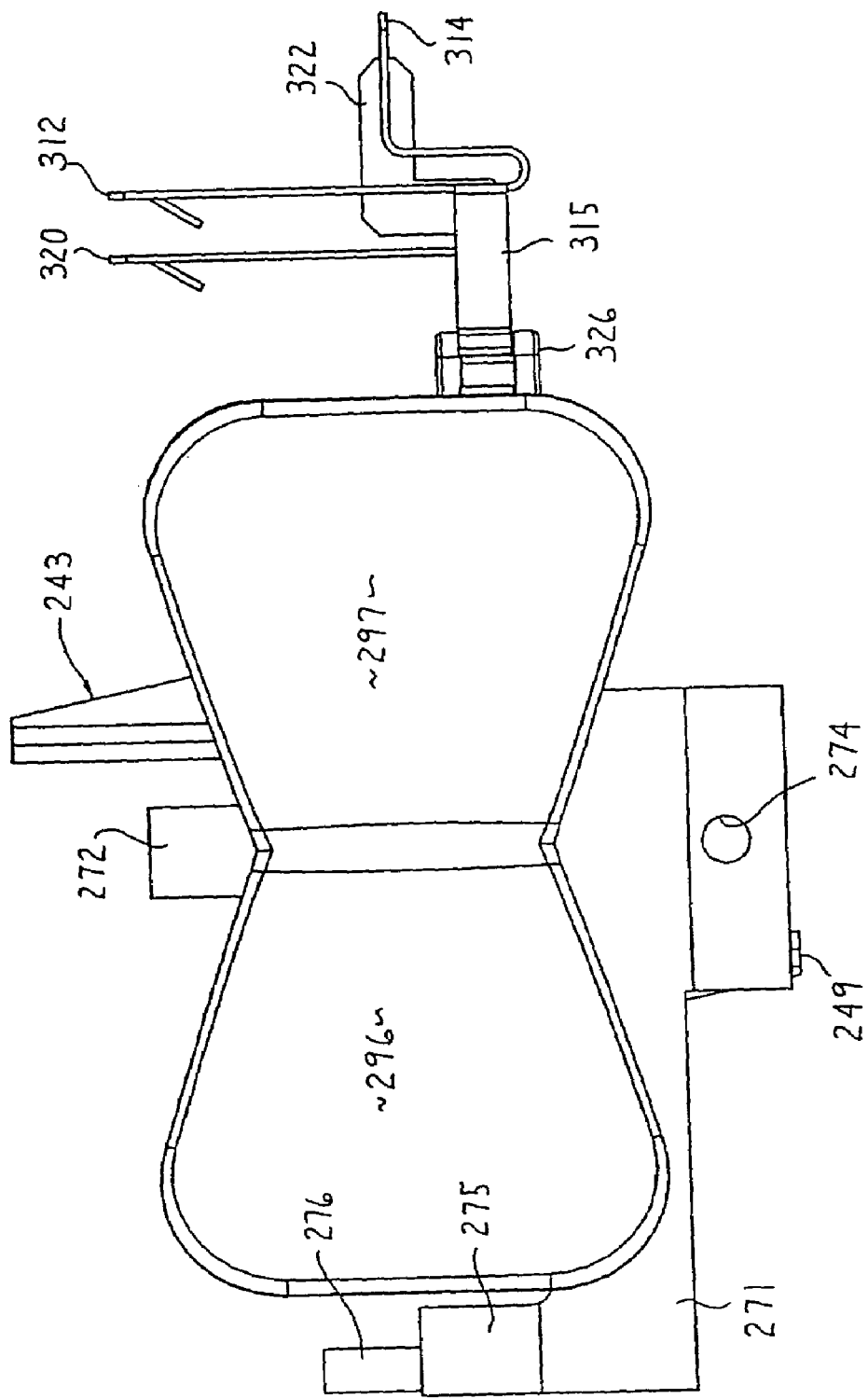
FIG. 51 is an enlarged top view of the FIG. 50 subassembly.

In the preferred embodiment shown, the electrical switch SW of the handpiece 26 is formed by a switch spring 310 and a Z-spring 311, seen in FIGS. 48 and 49 respectively. Both are formed of resiliently deflectable, electrically conductive, sheet metal. The switch spring 310 comprises a base plate 312 having a free end provided with gripper tabs 313 reflexly bent, a generally L profile female electric terminal 314 and a switch contact arm 315. Similarly, the Z-spring 311 (FIG. 49) comprises a base plate 320 whose free end is provided with gripper tabs 321, a generally L-shaped planar electric terminal 322, and a generally Z-shaped switch contact 323. The half shell 200S (FIGS. 37 and 38), to the rear of the tubular boss 241, comprises rear and front lateral recesses 325 and 324 respectively which open toward the opposite half shell 200I and are shaped to receive the gripper tab equipped, free end portions of the base plates 312 and 320 of the switch spring 310 and Z-spring 311, respectively. The switch spring and Z-spring are oriented so that their electric terminals 314 and 322 extend rearwardly (FIG. 57) and so that their switch contacts 315 and 323 respectively extend upwardly and forwardly. The top of the switch contact 323 is normally spaced slightly in front of the top portion of the switch contact 315. See also FIGS. 51 and 52.

Figure 59:
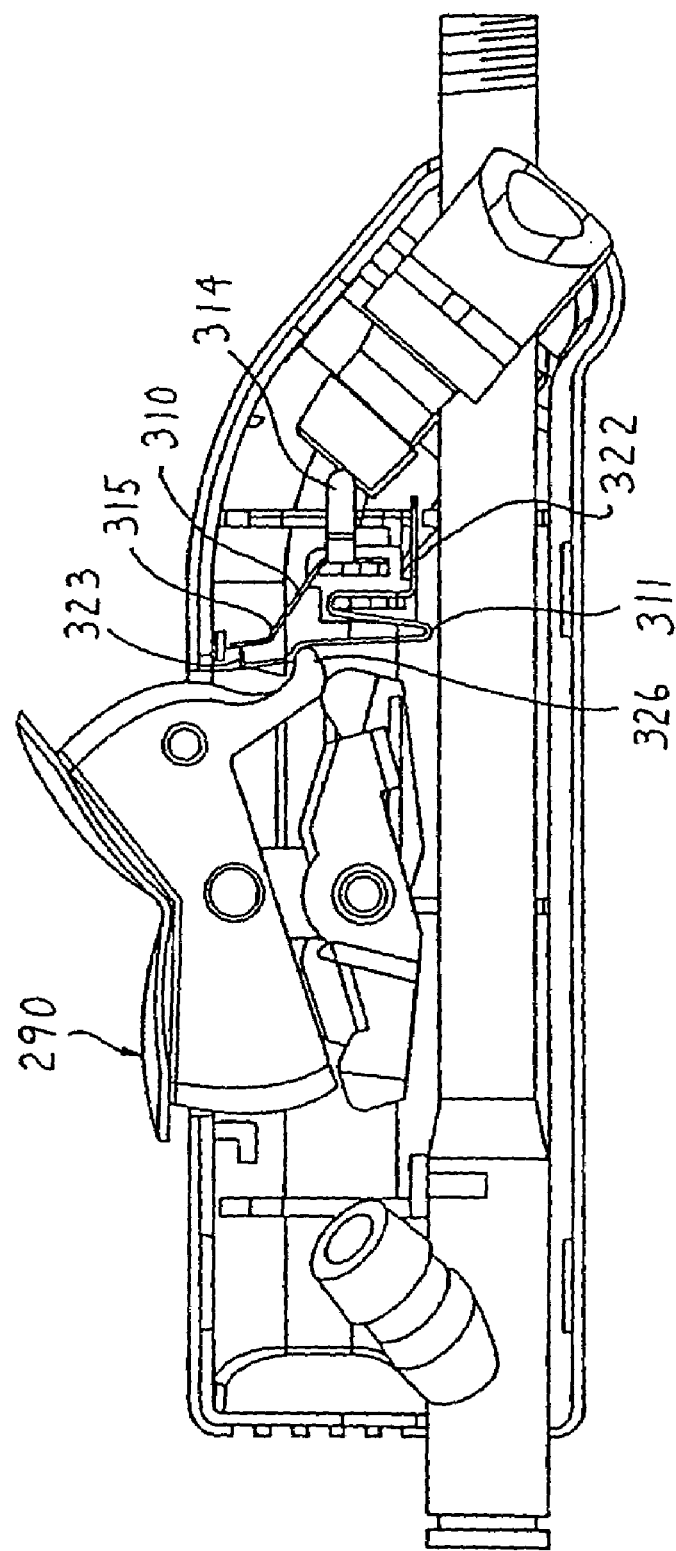
FIG. 59 is a view similar to FIG. 54 but with the guard pin entirely omitted and the rocker rocked forward in its irrigation tube open position (corresponding to FIG. 53B) and the switch contacts 323 and 315 engaged to close the battery/motor circuit and energize the motor for pumping irrigation liquid to the handpiece.

Fixed low on the rear of the rocker 290 and extending slightly rearward therefrom is a preferably integral switch actuator foot 326 (FIG. 53) arranged so that forward (counterclockwise) tilting of the rocker 290 not only opens the irrigation tube 224 by dropping the pinch blade 245 (in the transition from FIG. 53A to FIG. 53B), but also pivots the foot 326 (FIG. 59) upward and rearward, to push the switch contact 323 of the Z spring 311 rearwardly into electrical contact with the switch contact 315 of the switch spring 310. This closes the switch SW constituted by contacts 315 and 323, and, through their terminals 314 and 322, closes the electrical circuit (FIG. 22) through the motor M and array of batteries B to energize the motor and force irrigation liquid through the flexible irrigation hose 224I and then forwardly through the tip TP to a surgical site.

Figure 60:
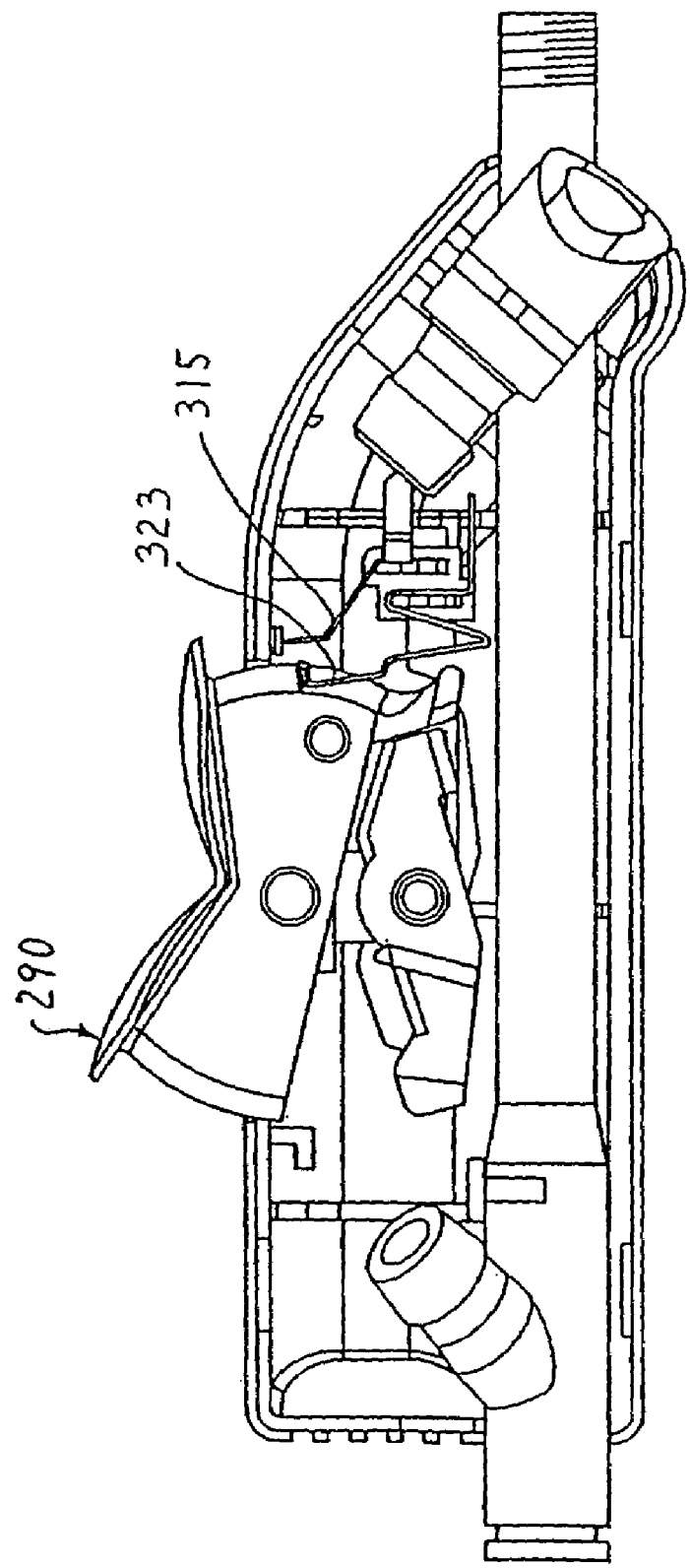
FIG. 60 is a view similar to FIG. 59 but with the rocker rocked backward to open the suction tube as schematically indicated in FIG. 56B.

On the other hand, rocking the rocker 290 rearward (clockwise in FIGS. 56 and 60) drops the pinch blade 245 of the suction pinch lever 243 to open the suction tube 224 (in the transition from FIG. 56A to 56B) to allow suction flow from the tip back to a suction source SS.

Note that only one of the pinchable hoses 224I and 224S can be opened at a time. Note also that opening of the irrigation hose 224I is automatically and positively correlated with closure of the switch SW, so as to begin pumping liquid forward through the open irrigation tube 224I.

To avoid closure of the switch SW (and resulting energization of the motor M, wear on the parts and depletion of the batteries), after the handpiece is assembled and prior to packaging for shipping, a guard pin 330 (FIG. 29) has its square cross-section, elongate shank 331 inserted rearwardly through a hole 332 in front wall 333 of the shell (FIGS. 27-29). The guard pin shank 331 (FIG. 58) extends through the front wall hole 332 rearward into the shell 200 snugly under the front and rear walls 293 of the rocker 290 to positively prevent pivoting of the rocker 290 and thereby preventing closure of the electric switch contacts 315 and 323. In addition, the guard pin shank 331 pushes downward, under their normal hose clamping positions, the tabs 247 of both pinch levers 242 and 243, so as to hold open and thus unstressed the hoses 224I and 224S during shipping and storage. FIGS. 53-58 show the parts in this storage position, with the guard pin shank 331 in solid line in FIG. 58 and in dotted line (to better show parts behind it in the drawings) in FIGS. 53-57. A shield 335 depends from the shank 331 near the ring 334 to partly cover and protect, during storage and shipping, the open front end of the conduit 210.

When the apparatus is ready for use, the guard pin 330 is withdrawn from the handpiece by forward pull on a finger ring 334 (FIG. 29) fixed on the front end of the shank 331.

Except for the springy conductive metal spring elements 252, 261, 310 and 311, and the resiliently pinchable hoses 224I and 224S, the remaining primary parts of the handpiece are formed of a suitable rigid material, by any convenient means, such as molding of a rigid plastics material.

While the operation of the disclosed apparatus will be clear from the above description, same may, for convenience, be briefly summarized as follows. To operate the disclosed apparatus, the inlet connector 12 of the pumping unit 11 is inserted in the corresponding fitting of an irrigation liquid supply (e.g. bag) IL and the pumping unit 11 is supported therebelow by means above discussed. The guard pin 330 is pulled from the handpiece 26. The tip TP of the handpiece 26 is inserted into a surgical site 813 in a patient, e.g. through a cannula CA previously inserted thereinto.

Rocking the rocker 290 forward to its FIG. 1 position opens the irrigation hose 224I (FIG. 29) and closes the contacts of the switch SW (FIG. 22), energizing the motor and rotating the pump rotor 117 (FIG. 6). Insertion of the pumping unit inlet connector 12 directly into the irrigation liquid bag 14 has substantially instantaneously primed the pumping chamber with irrigation liquid so that rotation of the pump rotor 117 substantially instantaneously pumps irrigation liquid under pressure through the tube 23 (FIG. 1) through the handpiece 26, namely through the adapter block 225 (FIG. 42), hose 224I, conduit 210 and tip TP to the surgical site SET. On the other hand, rocking the rocker 290 rearward (to its FIG. 60 position) closes the hose 224I and opens the hose 224S for suctioning debris from the surgical site through the tip TP, conduit 210, open suction hose 224S, adapter 225 and suction hose 33 to a conventional suction source SS. Release of the rocker 290 causes it to resiliently center itself in its neutral FIG. 27 position, in which both the suction and irrigation hoses 224S and 224I respectively are clamped closed by their respective pinch levers 243 and 242.

The disclosed suction irrigation system 10 is totally disposable and manufacturable at relatively low cost. Upon insertion of the inlet flow connector 12 into the irrigation liquid source IL, and pulling out of the guard pin 330, the system 10 is ready for immediate use. The system provides a high flow rate of irrigation liquid (higher than usual for a disposable system). The flow rate is steady so as not to make tissue jump at the surgical site, as might a pulsed irrigation system. Location of motor, pump and batteries remotely from the handpiece, adjacent the irrigation liquid source IL, not only provides for substantially instantaneous priming of the pump but also permits a compact, very lightweight, and hence readily maneuverable handpiece 26.

In one unit built according to the invention, the connector 13 (FIGS. 1 and 1A) on the liquid supply container 14 was a conventional luer female fitting. The liquid inlet connector 12 was provided with an annular rib 12A (FIGS. 1, 2 and 4-6) adjacent its upper end to snapfit into the bag fitting 13 forcibly enough to support the weight of the pumping unit 11 (and its trailing hose 23 and cable 27) pendently from the container 14, yet allow the pumping unit 11 to be intentionally disconnected from the container 14 by pulling same apart more forcibly. Thus, the pumping unit 11 with its trailing hose 23 and cable 27 can be entirely supported pendently from the liquid supply container 14 by connection of its hollow spike 12 to the container fitting 13, or can instead be supported by separate means, exemplified by the bracket 18 of FIG. 1.

Modification

FIG. 61 and onward disclose a modified handpiece 26D. In some instances, parts of the modified handpiece 26D will carry the same reference numerals as corresponding parts of the above described handpiece 26 with the suffix D added thereto.

It will be understood that the handpiece 26D may be used in a variety of orientations, for example in the FIG. 61 orientation, in an orientation turned upside down therefrom as in FIG. 69, or in other orientations as desired and convenient. However, for convenience in reference, in the present discussion the words "top" and "bottom" shall refer to the handpiece 26D in its orientation of FIG. 61.

The handpiece 26D comprises a shell 400. The shell 400 preferably includes an inverted tub 401. The shell 400 preferably is a one-piece molded rigid plastic element. The inverted tub 401 comprises upstanding, front and rear valve barrels 402 and 403 laterally spaced from each other and joined by preferably tangent side walls 404 and 405 (FIG. 67). The inverted tub 401 further includes a top wall 410 which closes the top of the inverted tub 401 and extends between the barrels 402 and 403 and side walls 404 and 405 (FIGS. 67 and 70). Top extensions 411 and 412 of the front and rear valve barrels 402 and 403 respectively extend up past the top wall 410. A pair of switch carrier plates 413 and a further pair of switch carrier plates 414 (FIGS. 72 and 73) depend from the top wall 410 into the downward opening cavity 415 of the inverted tub 401. The plates 413 and 414 are parallel to each other and preferably parallel to the side walls 404 and 405. The plates 413 and 414 are spaced inboard from the side walls 404 and 405 respectively. The plate pairs 413 and 414 are spaced apart on opposite sides of the common diametral plane of the barrels 402 and 403.

Relatively narrow switch mounting gaps 420 and 421 laterally space apart the respective complete pairs 413 and 414 (seen for example in FIG. 73). A hole 422 (preferably T-shaped as in FIGS. 67 and 73) opens through the top wall 410 into the cavity 415 of the inverted tub 401. The cross-head portion of the T lies close adjacent the top extension 411 of the front valve barrel 402 and the leg of the T extends rearward therefrom and overlies the switch mounting gap 420 (FIG. 73) in vertical alignment therewith.

The shell 400 includes an elongate rigid conduit 430 (FIG. 61) which is preferably integrally molded in the tub side wall 404 adjacent the top thereof (here substantially flush with the top wall 410). The conduit 430 extends forwardly and rearwardly beyond the inverted tub 401, as seen for example in FIGS. 61 and 71 and has front and rear end portions 431 and 432 spaced from the inverted tub 401. In the preferred embodiment shown, the front end portion 431 of the conduit 430 is radially enlarged and carries an annular seal ring groove 434 (FIGS. 70 and 70A) for receiving a resilient seal ring (e.g. an O-ring 437) and an externally threaded front end extremity 435 for sealed, releasable, telescoped attachment thereon of an elongate tubular tip TPD of any desired type for suction, irrigation or other use at a surgical site. In the preferred embodiment shown, the radially enlarged rear end portion 432 of conduit 430 is internally threaded at 436 (FIG. 70) for alternative reception therein of an externally threaded closure plug 440 (FIGS. 61 and 63) or a suitable surgical tool (not shown). The closure plug 440 preferably is provided with an annular seal, such as an O-ring 442 (FIG. 63), behind its externally threaded front extremity 443 for sealing the rear end of the conduit 430 against fluid leakage, when threadedly inserted into the rear end portion 432 of the conduit 430.

As seen in FIG. 70, the conduit 430 has a through passage 441 axially, and preferably coaxially, extending therethrough and opening through the front and rear end portions 431 and 432. Suitable surgical tools (not shown) may be inserted forwardly through the rear end portion 432 or rearwardly into the front end portion 431 of the conduit 430. Such surgical tools may include ones of the type having substantially coaxial inner and outer parts, wherein the inner part may be received in the through passage 441 and the outer part may be threaded onto the externally threaded front extremity 435 in a conventional manner, and in place of a tip TPD. The conduit 430 alternately will also accommodate surgical tools (not shown) of the type having a portion similar to the plug 440 with a forward extending portion (not shown) insertable forwardly through the through passage 441 and the conduit 430 toward a surgical site. In addition, it is contemplated that the front end portion 431 and rear end portion 432 of the conduit 430 may be provided with removable adaptors (not shown) to present an external thread adjacent the rear end portion 432 and/or an internal thread adjacent the front end portion 431, should it be desired to use an externally threaded tip in place of the tip TPD of FIG. 61 or an internally threaded tool portion adjacent the rear end portion 432 of the conduit 430. Alternately, adaptors, not shown, may be threaded onto the front end portion 431 and/or into the rear end portion 432 for the purpose of providing a non-threaded connection of a tip or tool thereto.

The shell 400 further includes integral irrigation liquid and suction fittings (or nipples) 450 and 451 respectively (FIGS. 61, 68 and 70), which extend generally rearwardly at an acute angle (here about 22° and preferably between 15° and 30°) to the side wall 405 of the inverted tub 401 and conduit 430. The fittings 450 and 451 have respective coaxial through passages 452 and 453 respectively, whose central length axes are parallel to each other and are coplanar with the central length axis of the conduit 430. The central through passages 452 and 453 extend coaxially, and generally forwardly, from the nipples 450 and 451 respectively, just below the top wall 410 of the inverted tub 401, and perpendicularly across the valve barrels 402 and 403 respectively, and have forward ends into the central through passage 441 of the conduit 430. The central length axes of the irrigation and suction passages 452 and 453 perpendicularly intersect respective upstanding length axes of upstanding coaxial through openings 454 and 455 respectively of the front and rear valve barrels 402 and 403 respectively (compare FIGS. 70 and 70, for example). The nipples 450 and 451 thus communicate through the upstanding central through openings (or valve bores) 454 and 455 respectively of the front and rear valve barrels 402 and 403 respectively, and thereacross with the central through opening of the conduit 430. Such communication is controlled by valve bodies hereafter described.

The nipples 450 and 451, as can be seen from the drawings, are on the opposite side of the inverted tub 401, from the conduit 430. Thus, as above discussed with respect to FIG. 70, the nipples 450 and 451 are separated laterally from the conduit 430 by the common central plane of the valve barrels 402 and 403 (such common central plane of the valve barrels 402 and 403 being defined by (containing) the upstanding central axis of the valve bores 454 and 455 of the valve barrels.

In the preferred embodiment shown, the front valve barrel 402 is intended to control irrigation liquid flow from the nipple 450 to the conduit 430 and the rear valve barrel 403 is intended to control suction flow from the conduit 430 to the nipple 451. Accordingly, the nipples 450 and 451 are respectively adapted to connect to a suitable irrigation liquid source and suction source respectively. Conveniently then the irrigation liquid nipple 450 is connectable through an irrigation liquid tube 23D supplied by a pump 11D from an irrigation liquid source IL, as described above with respect to the embodiment of FIG. 1 in respect to the irrigation liquid tube 23, pump 11 and irrigation liquid source IL. Similarly, the suction nozzle 451 is connectable through a suction tube 33D to a suction source SS, as above discussed with respect to the embodiment of FIG. 1 in respect to the suction tube 33 and suction source SS. The front and rear valve barrels 402 and 403 may thus be referred to as the irrigation liquid and suction valve barrels respectively.

The handpiece 26D (FIG. 63) includes axially shiftable valve members 460 and 461 (FIG. 63) respectively cooperable with the valve barrels 402 and 403 to accommodate the respective valve members 460 and 461, the valve bores 454 (FIG. 70) and 455. The valve bores 454 and 455 each include a bottom cylindrical guide portion 462 (FIG. 70), surmounted by an upward tapered valve seat 463, and in turn surmounted by a narrower cylindrical valve guide portion 464. A radially enlarged cylindrical bottom opening recess 465 communicates between the bottom cylindrical guide portion 462 and the bottom of the inverted tub 401, as seen in FIG. 70.

The irrigation liquid and suction through passages 452 and 453 pass through and are spaced from the top and bottom of their respective upwardly tapered valve seats 463 and are thus spaced below the corresponding narrowed cylindrical valve guide portion 464 and are spaced below their respective narrowed cylindrical valve guide portions 464.

Figure 63:
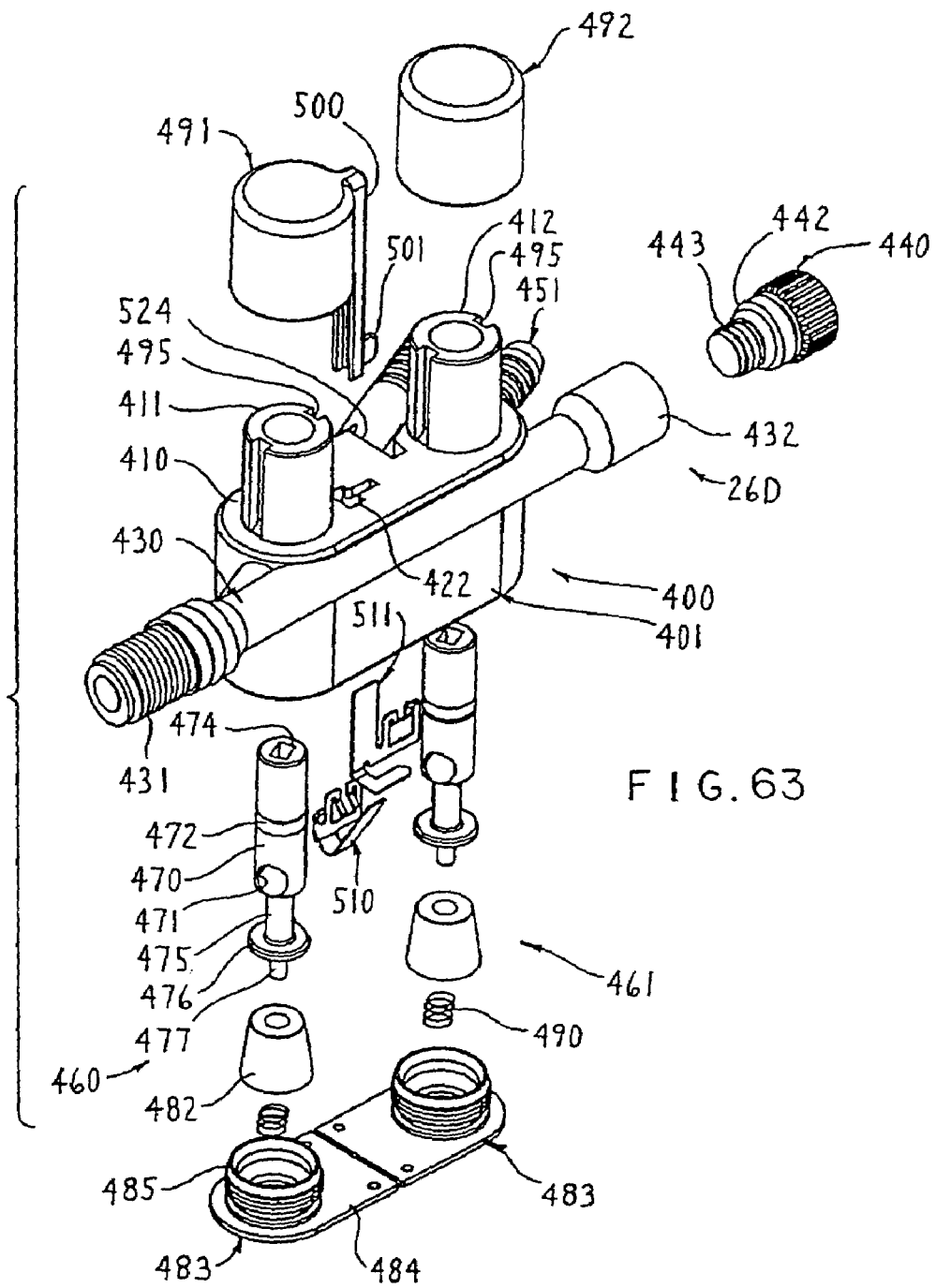
FIG. 63 is an exploded pictorial view of the FIG. 61 handpiece taken from the top, front and right side thereof.

As seen in FIG. 63, each valve member 460 and 461 comprises an elongate cylindrical valve piston 470 pierced at its bottom end by a diametral fluid hole 471 and having at about mid-height an annular groove 472 for receiving an annular seal (conveniently an O-ring) 473 (FIG. 66). A coaxial multi-sided (here rectangular) top hole 474 (FIG. 63) indents the top of each piston 470. A preferably cylindrical rod 475 coaxially depends from each piston 470. A coaxial radially outwardly extending annular flange 476 is fixed at the bottom of each rod 475. A spring guide tail 477 coaxially depends from each radial flange 476, and also serves as a stop for the corresponding piston 470 at the bottom of its axial travel as seen in FIG. 67.

Each valve member 460 and 461 further includes a hollow, resilient, upward tapering, preferably frustoconical valve closure element 482 (FIG. 63) snugly fixed on the corresponding rod 475 between the bottom of the corresponding piston 470 and the top of the radial flange 476, as shown in the assembled condition of the valve member (for example the suction valve member 460 and 461) in FIGS. 66 and 67.

The open bottom of the inverted tub 401 and the bottom opening recesses 465 (FIG. 70) are closed by a bottom closure, here comprising a laterally opposed pair of bottom plugs 483 (FIG. 63). The bottom plugs 483 are preferably identical and each comprises a generally D-shaped closure plate 484 and an upward opening cup 485 fixedly upstanding integrally from the rounded end of the corresponding D-shaped closure plate 484. In the assembled apparatus, the open bottom of the inverted tub 401 is closed by the closure plates 484 of the respective front and rear bottom plugs 483, and the cups 485 are snugly and sealingly telescoped in and close the open bottoms of the respective front and rear barrels 402 and 403, as generally indicated in FIGS. 63, 67 and 62. Thus, in the embodiment shown, the bottom of the tub 401 is closed (but need not be sealed) by the plates 484, whereas the bottoms of the front and rear valve barrels 402 and 403 are plugged and sealed by the respective cups 485 of the bottom plugs 483. The bottom plugs 483 may be, and preferably are, permanently fixed in the bottom portion of the inverted tub 401 by any convenient means to trap within the valve barrels the valve members 460 and 461 and trap within the open central portion of the inverted tub 401 electrical contact structure hereafter described. Permanent entrapment of the valve members 460 and other structure within the inverted tub 401, due to permanent fixation of the bottom plugs 483 to the open underside of the tub 401 is preferred when the handpiece 26D is a single use disposable item, as intended, rather than a multiple use device requiring sterilization between uses.

In the preferred embodiment, sealing of the bottom of each barrel 402, 403 is by pressfitting therein of the corresponding cup 485, which pressfitting also serves to fix the bottom plugs 483 to the inverted tab 401.

Optionally, as shown in FIG. 67A, as a backup, or an alternative, the outside of the cup 485, at a location spaced between its top and bottom ends, may be externally annularly grooved to receive an annular resilient seal, preferably a conventional O-ring 486 (FIG. 67A), wherein the O-ring 486 assists or provides such sealing. While such press fitting is preferred, the bottom plugs 483 may be fixed to the inverted tub 401 in other ways, for example by sonic welding, adhesive bonding, or the like. Alternately, if desired, the bottom plug pair 483 can be combined into one single port.

Each of the valve members 460 and 461 is resiliently urged into its upper, closed position (shown for example with respect to the front, irrigation liquid valve member 460 of FIG. 66) by a corresponding coil compression spring 490 (FIG. 67). In both of the valve members 460 and 461, the coil spring 490 is backed at its lower end by the corresponding bottom plug 483. Thus, each spring 490 radially loosely sits in its cup 485. The upper end portion of each spring 490 telescopes coaxially on the depending spring guide tail 477 and abuts the underside of the radial flange 476 of the corresponding valve member 460 or 461. The springs 490 thus urge the valve members 460 and 461 to their closed (upper in FIG. 67) positions disconnecting the corresponding one of nipples 450 and 451 from the conduit 430.

Front and rear (here irrigation liquid and suction, respectively) inverted cup shaped push buttons 491 and 492 are coaxially fixed to the top of the corresponding front and rear valve pistons 470 (FIGS. 63 and 66). A hollow, rectangular cross section, preferably integral stem 493 fixedly depends coaxially from the top wall 494 (FIG. 78) and down into the hollow interior of each inverted cup-shaped push button. Each stem 493 depends partway, here about halfway, through the height of the inverted cup shaped push button 491 and 492 and is of non circular (in the preferred embodiment shown rectangular) cross section for snug, non-rotatable fixed reception in the preferably corresponding cross-section, multi-sided top hole 474 in the corresponding valve piston 470 (FIG. 63). In this way, each valve piston 470, and hence its diametral fluid hole 471 are circumferentially fixed with respect to the corresponding one of the manual actuable push buttons 491 and 492. The push buttons 491 and 492 may be fixed to the tops of their respective valve pistons 470 by any convenient means such as adhesive bonding, press fit, or the like.

The push buttons 491 and 492 are snugly but axially reciprocatingly telescoped over the upstanding top extensions 411 and 412 (FIG. 63) of the shell 400. As can be seen from FIG. 63, 66, 77 and 74, the upstanding, telescoped radially opposed sides of each top extension 411, 412 and its corresponding push button 491, 492 are of constant diameter (cylindrical) through its height for snug reciprocating movement of each push button 491, 492 on its corresponding upstanding top extension 411, 412. The height of the top extensions 411, 412 and push buttons 491, 492 are about the same, as seen in FIG. 66. Each corresponding valve piston 470 in its uppermost, rest, closed position shown in FIG. 66 protrudes up beyond the top of the corresponding top extension 411 or 412, such that with the corresponding valve piston 470 in its uppermost position as in FIG. 66, the corresponding inverted cup-shaped push button 491, 492 is about half telescoped over the corresponding top extension.

The upstanding top extensions 411 and 412 (FIG. 63) each have at least one upstanding guide groove 495 extending the height thereof and axially slidably receiving a corresponding guide rib 496 (FIGS. 74 and 77) fixed, preferably integrally, on the interior of the side wall of the respective push button 491 and 492 for positively preventing rotation of each push button 491 and 492 on its upstanding top extension 411 and 412 respectively as the push button moves up and down axially along such top extension. The ribs 492 preferably extend the entire height of the corresponding push buttons 491 and 492 and are complimentary in size and cross sectional shape to the corresponding guide grooves 495 to allow free relative axial movement but preclude relative circumferential movement as between the push buttons and top extensions. Thus, the axial guiding of the ribs 492 in the grooves 495 keeps the valve pistons' diametral fluid holes 471 aligned with the corresponding irrigation liquid and suction through passages 452 and 453 respectively of the nipples 450 and 451 respectively. In the preferred embodiment shown, diametrally opposed pairs of guide grooves 495 on each top extension and diametrally opposed pairs of ribs 496 on each push button are provided. Also in the preferred embodiment shown, the two pairs of guide grooves 495 on the top extensions 411 and 412 are coplanar, and hence lie on the common central plane of the top extensions 411 and 412 and inverted tub 401.

To the extent above described, the push buttons 491 and 492 are preferably identical. However, the front (irrigation liquid) push button 491 is additionally provided with a switch actuating leg 500 preferably molded in the outer surface of its side wall. Such actuating leg 500 extends down the height of the push button 491 and thence downward beyond the bottom edge of the pushbutton 491 in the manner shown in FIG. 63. At least the dependent portion of the switch actuating leg 500 is of constant cross section and is shaped and sized and located circumferentially of the front push button 491 to be smoothly vertically reciprocatingly received down into the cross head portion of the T-shaped hole 422 (FIG. 68) in the top wall 410 of the inverted tub 401. As seen in FIGS. 68 and 77, the T-shaped hole 422 and switch actuator leg 500 are offset slightly sideways from the common central plane of the top extensions 411 (marked by the corresponding section line in FIG. 68).

In the embodiment shown, the depending portion of the switch actuating leg 500 is conveniently of U-shaped cross section as seen in FIG. 77.

Fixed, preferably integrally, to the bottom portion of the leg 500 and protruding rearwardly therefrom is a switch contact separating ridge 501. The hole 422 continues as a shallow downwardly extending groove 502 in the portion of the forward valve barrel 402 facing into the interior of the inverted tub 401. As seen in FIG. 73, such groove 502 helps guide longitudinal reciprocation of the switch actuator leg 500 inside the inverted tub 401.

An electrical switch like that indicated schematically at SW in FIG. 22 of the prior embodiment is provided for actuation to energize a pump motor like that shown on at M in above FIG. 22 from batteries such as indicated at B therein. In the present FIG. 61 embodiment, such switch SW comprises a pair of switch elements 510 and 511 (FIGS. 63, 79, 80 and 72C) of electrically conductive springy sheet metal, such as copper or a suitable alloy.

The switch element 510 (FIG. 80) comprises a base plate 512 provided with gripper tabs 513 acutely angled with respect thereto. The switch element 510 further includes an electric connector terminal 514 and a switch contact leaf 515. The switch element 511 is of somewhat different shape, but includes a base plate 520 (FIG. 79) including gripper tabs 521 acutely angled with respect thereto, and an electric connector terminal 522 and switch contact leaf 523 extending therefrom.

The switch element 510 is fixed in the interior of the inverted tub 401 as follows. The base plate 512 is slidably inserted upward in the orientation of FIG. 63 into the switch mounting gap 421 (FIGS. 72C and E) between the depending switch carrier plates 414. The gripping tabs 513 enter and become jammed in the switch mounting gap 421 to prevent the switch element 510 from accidently leaving its operative position of FIGS. 72C and E, within the inverted tub 401. This leaves the electrical connector terminal 514 and switch contact leaf 515 outside the switch mounting gap 421. The electrical connection terminal 514 lies between the outboard switch carrier plate 414 and the side wall 403 of the inverted tub 401. The switch contact leaf 515 is resiliently self-urged toward the switch carrier plates 413 as more fully discussed hereafter.

The base plate 520 of the switch element 511 is inserted upward into the switch mounting gap 420 (FIGS. 72C and E) and is frictionally fixed therein by engagement of the gripping tabs 521 with the opposed inboard switch carrier plate 413. The electrical connector terminal 522 is disposed between the outboard switch carrier plate 413 and the inverted tub side wall 404 adjacent the bottom of the outboard side wall 413. The switch contact leaf 523 extends upward along the outboard switch carrier plate 413 within the switch mounting gap 420 and into electrical contact with the switch contact leaf 515 of the switch element 510 to complete an electrical connection between the two switch elements 510 and 511.

Wires 103 of cable 27 (FIG. 22) from the pump motor M are indicated at 103D in FIG. 72C and are lead into the inverted tub 401 through an opening 524 (FIG. 61) in the top wall 410 of the inverted tub 401. The wires 103D, suitably insulated, terminate within the inverted tub 401 in conventional connectors 525 compatible with the electrical connector terminals 514 and 522, respectively. In the preferred embodiment shown, the connectors 525 are of resilient female type telescopingly fixable on the electrical connector terminals 514 and 522. In this way, the FIG. 72C electrical contact between the leaf 515 and leaf 523 acts as a switch SWD (FIG. 72C) usable in place of the switch SW (FIG. 22) and which upon closure energizes the motor M from the battery B.

The thus established electrical contact between switch contact leaves 515 and 523 is permitted with the switch leaf separator 501 pressed down, by pushing downward the corresponding button 591 to its lowermost position (from its upper position in FIGS. 66, 72C and 72E. Upon manual release of the push button 591, it is raised by spring 490 to its upper position shown in FIG. 61, thereby raising the switch leaf separator ridge 501 to its dotted line position in FIG. 72D, E, thereby pushing the switch contact leaf 515 out of contact with the leaf 523 and into its dotted line position shown at 515' and opening the switch to a position like that of the switch SW FIG. 22, thereby disabling the pump motor M. Note that the inboard switch carrier plate 413 is recessed at 526, in the upper portion of its edge facing the vertically shiftable switch actuating leg 500, to provide room for up and down motion of the switch leaf separator ridge 501.

The handpiece 26D (FIG. 63) may be assembled as follows. The assembled valve members 460 and 461 (including elements 470-477, 482 and 490) are inserted up into the open bottoms of the respective front and rear valve barrels 402 and 403 and temporarily held in place therein by any convenient means not shown. The push buttons 491 and 492 are then fixed atop the upward protruding valve pistons 470 by any convenient means, as shown with respect to valve push button 491 and FIG. 66, for example.

The slide on connectors 525 (FIG. 72C) then fixed on the electric connector terminals 514 and 522 of the corresponding switch elements 510 and 511 (FIGS. 72C and E).

The free ends of the insulator wires 103D are lead up into the central portion of the downward opening cavity 415 of the inverted tub 401 and up through the opening 524 (FIG. 63) and the top wall, 410 of the inverted tub 401 and extend therefrom toward the remote pressure liquid unit, like the insulated wires 103 from the handpiece 26 of FIGS. 1 and 22, for connection to the motor M and battery B in the manner of FIG. 22.

The forward (irrigation liquid) push button 491 is then preferably pushed down (to its valve open position) to position the switch leaf separation ridge 501 in its lowest position, shown for example in FIGS. 72D-E. With the switch contact leaf 515 bent more closely toward its corresponding base plate 512, to clear the switch carrier plates 413 (for example to the position 515" shown in chain line in FIGS. 72-73), the switch element 510 can be slid upward into its installed position in the inverted tub 401, with its base plate 512 and gripping tabs 513 trapped in the switch mounting gap 421 between the switch carrier plates 414. The free upper end of the switch contact leaf 515 slides on past the pad 527 and downwardly positioned switch leaf separator ridge 501 whereafter the switch contact leaf 515 can be released to resiliently bend away from the switch carrier plates 414 into substantially its solid line position shown in FIG. 72E. Similarly, the switch element 511 can be installed by inserting its base plate 520, gripping tabs 521 and switch contact leaf 523 upward into the switch mounting gap 420 between the switch carrier plates 413, to its FIG. 72E installed position, with its switch contact leaf 523 extending up past and being electrically conductively and forcibly pressed against by the upstanding free end of the switch contact leaf 515, as shown in FIG. 72E.

With the valve members 460 and 461 and switch elements 510 and 511 thus installed within the inverted tub 401, the bottom plugs 483 can then be fixed in place (in the manner above described with respect to FIGS. 66 and 67) to close bottom of the shell 400. The irrigation liquid and suction tubes 23D and 33D can then be fixedly telescoped over the nipples 450 and 451 respectively of the handpiece 26D to thereby, as schematically indicated in FIG. 70, connect the nipples 450 and 451 to the irrigation liquid pump 11D and suction source SS.

A hollow suction/irrigation tip TPD of any conventional type may be fixed, sealingly, to the front end portion 431 of conduit 430 (as in FIG. 61). The rear end of the conduit 430 can be closed by means such as the closure plug 440.

Pushing down the suction button 492 opens the connection from the suction nipple 451 (and hence suction source SS) to the conduit 430 and tip TPD and thereby to a surgical site into which the tip TPD may be inserted for suction of loose material from a surgical site to the handpiece 26D back to the suction source SS. Further depression of the suction push button 492 progressively opens the suction path between the interior of the conduit 430 and suction nipple 451, by bringing the valve diametral fluid hole 471 into progressively more complete communication with the interiors of the suction nipple 451 and conduit 430, the fully opened position of the suction valve member 461 being shown in FIG. 67. Release of manual pressure atop the suction push button 492 allows the spring 490 to urge the suction valve member 461 from its FIG. 67 open position upward to a closed position comparable to that of the valve member 470 in FIG. 66.

In substantially the same way pushing down the irrigation liquid push button 492 from its upper, closed position of FIGS. 66 and 67 progressively opens the irrigation liquid valve. A full depression of the irrigation liquid push button 491 fully opens the irrigation liquid flow path between the irrigation liquid nipple 450 and conduit 430. In addition, the irrigation liquid valve member 460 and push button 491 in their closed, upper position shown in FIG. 66, locate the switch leaf separator ridge 501 in its upper, dotted line position at 501' in FIGS. 72D and E, so as to separate the switch leaf 515 and 523 and prevent energization of the pump motor M (FIG. 22) from the battery B. However, when the irrigation liquid push button 491 is pushed downward it downwardly displaces the corresponding irrigation liquid valve member 470 to progressively open the irrigation liquid path from nipple 450 to conduit 430 and tip TPD, and also downwardly shifts the switch leaf separator ridge 501 from its dotted line position 501' to a solid line position (at the bottom of its travel) shown in solid line FIGS. 72D-E, thereby allowing the springy switch contact leaf 515 to resiliently bend itself forcibly into electrically conductive contact with the fixed switch contact leaf 523, as shown in FIGS. 72C and E, to thereby close the switch SWD and provide an electric current path therethrough to energize the pump motor M from the battery B in the manner shown in FIG. 22.

As the irrigation path through the irrigation liquid valve member 470 starts to open, the switch SWD turns on the pump motor to supply liquid to the valve member 470.

The diametral fluid hole 471 in each valve piston 470 is preferably slightly widened lengthwise of the valve member (vertically in FIG. 63), to maximize flow through the hole 471 in the open position of the valve, by keeping the flow path through the piston 470 fully open, despite the axial stack-up of tolerances in each valve unit 460, 491 and 461, 495. In one unit constructed according to the invention, the minimum and maximum diameters of each diametral fluid hole 471 were 0.190 inch and 0.220 inch respectively, the greater diameter of the hole 471 thus being about 15% greater than the minimum diameter of thereof. See for example, FIG. 65.

The conduit 430 and any desired tip TPD thus preferably are used for both suction and irrigation liquid flow.

All the parts of the apparatus above described are preferably molded, substantially rigid, plastics material of conventional type, except as otherwise described, e.g. the switch elements 510 and 511 of electrically conductive springy metal and the annular seals 473 and 482 and 486 of conventional resilient rubber-like material and the wires 103D and connectors 525.

Instead of the closure plug 440 (FIG. 63) the rear end portion 432 of the conduit 430 can instead be advantageously equipped with a one piece, molded, resilient, rubber-like cap unit 530 (FIG. 81). The cap unit 530 comprises a cup like body 531, opening forwardly (leftwardly in FIGS. 81 and 82), and which comprises a bottom wall 532 and cylindrical side wall 533 extending forward therefrom. The cap unit is sized to slide forwardly and telescopingly over the enlarged diameter rear end portion 432 of the conduit 430 to close the rear end thereof. The forward open end of the cap unit includes a semi-circular cross section radially inward projecting lip 534 sized to project radially inward slightly with respect to the outside diameter of the enlarged rear end portion 432 of the conduit 430 and to be positioned slightly forward thereof to prevent unintentional rearward removal of the cup unit from the conduit 430. However, the resilience of and inside diameter of the lip 534 allows it to stretch slightly diametrally to permit resilient snap fit installation and removal of the cap unit with respect to its FIG. 82 position covering the enlarged rear end portion 432 of the conduit 430. An integral elongate flexible strap 540 extends outward substantially radially from the lipped front end of the cap unit and adjacent its outer end carries a resiliently stretchy loop 541. The strap 540 and loop 541 may be referred to as the "lasso". Prior to sliding the cap unit onto the enlarged rear end portion 432 of the handpiece conduit 430, the strap 540 is bent and the loop 541 of the lasso is pulled forwardly snugly over the enlarged rear end portion 432 of the conduit 430, slightly circumferentially stretching the loop 541, in the process, until the loop 541 reaches the portion of the conduit 430 head of the enlarged rear end portion 432 thereof. In this way, the lasso maintains the cap unit captively tied to the rear end portion of the handpiece conduit 430 should the user wish to completely open the rear end of the conduit 430 by removing the cap unit, namely by sliding the cap unit rearwardly off the enlarged rear end portion 432 of the conduit 430. Thus, the cap unit cannot be lost or misplaced but rather remains conveniently at hand for later telescoping onto the rear end portion of the conduit 430. Sizing the internal diameter of the loop 541 slightly smaller than the external diameter of the enlarged rear end portion 432 of the conduit 430 assures that the loop 541 will not accidentally fall off the rear end portion of the conduit 430. Axial room is provided between the enlarged rear end portion 432 of the conduit 430 and the inverted tub 401 of the handpiece to accommodate both the loop 541 and the lip 534 of the cup like body 531.

A coaxial column 544 projects integrally from the rear end wall of the cup like body 531, preferably more than half the depth of the cup like body 531, with an annular space radially between the outside of the column 544 and inside of the side wall of the cup like body 531. The column 544 has a smooth cylindrical periphery of diameter to interfere slightly with the internal threads of the enlarged rear end portion 432 of the conduit 430 such that the column 544 is a friction fit within the enlarged rear end portion 432 of conduit 430, tending to hold the cup-like body 531 firmly fixed with respect thereto against accidental removal and yet allow the user to pull the cup-like body 531 off the rear end of the handpiece conduit 430 at will. Note that the column 544 does not thread into or unthread from the internal threads 436 of the conduit rear end portion 432 but simply frictionally slides axially into and out of contact therewith, thereby eliminating any need to rotate the cap unit 530 when installing on or removing same from the rear end of the conduit 430.

The friction engagement between the threaded interior of the conduit rear end portion 432 and the column 544, in addition to frictionally holding the cup-like body 531 fixed against accidental removal from the rear end portion of the conduit 430, also creates an axial fluid seal therebetween to prevent leakage of fluid rearwardly out of the interior of the conduit 430. Thus, as shown in FIG. 82, the column 544 in effect plugs the rear end of the conduit 430 to prevent liquid leakage therefrom.

The axially innermost end of the column 544 is relatively thin walled as indicated at 556 so that fluid pressure inside the conduit 430 tends to press radially outward on the thin resilient wall 556 to assist the fluid seal radially between the outside of the column 544 and the inside of the rear end portion of the conduit 430.

The interior of the column 544 has front and rear forwardly and rearwardly diverging coaxial frustoconical coaxial recesses 545 and 546 (FIG. 82) normally sealed from each other by an axially thin integral diaphragm 547.

The intact diaphragm 547 thus prevents fluid leakage from the conduit 430 through the central portion of the plug like column 544. However, the relatively thin diaphragm 547 can be intentionally pierced by pushing forward therethrough of a suitable relatively small diameter surgical tool (not shown), for example a laser probe, and in particular a surgical tool whose outside diameter is less than that of the diaphragm 547. The tapered recesses 546 and 545 in the column 544 help to guide the axial movement of such a surgical tool forwardly into and rearwardly out of the rear end of the column. The diaphragm 546, having been pierced by such a surgical tool, tends to at least partially seal around such surgical tool, when the latter is in place in the conduit 430 for use at a surgical site in front of the handpiece, to at least minimize liquid leakage rearwardly along the shank of such a surgical tool (not shown) and rearwardly out of the cap unit 530.

After a surgical tool has pierced the diaphragm 547 and then been withdrawn after use, the pierced, and now empty, diaphragm 547 may tend to allow some fluid leakage from the conduit 430. To avoid fluid leakage rearwardly out of the cap unit 530 under such circumstances, the central opening 550 in the bottom wall 532 of the cup-like body 531 is configured to be itself plugged against fluid leakage rearwardly therethrough, as follows. More particularly, the cap unit 530 includes a further integral strap 551 extending radially from the rear end portion thereof (here extending radially from the bottom wall 532, FIG. 82). The strap 551 is readily bendable from a relaxed radially extending position shown in dotted lines in FIG. 82 to a bent intermediate position shown in solid lines in FIG. 82. The strap 551 carries, remote from the cup-like body 531, an integral stopper portion 552 including a plug 553 adapted to be pushed forwardly into a correspondingly shaped, rearwardly opening, central opening 550 in the bottom wall 532 of the body 531 and which communicates axially with the rearward recess 546. The integral plug 553 includes a nose 554 tapered to facilitate insertion into the central opening 550. Such insertion is aided by tapering the rearward opening mouth 555 of such central opening. The plug 553 is spaced from the stopper portion 552 of the strap 551 by a short radially undercut neck 560. The central opening 550 in the bottom wall 532 is shaped to snugly compliment the plug 553 and the plug 553 can thus be pushed into a seated position within the opening 550 and can be pulled out of such position by the user with moderate axial force. The plug 553 when installed in the opening 550 snugly seats therein in a manner to close and seal the opening 550 against fluid leakage therethrough from the interior of the conduit 430.

Figure 83:
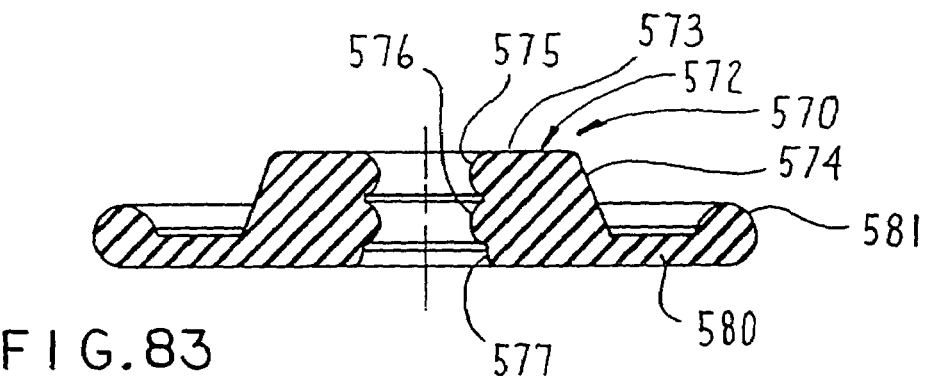
FIG. 83 is a central cross sectional view of an improved, low drag, pressure-aided shaft seal.
Figure 84:
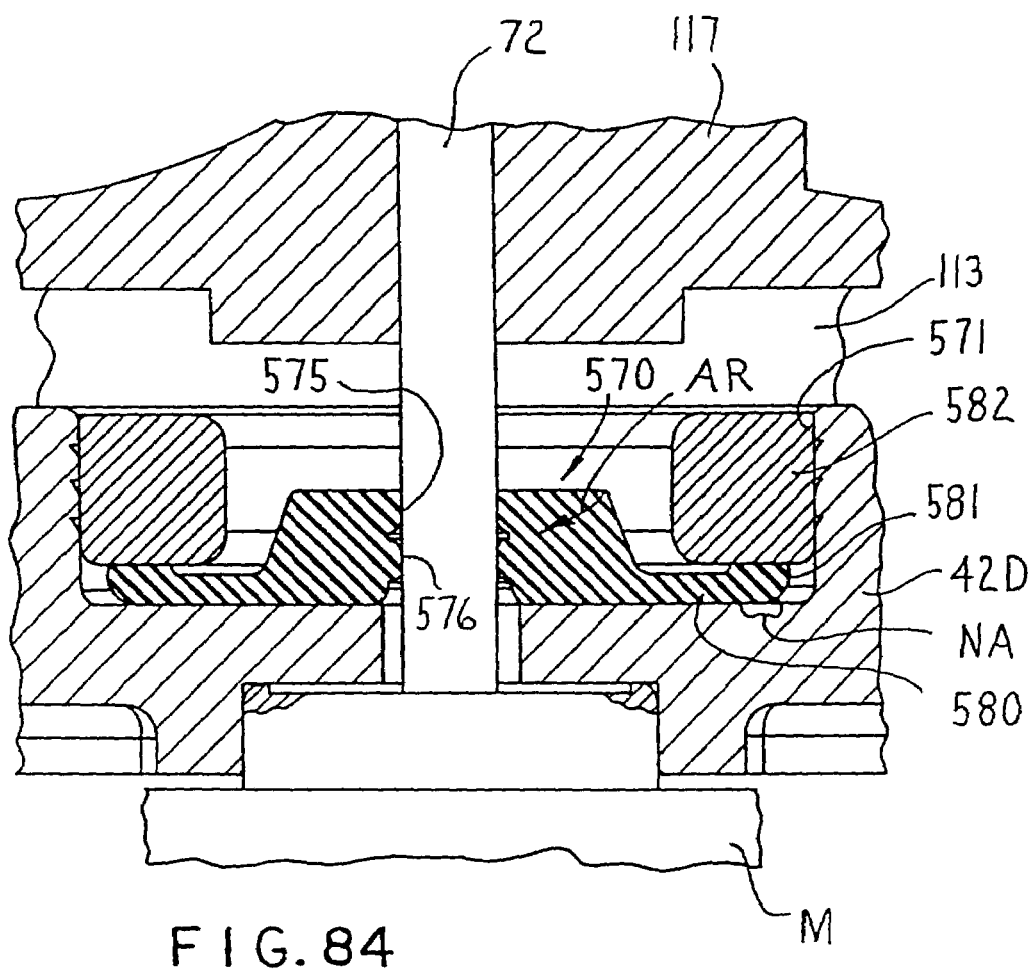
FIG. 84 is an enlarged fragment of FIG. 5 incorporating the FIG. 83 shaft seal.

FIGS. 83 and 84 disclose an improvement on the FIG. 5 pump motor shaft seal arrangement. FIG. 84 shows the motor M with its upstanding shaft 72 carrying the pump rotor, or impeller 117, in the pump chamber 113.

In the FIG. 81, 82 modification, the FIG. 5 seal 74 is eliminated and is replaced with a new seal ring 570 (FIGS. 83 and 84) to be located in a widened, upward opening seal recess 571 (FIG. 84) located preferably but not necessarily coaxially around the motor shaft 72 and atop the thus modified battery and motor locator 42D. The seal ring 570 is generally hat shaped, comprising an annular crown 572 having a flat top 573, a downwardly divergent outer side wall 574 and a coaxial through bore for sealingly receiving the rotating shaft 72. In the preferred embodiment shown, the upper part of the through bore is formed by a lip seal 575 which is radially inwardly convexly rounded and occupies approximately the top 40% of the through bore. The intermediate 40% of the height of the through bore is formed by a second lip seal 576 of similar shape. The bottom portion of the through bore diverges downwardly as indicated at 577 to form a bell-like bottom mouth 577. A substantially reduced thickness brim 580 extends radially outward from the bottom portion of the crown 572 and a thickened (here of substantially upstanding circular cross section) perimeter lip 581 coaxially bounds and is somewhat upstanding from the outer periphery of the substantially horizontal brim.

The seal recess 571 in the battery and motor locator 42D is substantially axially deeper and radially wider than the seal ring 570, as seen in FIG. 84. The seal ring 570 is of resilient rubber-like material and receives coaxially upwardly through the central bore thereof the rotatable motor shaft 72. The upper lip seal 575 bears sealingly on and surrounds the rotatable shaft 72 to prevent leakage of liquid from the pumping chamber 113 downward along the shaft 72 into neighborhood of the motor M. The convexly rounded profile of the lip seal 575 minimizes the axial height of contact between it and the rotating shaft 72 to minimize frictional drag on the shaft and hence minimize waste of battery energy on friction, which battery energy is preferably to be used instead for pumping liquid. Increased liquid pressure in the pumping chamber 113 results in increased pressure on the top 573 and frustoconical outer side wall 574 of the crown 572, thereby tending to in fact bend the central portion of the seal ring 570, or tilt same, inward and slightly downward toward the surface of the rotating shaft 72 generally in the direction of the arrow AR. The resulting increased pressure of the upper lip seal 575 on the shaft 72 increases the tightening of sealing. Accordingly, the seal ring 570 seals progressively more tightly against downward leakage of liquid from the pumping chamber 113 downwardly past the periphery of the shaft 72 as liquid pressure in the pumping chamber 113 rises. On the other hand, when pumping chamber pressure drops, the seal ring 570 less tightly grips the rotating shaft 72 and hence reduces friction therebetween and resulting energy loss to such friction. Accordingly, the seal ring 570 adapts to changing pressure conditions in the pumping chamber 113 to minimize energy loss to friction between itself and the rotating shaft 72 while yet providing adequate sealing to prevent liquid leakage downwardly therepast from pumping chamber 113, to thereby protect the motor and related components from wetting by the pumped liquid.

Liquid pressure in the pumping chamber 113 also helps keep the central body crown 272 of the seal ring 570 from moving axially upwardly toward the impeller 117.

The perimeter of the seal ring 570 is positively held against the bottom of recess 571 by an annular hoop 582, preferably of rigid plastic material, such as ABS, press fitted down into the recess 570 into compressive contact with the top of the perimeter lip 581 of the seal ring 570 in the manner shown in FIG. 84. The upstanding perimeter lip 581, being of limited radial extent, thus localizes the downward pressure of the hoop 582, which thus maximizes the downward pressure of the radially narrow perimeter portion of the seal ring 570 against the underlying bottom of the recess 571, to provide a very effective seal against leakage of liquid from the pumping chamber 113, which liquid might otherwise attempt to pass between the underside of the seal ring 570 and the bottom of the recess 571, to thereby reach and drain downward along the lower portion of the rotating motor shaft 72, into contact with the top of the casing of the motor M. In particular then the upstanding perimeter lip 581 of the seal ring 570 tends to concentrate the force of its sealing against the bottom of the recess 571 in a radially narrow annular area located immediately below the perimeter lip 581 and indicated at NA.

The axially thin but radially relatively wide brim 580 is relatively limp and flexible and effectively resiliently isolates the shaft seal area 575 from the recess bottom seal area 581, so that the shaft engaging lip seal 575 in effect floats radially with the shaft (should there be any radial movement of it with respect to the battery and motor locator 42) without influence by the sealing contact between the perimeter lip 581 and the hoop 582 and bottom of recess 571. Thus, the thin flexible brim 581 allows relative radial movement or misalignment between the shaft seal 575 and recess bottom seal 581, to accommodate radial movement (vibration or otherwise) of the shaft 72 without loss of sealing capability or frictional drag. Thus, sealing against liquid leakage past the seal ring 570 is independent of alignment between the motor shaft 72 and locator housing 42D.

In the preferred embodiment shown, the lower lip seal 576 similarly bears on the shaft 72 and acts as a back-up seal in case of unexpected unusual failure of the upper lip seal 575.

Figure 85:
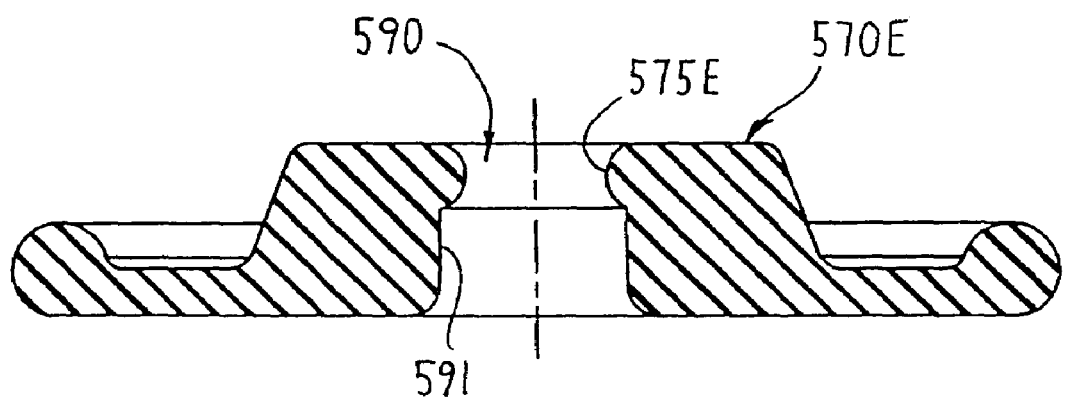
FIG. 85 is a view similar to FIG. 83 and showing a further modification.

FIG. 85 shows a modification of the FIG. 83, 84 seal ring, same being modified by elimination of the lower lip seal 575 of FIG. 83, so that in the area below the upper lip seal 575E of the modified seal ring 570E, the central through bore 590 is radially recessed as indicated at 591 so as to be free of contact with the shaft 72. The modified seal ring 570E is thus contemplated for use in situations wherein the operating life of the apparatus is to be shorter than in the FIGS. 83, 84 apparatus, i.e. wherein the use of the apparatus will be completed before there is appreciable wear of the upper lip seal 575E and hence the likelihood of wear damage that would make it desirable to have a back-up seal in the form of the lower lip seal 576 of FIGS. 83, 84.

Although preferred embodiments of the invention have been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A surgical irrigation system, comprising: a handpiece locatable adjacent a surgical site and comprising an irrigation liquid inlet and an irrigation liquid outlet; a motor/pump unit locatable remote from said handpiece and comprising a motor having a shaft and a housing including a receptacle having an end opening, a cover, and a motor receiving member axially opposing said receptacle and said cover; said motor receiving member comprising an end wall and a hollow tubular wall extending from said end wall and defining a recess, said end wall having a hole therethrough, said motor being received in said recess with said shaft extending through said hole in said end wall, said motor receiving member being interposed between said receptacle and cover; said cover comprising the open ended dome having a roof and a peripheral wall extending from said roof, said motor receiving member being received in said dome, an annular seal ring radially interposed between said motor receiving member and a surrounding portion of said peripheral wall of said dome, said motor receiving member being axially spaced from said roof of said dome by a pumping chamber, an impeller fixed on said shaft about said motor receiving member and disposed in said pumping chamber, said pumping chamber having an irrigation liquid inlet and an irrigation liquid outlet; an elongate irrigation liquid path connecting said irrigation liquid outlet of said motor/pump unit to said irrigation liquid inlet of said handpiece.

2. The apparatus of claim 1 in which said receptacle is circular.

3. The apparatus of claim 1 in which said receptacle has a side wall and an end wall, said cover having a flange extending radially outboard of said peripheral wall thereof substantially to said side wall of said receptacle.

4. The apparatus of claim 3 in which said motor receiving member has a flange extending radially outboard and axially interposed between said flange of said cover and the top edge of said side wall of said receptacle member.

5. The apparatus of claim 3 in which said flange of said cover includes a generally L-profile tab extending from a radially outer portion of said flange and having a radially extending lip, fixing structure fixing said cover with respect to said receptacle and said motor receiving member, said fixing structure including said tab.

6. The apparatus of claim 5 in which said motor receiving member has a flange extending radially outboard, said tab extending through an opening in said flange of said motor receiving member.

7. The apparatus of claim 1 in which said receptacle has a side wall and an end wall, said motor having an end facing a central portion of said end wall of said receptacle, said receptacle having a battery receiving zone surrounding said central portion and within said side wall and including side-by-side, axially elongate, battery receiving spaces.

8. The apparatus of claim 7 in which said receptacle defines a cup and at least a portion of said motor extends into said cup.

9. The apparatus of claim 1 in which said receptacle has a central portion and a side wall, said housing including generally circumferentially distributed, battery separator elements disposed along and extending between said central portion and side wall of said receptacle, said separator elements having radially inboard and outboard portions which extend in a generally circumferential direction sufficient to block radial inward and outward battery displacement in said receptacle.

10. The apparatus of claim 9 in which said separator elements are fixed to and radially extend from said hollow tubular wall of said motor receiving member.

11. The apparatus of claim 1 in which said housing includes generally circumferentially distributed battery separator elements, first and second sets of electrically conductive battery contacts, said first set comprising at least one electrically conductive spring wire contact which comprises a bight connecting a pair of spring portions having a battery engaging surface, said spring portions being laterally located by said battery separating elements, said second set comprising conductive, generally plate-like contacts of which at least one comprises a pair of spaced disks connected by a strip and another comprises separate terminals in circuit with said motor.

12. The apparatus of claim 11 in which said receptacle has a side wall and a bottom wall, said motor receiving member further comprising a deck radially outwardly extending from said hollow tubular wall, said battery separating elements extending radially outboard from said hollow tubular wall and extending axially from said deck and defining battery receiving grooves therebetween, said spring portions of a given said contact being disposed in adjacent ones of said grooves with the corresponding said bight spanning the intervening separating element and the bases of said spring portions being adjacent said deck, said disks being respectively fixedly located coaxially with adjacent ones of said grooves but lying fixedly adjacent said end wall of said receptacle.

13. A surgical irrigator system, comprising:
a handpiece having an irrigation liquid outlet opposable to a surgical site;
a motor/pump unit comprising a pumping chamber having a floor, a roof spaced above said floor and a peripheral wall generally upstanding between said floor and roof, said pumping chamber having a shaft extending substantially coaxially into said pumping chamber through said floor and toward said roof, an impeller fixed for rotation with said shaft, said pumping chamber having a liquid inlet substantially coaxial with said shaft and opening into said pumping chamber through said roof, said pumping chamber having a liquid outlet extending substantially tangentially through said peripheral wall, and an electrical motive power source rotatably driving said shaft;
a liquid path connecting said outlet and handpiece;
a pole-engageable, motor/pump unit support member extending from said motor/pump unit and adapted to support said motor/pump unit on an irrigation liquid container support pole; and
a generally tubular, elongate, liquid receiving member extending from said roof adjacent said inlet and having a remote free end portion including an irrigation liquid container connection structure.

14. The apparatus of claim 13, including an upstanding pole having an irrigation liquid container support fixed on said pole, said motor/pump unit support member fixedly locating said motor/pump unit adjacent said irrigation liquid container support.

15. The apparatus of claim 14, including an irrigation liquid container having an irrigation liquid outlet, said irrigation liquid container being supported by said irrigation liquid container support.

16. The apparatus of claim 15, in which said irrigation liquid container comprises a bag fixed on said irrigation liquid container support.

17. The apparatus of claim 13 in which said generally tubular, elongate, liquid receiving member comprises an outlet portion formed as an upstanding extension of said roof and having a liquid outlet end open to said pumping chamber, said generally tubular, elongate, liquid receiving member comprising an inlet portion including said irrigation liquid container connection structure, and a passage connecting said inlet and outlet portions.

18. The apparatus of claim 13 in which said generally tubular, elongate, liquid receiving member comprises an outlet portion open to said pumping chamber, and further comprises an inlet portion including said irrigation liquid container connection structure, and a passage connecting said inlet and outlet portions, said inlet portion being of hollow tubular shape with an outer periphery generally tapered toward its inlet end and a releasably fixing surface treatment to releasably fix in an outlet of an irrigation liquid container.

19. The apparatus of claim 18 in which said surface treatment is a radial protrusion engagable with an irrigation liquid supply container outlet.

20. The apparatus of claim 13 in which said liquid receiving member comprises a hollow tubular spike integral with said roof and having said inlet and outlet portions adjacent opposite ends thereof.

21. The apparatus of claim 13 in which said motor/pump unit further comprises a cup-like battery receiver fixed under said pumping chamber, said pole-engaging, motor/pump unit support member extending from said battery receiver.

22. A surgical irrigation system, comprising:
a handpiece for directing irrigation liquid to a surgical site, said handpiece having a manually actuable member having liquid flow blocking and liquid flow permitting positions;
a pumping unit locatable remotely from said handpiece, an elongate irrigation liquid tube connecting said pumping unit to said handpiece for delivery of irrigation liquid from said pumping unit to said handpiece, said pumping unit including a pumping chamber having an outlet connected to said irrigation liquid tube, said pumping chamber having an inlet, a tubular protrusion coupled to and upstanding from said inlet for receiving irrigation liquid, said tubular protrusion having an open, liquid receiving, free end spaced from said pumping chamber, a liquid pumping member in said pumping chamber adjacent said tubular protrusion, a motor drivingly coupled to said liquid pumping member, said motor having an energized condition corresponding to at least one said flow permitting position of said manually actuable member of said handpiece.

23. The apparatus of claim 22 in which said tubular protrusion open end faces at an acute angle to a longitudinal axis of said tubular protrusion.

24. The apparatus of claim 22 in which said tubular protrusion has an outboard portion spaced from said pumping chamber and having a relatively gradual taper away from said pumping chamber, said tubular protrusion having an inboard portion flared radially outward adjacent said pumping chamber at a relatively greater taper which decreases toward said outer portion.

25. A surgical irrigation system connectable to a conventional independent irrigation liquid supply container, said system comprising:
a handpiece for directing irrigation liquid to a surgical site;
a compact pumping unit locatable remotely from the handpiece and surgical site, an elongate irrigation liquid tube connecting said pumping unit to said handpiece for delivery of pumped irrigation liquid from said pumping unit to said handpiece, said pumping unit comprising a motor having a power source connector, a pumping member drivingly coupled to said motor and coupled in irrigation liquid pumping relation with said elongate tube and through said elongate tube to said handpiece, a cover enclosing a pumping chamber occupied by said pumping member and having an irrigation liquid outlet connected to said elongate tube, said cover further including an irrigation liquid inlet opening, a tubular liquid transfer member protruding from said cover, said tubular liquid transfer member having an outer, sealing surface configured for sealed insertion into an outlet fitting of an independent conventional irrigation liquid supply container, said tubular liquid transfer member being formed as an elongate hollow tube having a generally central, irrigation liquid bore extending substantially the length of said tube, said bore having an upper end open to receive irrigation liquid from a liquid supply container, said bore having a lower end open at and to said cover irrigation liquid inlet opening in irrigation liquid directing relation into said pumping chamber, whereby insertion of said tube into the inlet fitting of a conventional irrigation liquid supply container causes the outside of the tube to sealingly engage the pumping unit and enables said bore to supply liquid to said pumping chamber.

26. The apparatus of claim 25 in which a distal portion of said tube is tapered and includes a peripheral surface adapted to capture by a liquid outlet fitting of an irrigation liquid supply container.

27. The apparatus of claim 26 wherein said tube is a hollow spike upstanding from said cover.

28. The apparatus of claim 25 in which said pumping unit includes a cup-like battery receiver fixed below said pumping chamber.

29. The apparatus of claim 28 in which said receiver comprises a top-opening cup having upstanding, circumferentially distributed battery stations surrounding a central zone, said pumping unit including conductors electrically connecting said battery stations in circuit with said motor to drive said pumping member.

* * * * *